(12) United States Patent
Curran et al.

(10) Patent No.: US 6,743,917 B2
(45) Date of Patent: Jun. 1, 2004

(54) CAMPTOTHECIN ANALOGS AND METHODS OF PREPARATION THEREOF

(75) Inventors: Dennis P. Curran, Pittsburgh, PA (US); Hubert Josien, Jersey City, NJ (US); David Bom, Pittsburgh, PA (US); Thomas G. Burke, Lexington, KY (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 10/134,781

(22) Filed: Apr. 29, 2002

(65) Prior Publication Data

US 2002/0193598 A1 Dec. 19, 2002

Related U.S. Application Data

(63) Continuation of application No. 09/613,968, filed on Jul. 11, 2000, now abandoned, which is a continuation of application No. 09/212,178, filed on Dec. 15, 1998, now Pat. No. 6,136,978, which is a continuation-in-part of application No. 08/921,102, filed on Aug. 29, 1997, now Pat. No. 6,150,343, which is a continuation-in-part of application No. 08/436,799, filed on May 8, 1995, now abandoned, which is a continuation-in-part of application No. 08/085,190, filed on Jun. 30, 1993, now abandoned.

(51) Int. Cl.[7] .......................... C07D 405/14; C07F 7/10
(52) U.S. Cl. ....................................................... 546/14
(58) Field of Search .......................................... 546/14

(56) References Cited

U.S. PATENT DOCUMENTS

| | | | |
|---|---|---|---|
| 5,468,859 A | 11/1995 | Fortunak | 546/48 |
| 5,700,939 A | 12/1997 | Fortunak | 546/116 |
| 5,744,605 A | 4/1998 | Curran | 546/70 |
| 5,910,491 A | * 6/1999 | Hausheer et al. | 546/14 |
| 5,935,967 A | 8/1999 | Hausheer | 514/283 |
| 6,150,343 A | 11/2000 | Curran | 546/63 |
| 6,211,371 B1 | 4/2001 | Curran | 546/48 |
| 6,252,079 B1 | 6/2001 | Curran | 546/51 |

FOREIGN PATENT DOCUMENTS

| | | |
|---|---|---|
| CN | 99815768.6 | 10/2002 |
| WO | WO 98/07727 | 2/1998 |
| WO | WO 98/35940 | 8/1998 |

OTHER PUBLICATIONS

Curran, D.P. and Liu, H., "New 4+1 Radical Annulations—A Formal Total Synthesis of (+/–)–Camptothecin," J. Am. Chem Soc., 114, 5863–5864 (1992). Published Jul. 1, 1992.

Curran, D.P., "The Camptothecins—A reborn Family of Antitumor Agents", J. Chin. Chem. Soc., 40, 1–6 (1993). Published Feb. 1993.

Curran, D.P. et al., "Recent Applications of Radical Reactions in Natural Product Synthesis," Pure Appl. Chem., 65, 1153–1159 (1993). Published Jun. 1993.

Curran, D.P. et al., "Cascade Radical Reactions of Isonitriles: A Second–Generation Synthesis of (20S)–Camptothecin, Topotecan, Irinotecan, and GI–147211C," Angew. Chem. Int. Ed, 34, 2683–2684 (1995). Published Jan. 5, 1996.

Curran, D.P., Liu, H.; Josien, H; Ko, S.B., "Tandem Radical Reactions of Isonitriles with 2–pyrdonyl and other aryl radicals: Scope and Limitations, and a First Generation Sunthesis of (+/–)–Camptothecin," Tetrahedron, 52, 11385–11404 (1996). Published Aug. 1996.

Josien, H. et al., "Synthesis of (S)–mappicine and Mappicine Ketone Via Radical Cascade Reaction of Isonitirles," Tetrahedron, 53, 8881–8886 (1997). Published Jun. 30, 1997.

Josien, H. et al., "7–Silylcamptothecins (Silatecans): A New Family of Camptothecin Antitumor Agents," Bioorg. Med. Chem. Lett. vol. 7, No. 24, 3189–3295 (1997).

Josien, H. et al., "A General Synthetic Approach to the (20S)–Camptothecin Family of Antitumor Agents by a Regiocontrolled Cascade Radical Cyclization of Aryl Isonitriles," Chem. Eur. J. 4, 67–83 (1998). Published Jan. 1998.

\* cited by examiner

Primary Examiner—John M. Ford
(74) Attorney, Agent, or Firm—Bartony & Hare, LLP

(57) ABSTRACT

A compound and a method of synthesizing a compound having the following general formula (1):

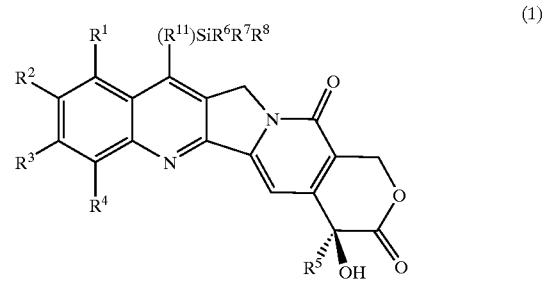

(1)

wherein $R^1$ and $R^2$ are independently the same or different and are hydrogen, an alkyl group, an alkenyl group, a benzyl group, an alkynyl group, an alkoxy group, an aryloxy group, an acyloxy group, —OC(O)OR$^d$, wherein R$^d$ is an alkyl group, a carbamoyloxy group, a halogen, a hydroxy group, a nitro group, a cyano group, an azido group, a formyl group, a hydrazino group, an acyl group, an amino group, —SR$^c$, wherein, R$^c$ is hydrogen, an acyl group, an alkyl group, or an aryl group, or $R^1$ and $R^2$ together form a group of the formula —O(CH$_2$)$_n$O— wherein n represents the integer 1 or 2; $R^3$ is H, F, a halogen atom, a nitro group, an amino group, a hydroxy group, or a cyano group; or $R^2$ and $R^3$ together form a group of the formula —O(CH$_2$)$_n$O— wherein n represents the integer 1 or 2; $R^4$ is H, a trialkylsilyl group, F, a C$_{1-3}$ alkyl group, a C$_{2-3}$ alkenyl group, a C$_{2-3}$ alkynyl group, or a C$_{1-3}$ alkoxy group; $R^5$ is a C$_{1-10}$ alkyl group, an allyl group, a benzyl group or a propargyl group; and $R^6$, $R^7$ and $R^8$ are independently a C$_{1-10}$ alkyl group, a C$_{2-10}$ alkenyl group, a C$_{2-10}$ alkynyl group, an aryl group or a —(CH$_2$)$_N$R$^9$ group, wherein N is an integer within the range of 1 through 10 and $R^9$ is a hydroxy group, alkoxy group, an amino group, an alkylamino group, a dialkylamino group, a halogen atom, a cyano group or a nitro group; and $R^{11}$ is an alkylene group or an alkenylene group, and pharmaceutically acceptable salts thereof.

19 Claims, 25 Drawing Sheets

Synthesis of 3

(36a) R¹ = OH
(36b) R¹ = NH₂
(36c) R¹ = H

CAMPTOTHECIN ANALOGS AND METHODS OF PREPARATION THEREOF

CROSS-REFERENCE TO RELATED APPLICATIONS

This application is a continuation application of U.S. patent application Ser. No. 09/613,968, now abandoned which is a continuation application of U.S. patent application Ser. No. 09/212,178, now U.S. Pat. No. 6,136,978, which is a continuation-in-part application of U.S. patent application Ser. No. 08/921,102, now U.S. Pat. No. 6,150,343 which is a continuation-in-part application of U.S. patent application Ser. No. 08/436,799, now abandoned which is a continuation-in-part application of U.S. patent application Ser. No. 08/085,190, now abandoned the disclosures of which are incorporated herein by reference.

FIELD OF THE INVENTION

The present invention relates to novel compounds and methods of preparation thereof and, particularly, to silyl camptothecin derivatives or analogs and to methods of preparation of such silyl camptothecin analogs.

BACKGROUND OF THE INVENTION (20S)-Camptothecin (CPT, see below) and its derivatives are some of the most promising agents for the treatment of solid tumors by chemotherapy. See, for example, Wall, M. E. et al, *J. Ethnopharmacol.*, 51, 239 (1996); *Camptothecin: New Anticancer Agents;* Potmesil, M. and Pinedo, H., Eds.; CRC, Boca Raton, Fla. (1995); Bonneterre, J., *Bull. Canc.*, 82, 623 (1995); Sinha, D. K., *Drugs*, 49, 11 (1995). This natural alkaloid was first isolated in 1966 from the extract of a Chinese plant, *Camptotheca accuminata*, by Wall. Wall, M. E. et al, *J. Am. Chem. Soc.*, 88, 3888 (1966). As depicted below, camptothecin has a fused ring system generally comprising a pyrrolo[3,4-b]quinoline system (rings ABC) fused to a 2-pyridone ring (ring D), which, in turn, is fused to a lactone ring (ring E).

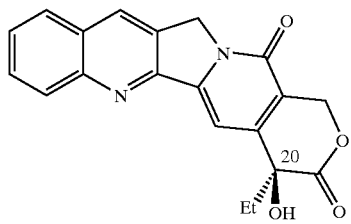

(20S)-camptothecin, CPT
Rings are labeled A-E from left to right

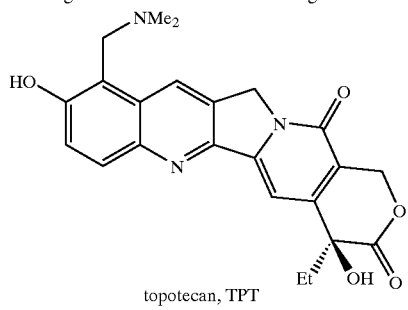

topotecan, TPT

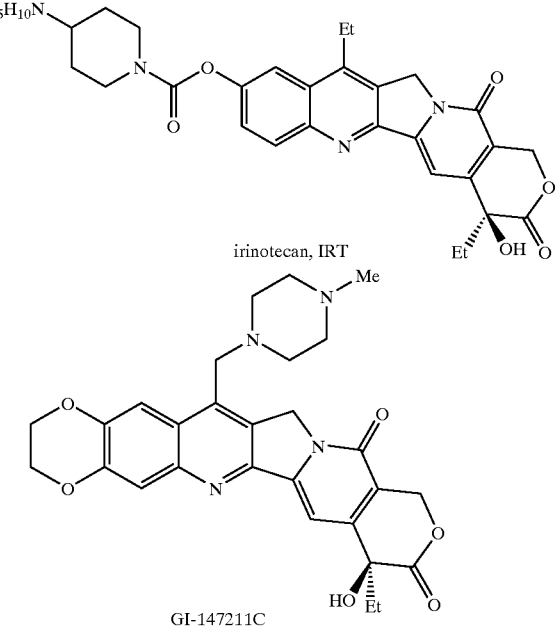

irinotecan, IRT

GI-147211C

Camptothecin belongs to the family of topoisomerase I poisons. See, for example, Froelich-Ammon, S. J. et al., *J. Biol. Chem.*, 270, 21429 (1995). Research to date strongly suggests that this molecule acts by interfering with the unwinding of supercoiled DNA by the cellular enzyme topoisomerase I, an enzyme which is usually overexpressed in malignant cells. In the highly replicating cancer cells, this triggers a cascade of events leading to apoptosis and programmed death. See Slichenmyer, W. J. et al., *J. Natl. Cancer Inst.*, 85, 271 (1993). Recent advances at the molecular pharmacology level are reviewed in Pommier, Y. et al., *Proc. Natl. Acad. Sci. USA*, 92, 8861 (1995).

Camptothecin's initial clinical trials were limited by its poor solubility in physiologically compatible media. Moreover, early attempts to form a water-soluble sodium salt of camptothecin by opening the lactone ring with sodium hydroxide resulted in a compound having a poor antitumor activity. It was later reported that the closed lactone-form is an absolute requisite for antitumor activity. See Wani, M. C. et al., *J. Med. Chem.*, 23, 554 (1980). More recently, structure-activity studies have identified analogous compounds with better solubility and better antitumor activity. For example, topotecan (TPT) and irinotecan (IRT) have recently been approved for sale in the United States, while GI-147211C is in late stage clinical trials. These analogs are effective against a variety of refractory solid tumors such as malignant melanoma, stomach, breast, ovarian, lung and colorectal cancers, and seem particularly promising for the treatment of slow-dividing cancer lines. See, for example, Kingsbury, W. D. et al., *J. Med. Chem.*, 34, 98 (1991); Sawada, S. et al., *Chem. Pharm. Bull.*, 39, 1446 (1991); Luzzio, M. J. et al., *J. Med. Chem.*, 38, 395 (1995); Abigerges, D. et al., *J. Clin. Oncol.*, 13, 210 (1995). Furthermore, synergistic or additive effects have been observed in combination therapies with cisplatin, irradiation, or hyperthermia. See Fukuda, M. et al., *Canc. Res.*, 56, 789 (1996); Goldwasser, F. et al., *Clin. Canc. Res.*, 2, 687 (1996); Wang, D. S. et al., *Biol. Pharm. Bull.*, 19, 354 (1996).

Although most research has focused on the development of water-soluble derivatives of camptothecin, new formulations, such as lipid-complexation, liposomal encapsulation, and wet milling technology have recently been developed. Such formulations result in new therapeutic opportunities for poorly water-soluble camptothecins. See Daoud, S. S. et al., *Anti-Cancer Drugs*, 6, 83 (1995); Merisko-Liversidge, E. et al., *Pharm. Res.*, 13, 272 (1996); and Pantazis, P., *Leukemia Res.*, 19, 775 (1995). An attractive feature of these formulations is their impact on drug biodistribution. Sugarman and coworkers have recently reported that while free camptothecin achieves the greatest concentration in the pulmonary parenchyma, lipid-complexed camptothecin has the highest concentration in the gastrointestinal tract. These results open new and interesting perspectives for the treatment of colon cancer. See Sugarman, S. M. et al., *Canc. Chemother. Pharmacol.*, 37, 531 (1996). Another interesting aspect of using insoluble camptothecin analogs is that they are usually more active than their water-soluble congeners and seem less likely to create drug-induced resistance, probably because they are not substrates of the p-glycoprotein multi-drug transporter. See Pantazis, P., *Clin. Canc. Res.*, 1, 1235 (1995).

In this context, new camptothecin analogs that combine good to excellent anti-tumor activities with different solubility and biodistribution profiles could play a crucial role in the therapeutic arsenal for the treatment of various types of cancers.

Given the proven beneficial biological activity of camptothecin and analogs thereof, it is desirable to develop additional camptothecin analogs and methods of preparation of camptothecin analogs.

SUMMARY OF THE INVENTION

The present invention provides generally a compound having the following formula (1):

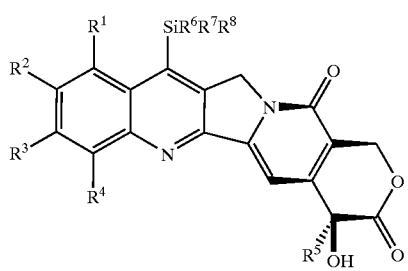

(1)

The present invention also provides a method of synthesizing compounds having the formula (2):

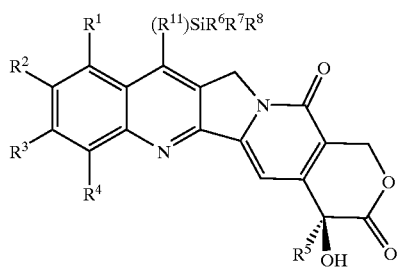

via a 4+1 radical annulation/cyclization wherein the precursor

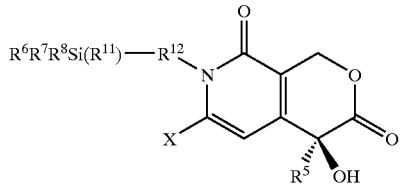

is reacted with an aryl isonitrile having the formula

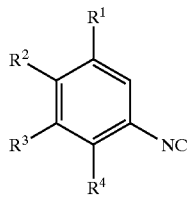

$R^1$ and $R^2$ are independently the same or different and are preferably hydrogen, an alkyl group, an alkenyl group, an alkynyl group, an alkoxy group, an aryloxy group, an acyloxy group, —OC(O)OR$^d$, wherein R$^d$ is an alkyl group, a carbamoyloxy group, a halogen, a hydroxy group, a nitro group, a cyano group, an azido group, a formyl group, a hydrazino group, an acyl group(—C(O)R$^f$ wherein R$^f$ is preferably an alkyl group, an alkoxy group, an amino group or a hydroxy group), an amino group, —SR$^e$, wherein, R$^e$ is hydrogen, an acyl group, an alkyl group, or an aryl group, or $R^1$ and $R^2$ together form a group of the formula —O(CH$_2$)$_n$O— wherein n represents the integer 1 or 2.

$R^3$ is preferably H, a halogen, a nitro group, an amino group, a hydroxy group, or a cyano group. $R^2$ and $R^3$ can also together form a group of the formula —O(CH$_2$)$_n$O— wherein n represents the integer 1 or 2.

$R^4$ is preferably H, F, a trialkylsilyl group, a $C_{1-3}$ alkyl group, a $C_{2-3}$ alkenyl group, a $C_{2-3}$ alkynyl group, or a $C_{1-3}$ alkoxy group. $R^5$ is preferably a $C_{1-10}$ alkyl group. A preferred alkyl group is an ethyl group. Preferred substituted alkyl groups for $R^5$ include an allyl group, a propargyl and a benzyl group.

$R^6$, $R^7$ and $R^8$ preferably are independently (the same or different) a $C_{1-10}$ alkyl group, a $C_{2-10}$ alkenyl group, a $C_{2-10}$ alkynyl group, or an aryl group. A preferred substituted alkyl group for $R^6$, $R^7$ and $R^8$ is a —(CH$_2$)$_N$R$^9$ group, wherein N is an integer within the range of 1 through 10 and $R^9$ is a hydroxy group, an alkoxy group, an amino group, a halogen atom, a cyano group or a nitro group. Preferred amino groups for $R^9$ include alkylamino groups and a dialkylamino groups.

$R^{11}$ is preferably an alkylene group, an alkenylene or an alkynylene group. $R^{12}$ is preferably —CH=CH—CH$_2$— or —C≡C—CH$_2$—. X is preferably Cl, Br or I. More preferably, X is Br or I. Most preferably, X is Br.

The present invention also provides a compound having the formula (2):

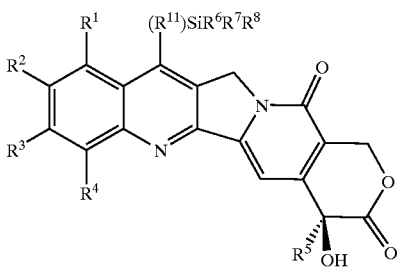

(2)

wherein $R^1$, $R^2$, $R^3$, $R^4$, $R^5$, $R^6$, $R^7$, $R^8$ and $R^{11}$ are as defined prior to this paragraph. The present invention further provides a compound of the above formula wherein one of $R^1$, $R^2$, $R^3$, and $R^4$ is not H. The present invention still further provides a compound of the above formula wherein $R^1$, $R^2$, $R^3$, $R^4$, $R^5$, $R^6$, $R^7$, $R^8$ and $R^{11}$ are as defined prior to this paragraph and wherein $R^5$ is a methyl group, a $C_{3-10}$ alkyl group, an allyl group, a benzyl group or a propargyl group.

The present invention further provides a compound having the following formula (3):

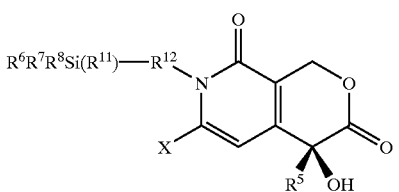

(3)

The present invention further provides a compound having the following formula (4):

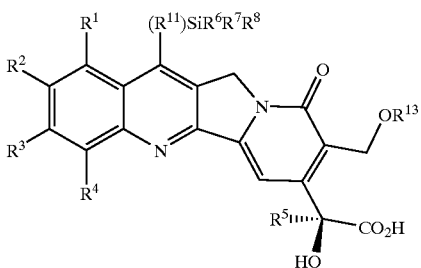

(4)

The terms "alkyl", "aryl" and other groups refer generally to both unsubstituted and substituted groups unless specified to the contrary. Unless otherwise specified, alkyl groups are hydrocarbon groups and are preferably $C_1$–$C_{15}$ (that is, having 1 to 15 carbon atoms) alkyl groups, and more preferably $C_1$–$C_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "aryl" refers to phenyl or napthyl. As used herein, the terms "halogen" or "halo" refer to fluoro, chloro, bromo and iodo.

The term "alkoxy" refers to —$OR^d$, wherein $R^d$ is an alkyl group. The term "aryloxy" refers to —$OR^e$, wherein $R^e$ is an aryl group. The term acyl refers to —$C(O)R^f$. The term "alkenyl" refers to a straight or branched chain hydrocarbon group with at least one double bond, preferably with 2–15 carbon atoms, and more preferably with 3–10 carbon atoms (for example, —CH=$CHR^g$). The term "alkynyl" refers to a straight or branched chain hydrocarbon group with at least one triple bond, preferably with 2–15 carbon atoms, and more preferably with 3–10 carbon atoms (for example, —C≡$CR^h$). The terms "alkylene," "alkenylene" and "alkynylene" refer to bivalent forms of alkyl, alkenyl and alkynyl groups, respectively.

The groups set forth above, can be substituted with a wide variety of substituents to synthesize camptothecin analogs retaining activity. For example, alkyl groups may preferably be substituted with a group or groups including, but not limited to, a benzyl group, a phenyl group, an alkoxy group, a hydroxy group, an amino group (including, for example, free amino groups, alkylamino, dialkylamino groups and arylamino groups), an alkenyl group, an alkynyl group and an acyloxy group. In the case of amino groups (—$NR^aR^b$), $R^a$ and $R^b$ are preferably independently hydrogen, an acyl group, an alkyl group, or an aryl group. Acyl groups may preferably be substituted with (that is, $R^f$ is) an alkyl group, a haloalkyl group (for example, a perfluoroalkyl group), an alkoxy group, an amino group and a hydroxy group. Alkynyl groups and alkenyl groups may preferably be substituted with (that is, $R^g$ and $R^h$ are preferably) a group or groups including, but not limited to, an alkyl group, an alkoxyalkyl group, an amino alkyl group and a benzyl group.

The term "acyloxy" as used herein refers to the group —$OC(O)R^d$.

The term "alkoxycarbonyloxy" as used herein refers to the group —$OC(O)OR^d$.

The term "carbamoyloxy" as used herein refers to the group —$OC(O)NR^aR^b$.

Amino and hydroxy groups may include protective groups as known in the art. Preferred protective groups for amino groups include tert-butyloxycarbonyl, formyl, acetyl, benzyl, p-methoxybenzyloxycarbonyl, trityl. Other suitable protecting groups as known to those skilled in the art are disclosed in Greene, T., Wuts, P. G. M., *Protective Groups in Organic Synthesis*, Wiley (1991), the disclosure of which is incorporated herein by reference.

In general, $R^1$, $R^2$, $R^3$, $R^6$, $R^7$ and $R^8$ are preferably not excessively bulky to maintain activity of the resultant camptothecin analog. Preferably, therefore, $R^1$, $R^2$, $R^3$, $R^6$, $R^7$ and $R^8$ independently have a molecular weight less than approximately 250. More preferably $R^1$, $R^2$, $R^3$, $R^6$, $R^7$ and $R^8$ independently have a molecular weight less than approximately 200.

Some of the camptothecin analogs of the present invention can be prepared for pharmaceutical use as salts with inorganic acids such as, but not limited to, hydrochloride, hydrobromide, sulfate, phosphate, and nitrate. The camptothecin analogs can also be prepared as salts with organic acids such as, but not limited to, acetate, tartrate, fumarate, succinate, citrate, methanesulfonate, p-toluenesulfonate, and stearate. Other acids can be used as intermediates in the preparation of the compounds of the present invention and their pharmaceutically acceptable salts.

For purification, administration or other purposes, the E-ring (the lactone ring) may be opened with alkali metal such as, but not limited to, sodium hydroxide or calcium hydroxide, to form opened E-ring analogs of compounds of formula (1) as set forth in the compounds of formula (4). The intermediates thus obtained are more soluble in water and may be purified to produce, after treatment with an acid, a purified form of the camptothecin analogs of the present invention.

The E-ring may also be modified to produce analogs of compounds of formula (1) with different solubility profiles in water or other solvents. Methods to achieve this goal include, but are not limited to, opening the E-ring with hydroxide or a water-soluble amino group or functionalizing the hydroxy group at position 20 of the E-ring with a water-soluble group such as a polyethylene glycol group. The analogs thus prepared act as pro-drugs. In other words, these analogs regenerate the compounds of formula (1) (with the closed E-ring structure) when administered to a living organism. See, Greenwald, R. B. et al., *J. Med. Chem.*, 39, 1938 (1996).

The analogs of the present invention are highly lipophilic and have been shown to enhance activity both in vivo and in vitro. Moreover, their A-ring substitution(s) have been shown to enhance blood stability.

The present invention also provides a method of treating a patient, which comprises administering a pharmaceutically effective amount of a compound of formulas (1) and/or (2) or a pharmaceutically acceptable salt thereof. The compound may, for example, be administered to a patient afflicted with cancer and/or leukemia by any conventional route of administration, including, but not limited to, intravenously, intramuscularly, orally, subcutaneously, intratumorally, intradermally, and parenterally. The pharmaceutically effective amount or dosage is preferably between 0.01 to 60 mg of one of the compounds of formulas (1) and (2) per kg of body weight. More preferably, the pharmaceutically effective amount or dosage is preferably between 0.1 to 40 mg of one of the compounds of formulas (1) and (2) per kg of body weight. In general, a pharmaceutically effective amount or dosage contains an amount of one of the compounds of formulas (1) and (2) effective to display antileukemic and/or antitumor (anticancer) behavior. Pharmaceutical compositions containing as an active ingredient of one of the compounds of formulas (1) and (2) or a pharmaceutically acceptable salt thereof in association with a pharmaceutically acceptable carrier or diluent are also within the scope of the present invention.

The present invention also provides a pharmaceutical composition comprising any of the compounds of formulas (1) and (2) and a pharmaceutically acceptable carrier. The composition may, for example, contain between 0.1 mg and 3 g, and preferably between approximately 0.1 mg and 500 mg of the compounds of formulas (1), (2) and/or (4), and may be constituted into any form suitable for the mode of administration.

DETAILED DESCRIPTION OF THE INVENTION

Compounds

Among the compounds of formulas (1) and (2), those having the (S)-configuration at position 20 of the E-ring are preferred for pharmaceutical use.

$R^1$ and $R^2$ are preferably and independently (the same or different) H, a hydroxy group, a halo group, an amino group, a nitro group, a cyano group, a $C_{1-3}$ alkyl group, a $C_{1-3}$ perhaloalkyl group, a $C_{1-3}$ alkenyl group, a $C_{1-3}$ alkynyl group, a $C_{1-3}$ alkoxy group, a $C_{1-3}$ aminoalkyl group, a $C_{1-3}$ alkylamino group, a $C_{1-3}$ dialkylamino group, or $R^1$ and $R^2$ together form a group of the formula —O(CH$_2$)$_n$O— wherein n represents the integer 1 or 2. More preferably, $R^1$ and $R^2$ are independently (the same or different) H, a methyl group, an amino group, a nitro group, a cyano group, a hydroxy group, a hydroxymethyl group, a methylamino group, a dimethylamino group, an ethylamino group, a diethylamino group, an aminomethyl group, a methylaminomethyl group, a dimethylaminomethyl group, and the like.

$R^3$ is preferably F, an amino group, or a hydroxy group. $R^4$ is preferably H, a trialkylsilyl group or F. $R^5$ is preferably an ethyl group. $R^6$, $R^7$ and $R^8$ are preferably independently (the same or different) a $C_{1-6}$ alkyl group, a phenyl group or a —(CH$_2$)$_N$R$^{10}$ group, wherein N is an integer within the range of 1 through 6 and $R^{10}$ is a halogen or a cyano group.

Method of Preparation

Figure 1:
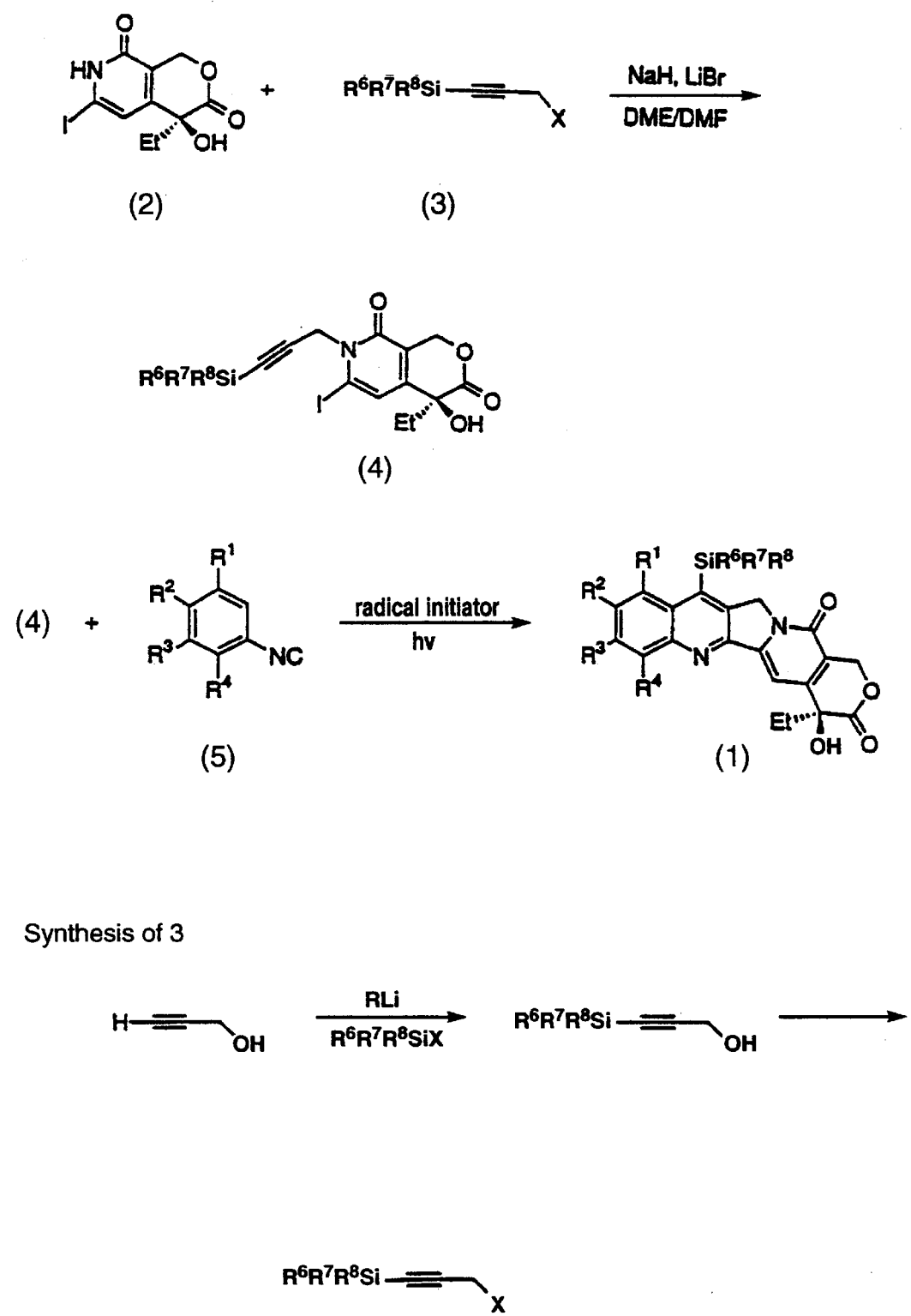
FIG. 1 is an illustration of a general synthetic scheme for the preparation of compounds of formula (1).

The compounds of formula (1) of the present invention can be prepared according to the general synthetic scheme shown in FIG. 1. In the synthetic scheme of FIG. 1, an iodopyridone (2) is first N-alkylated with a propargyl derivative (3) to produce radical precursor (4). Radical precursor (4) then undergoes a radical cascade with arylisonitrile (5) to generate product (1). The N-alkylation proceeds smoothly following optimized conditions. See Curran, D. P. et al., *Tetrahedron Lett.*, 36, 8917 (1995), the disclosure of which is incorporated herein by reference. The synthesis of iodopyridone (2) and the conditions of the radical cascade have been previously reported. The propargylating agent (3) is readily prepared by the standard silylation of the dianion of propargyl alcohol with a suitable silylating agent $R^6R^7R^8$SiX followed by conversion of the propargyl alcohol to a leaving group such as a bromide, iodide or sulfonate. See Curran, D. P. et al., *Angew. Chem. Int. Ed. Engl.*, 34, 2683 (1995), the disclosure of which is incorporated herein by reference, and U.S. patent application Ser. No. 08,436,799, filed May 8, 1995, the disclosures of which are incorporated herein by reference.

Generally, various reagents can be used in the radical cascade including, but not limited to, hexamethylditin, hexamethyldisilane, or tetrakis(trimethylsilyl)silane. The source of energy for this reaction can be a sun lamp or an ultraviolet lamp. The temperature is preferably set between approximately 25 and 150° C. More preferably, the temperature is set at approximately 70° C. There are generally no limitations upon the choice of solvent used other than inertness to the radical cascade. Preferred solvents include benzene, toluene, acetonitrile, THF and tert-butanol. Also, there is very broad latitude in the choice of substituents on the alkyne and the isonitrile because of the mildness of the reaction conditions.

Figure 2:
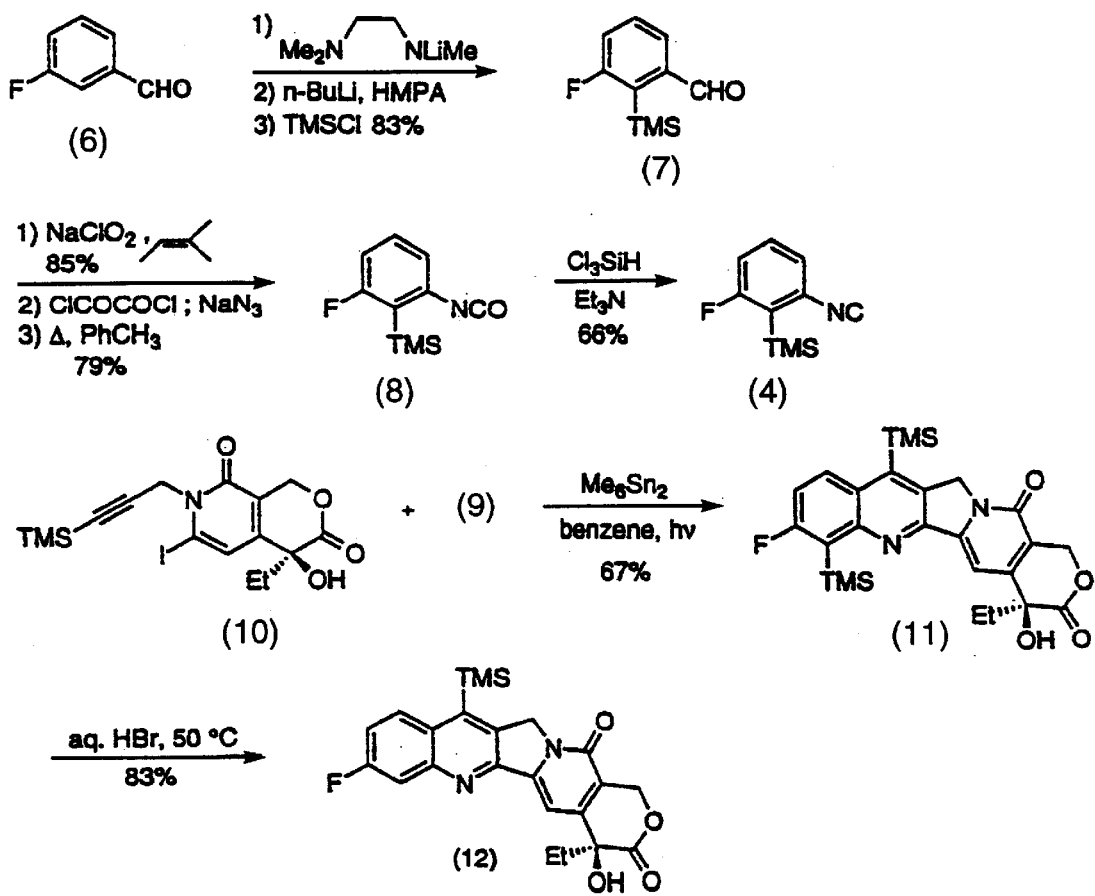
FIG. 2 is an illustration of a synthesis of (20S)-11-fluoro-7-trimethylsilylcamptothecin.

FIG. 2 illustrates an embodiment of a general synthetic scheme for the synthesis of (20S)-11-fluoro-7-trimethylsilylcamptothecin (12). A problem in this synthetic scheme is to control the regioselectivity of the radical cascade when both ortho positions in the arylisonitrile are available for cyclization (that is, $R^4$ is H in the final compound of formula (1)). One solution to this problem relies upon the introduction of a trimethylsilyl group on the aryl isonitrile, (e.g. 3-fluoro-2-trimethylsilylphenyl isonitrile (9)). The trimethylsilyl substituent blocks one of the ortho sites of the isonitrile toward cyclization and can be removed after the cascade reaction by hydrodesilylation. In this example, the selectivity proceeds further in the sense that only one of the trimethylsilyl groups is removed in the last step.

Other embodiments of the general synthetic scheme for the preparation of several novel camptothecin derivatives of formula (1) are illustrated in FIGS. 3 to 6, and in the Examples.

Figure 7:
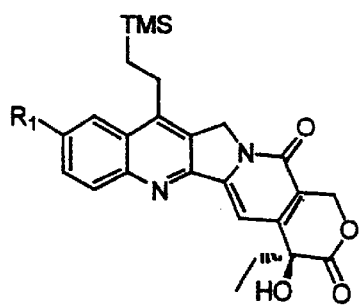
FIG. 7 is an illustration of three representative silylcamptothecin analogs of formula (2).

The preparation of the compounds of formula (2) is illustrated in FIGS. 7 through 11. In that regard, three representative, novel A,B ring substituted silylcamptothecin compounds (36a), (36b), and (36c) are illustrated in FIG. 7.

Figure 8:
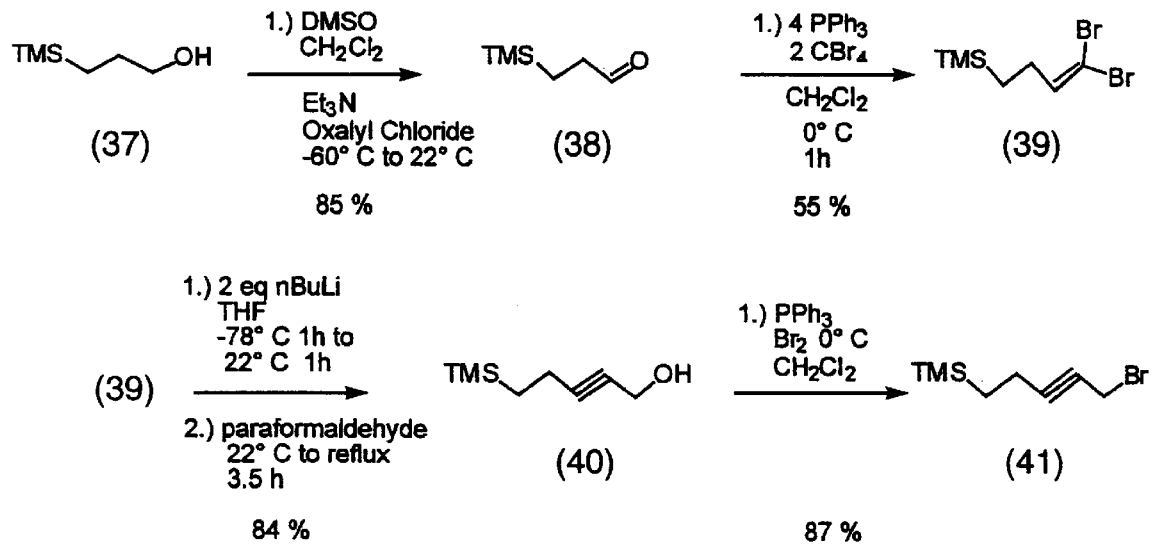
FIG. 8 is an illustration of the synthesis of a propargyl bromide precursor.

The first step in the synthesis of these analogs was to prepare propargyl bromide (41) as illustrated in FIG. 8. Swern oxidation of the commercially available trimethylsilylpropanol (37) gave trimethylsilylpropanal (38) in 85% yield. Sakar, T. K. et al., *Tetrahedron* 46, 1885 (1990). Following procedure A of Corey, E. J. and Fuchs, P. L., *Tetrahedron Lett.*, 36, 3769 (1972), aldehyde (38) was converted to the dibromoolefin (39) in 55% yield. Piers, E. and Gaval, A. V., *J. Org. Chein.*, 55, 2374 (1990). Addition of 2 equivalents of n-BuLi at −78° C. in THF followed by warming to 22° C. and the quenching with paraformaldehyde at reflux to give (40) in 84% yield. Finally, a solution of triphenylphosphine and Br$_2$ in anhydrous CH$_2$Cl$_2$ gave the propargyl bromide (41) in 87% yield.

Figure 9:
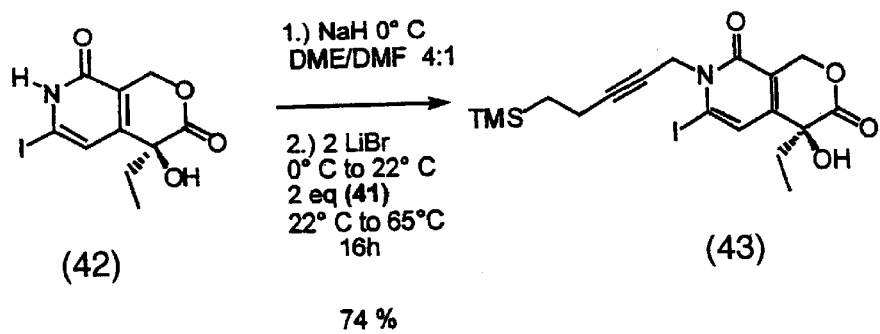
FIG. 9 is an illustration of the synthesis of a radical precursor of formula (3).
Figure 10:
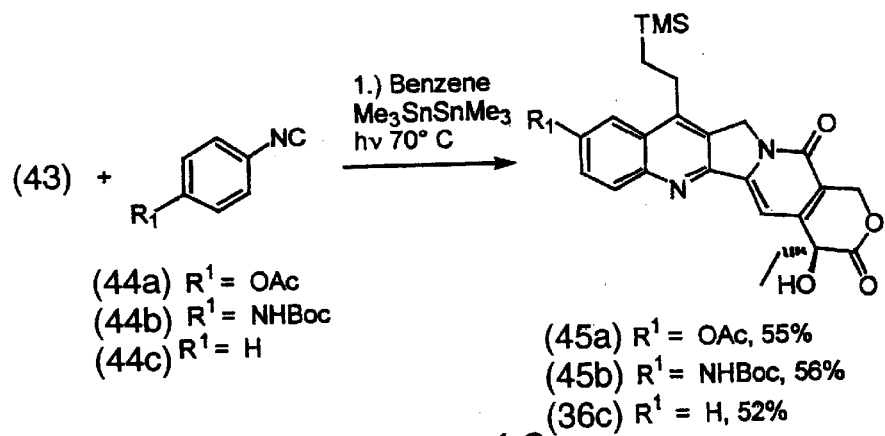
FIG. 10 is an illustration of the reaction of the radical precursor of FIG. 9 with three isonitriles.
Figure 11:
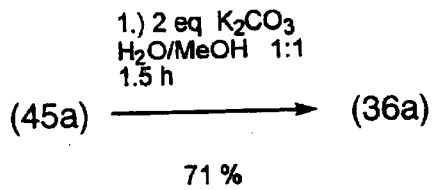
FIG. 11 is an illustration of the final step of the synthesis of the representative silylcamptothecin analogs of FIG. 7.
Figure 11:
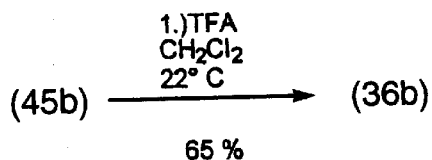

With the preparation of propargyl bromide (41) completed, radical precursor (43) was prepared as illustrated in FIG. 9. Following an N-alkylation procedure, (42) was alkylated with (41) to give the desired radical precursor (43) in 74% yield. Reaction of (43) with the respective isonitrile (44a) or (44b) gave the protected silylcamptothecin derivatives (45a) and (45b) in 55% and 56% yields, respectively, as illustrated in FIG. 10. Finally, deprotection of (45a) with 2 equivalents of K$_2$CO$_3$ in MeOH/H$_2$O solution gave a 47% yield of the 10-hydroxy derivative (36a) as illustrated in FIG. 10. Finally, treatment with trifluoroacetic acid in CH$_2$Cl$_2$ converted (45b) to the 10-amino derivative (36b) in 65% yield.

The method of the present invention also provides ready synthesis of (20S)-7-[(2-trimethylsilyl)ethyl]camptothecin (36c, FIG. 7). Reaction of phenyl isonitrile with iodo pyridone (43) gives this derivative in 52% yield (FIG. 10). The (20S)-7-[(2-trimethylsilyl)ethyl]camptothecin (36c) and (20S)-7-(2-trimethylsilyl)camptothecin (disclosed in U.S. patent application Ser. No. 08/436,799) structures have recently been described by Hausheer et al. in International Patent Application Publication Number WO 98/07727. It appears that the characterization information regarding these compounds set forth in International Patent Application Publication Number WO 98/07727 is not correct. Specifically, the spectroscopic data provided for both of these compounds are inconsistent with the assigned structures and do not match in any respect the spectroscopic data reported in the examples of this patent. Additionally, the spectroscopic data for all of the silyl-containing camptothecins in WO 98/07727 appear to be inconsistent with the assigned structures.

The present invention thus provides a short and efficient synthetic scheme well suited to known structure-activity relationships in the camptothecin family. Indeed, the biological activity of the camptothecin skeleton is generally intolerant or has very little tolerance to substituents other than at the 7 and/or 9–11 positions. Following synthesis, these substituents are introduced via the alkynylderivative (3) and arylisonitrile (5), respectively.

Antitumor Activities and Human Blood Stability Characteristics

The antitumor activities of several compounds of formula (1) are shown in Table 1 and compared to those of several well known camptothecin analogs using several known assays as described further below. The syntheses of the various exemplary compounds of the present invention set forth in Table 1 are discussed in further detail in an Example section following this section.

icity of the compounds toward HL-60 cells following 72 hr incubation was determined by XTT-microculture tetrazolium assay. Scudiero, D. A., et al., *Cancer Res.*, 48, 4827 (1988), the disclosure of which is incorporated herein by reference. 2', 3'-bis(-methoxy-4-nitro-5-sulfheny)-5-

TABLE 1

Biological Activities of (20S)-7-Silyl-Camptothecin Derivatives.

| Ex. | 7[a] | 9 | 10 | 11 | 12 | Inhibition of cancer cell growth $IC_{50}$ (NM) HL-60 | | 833K | DC-3F | Enhancement of Topo I Mediated DNA Cleavage | Inhibition of Topo I mediated DNA relaxation |
|---|---|---|---|---|---|---|---|---|---|---|---|
| CPT | H | H | H | H | H | 5 | | 10 | 6–9 | +++ | +++ |
| IRT | Et | H | OPP[a] | H | H | 270 | | 487 | 372 | — | — |
| 1 | TMS | H | H | H | H | 3.8 | | 5.6 | 4.2 | ++++ | +++ |
| 2 | TBDMS | H | H | H | H | 0.12 | | 1.2 | 2.9 | ++++ | +++ |
| 3 | TBDPS | H | H | H | H | 339 | | 243 | 663 | ++ | + |
| 4 | TMS | H | OAc | H | H | 2.7 | | | 6.7 | ++++ | +++++ |
| 5 | TMS | H | OH | H | H | 2.6 | | 7.0 | 6.9 | ++++ | +++++ |
| 5a | Example 5 with opened E ring | | | | | 9.7 | | 15.0 | 14.2 | +++ | + |
| 6 | TMS | H | OPP[a] | H | H | 66 | | 214 | 256 | — | — |
| 7 | TMS | H | H | F | H | 0.75 | | 0.92 | 2.0 | ++++ | +++++ |
| 7a | TMS | F | H | H | H | 3.0 | | 2.9 | 8.2 | ++++ | ++++ |
|  | TMS | H | H | F | H (2:1) | | | | | | |
| 8 | TMS | H | $NH_2$ | H | H | 0.52 | | 5.7 | 0.72 | — | — |
| 9 | TMS | H | H | $NH_2$ | H | 2.6 | | 7.4 | 6.4 | — | — |
| 10 | TMS | H | $NH_2$ | F | H | 0.07 | | 0.14 | 0.29 | ++++ | ++++ |
| 11 | TMS | H | H | F | F | 1.01 | | 2.1 | 2.5 | +++ | +++ |
|  | TMS | F | F | H | H (3/1) | | | | | | |
| 12 | TIPS | H | H | H | H | 1506 | | 10730 | 1038 | — | — |
| 13 | TES | H | H | H | H | 31.9 | | 122 | 57.1 | — | — |
| 14 | DMNPS | H | H | H | H | 66.9 | | 197 | 64.1 | — | — |
| 15 | DMCPS | H | H | H | H | 0.91 | | 2.7 | 2.7 | — | — |
| 16 | DMHPS | H | H | H | H | 2.1 | | 5.4 | 2.3 | — | — |
| 17 | TBDMS | H | OAc | H | H | 1.86 | | — | 3.57 | — | — |
| 18 | TBDMS | H | OH | H | H | 2.60 | | — | 5.20 | — | — |

[a]OPP = irinotecan's pyrrolidinyl pyrrolidine carbamate;
TMS = trimethylsilyl;
TBDMS = t-butyldimethylsilyl;
TBDPS = t-butyldiphenyl silyl;
TES = triethylsilyl;
TIPS = triisopropylsilyl;
DMNPS = dimethylnorpinylsilyl;
DMCPS = dimethyl-3-cyanopropylsilyl;
DMHPS = dimethyl-3-halopropylsilyl;
[b]More active than CPT in S-180 in $BD_2F_1$ mice testing.
[c]More active than CPT in Lewis lung Carcinoma in $BD_2F1$ mice. The designation "—" means "not determined."

As illustrated in Table 1, the compounds of the present invention exhibit good to excellent antitumor activity as compared to camptothecin (CPT) and irinotecan (IRT).

Cytotoxicity Assays

The camptothecin derivatives were evaluated for their cytotoxic effects on the growth of HL-60 (human promyelocytic leukemic), 833K (human teratocarcinoma) and DC-3F (hamster lung) cells in vitro. The cells were cultured in an initial density of $5\times10^{-4}$ cell/ml. They were maintained in a 5% $CO_2$ humidified atmosphere at 37° C. in RPMI-1640 media (GIBCO-BRL Grand Island, N.Y.) containing penicillin 100 μ/ml)/streptomycin (100 "g/ml) (GIBCO-BRL) and 10% heat inactivated fetal bovine serum. The assay was performed in duplicate in 96-well microplates. The cytotox-

[(phenylamino)carbonyl]-2H-tetrazolium hydroxide (XTT) was prepared at 1 mg/ml in prewarmed (37° C.) medium without serum. Phenazine methosulfate (PMS) and fresh XTT were mixed together to obtain 0.075 mM PMS-XTT solution (25 "l of the stock 5 mM PMS was added per 5 ml of 1 mg/ml XTT). Fifty "l of this mixture was added to each well of the cell culture at the end of 72 hr incubation. After incubation at 37° C. for 4 hr., absorbance at 450 nm and 630 nm was measured with a microplate reader (EL340, Bio-Tek Instruments, Inc., Winooski, Vt.).

The cytotoxicity of the camptothecin compounds toward 833K teratocarcinoma solid tumor cells and DC-3F hamster lung cells was determined in 96-well microplates by a method described by Skehan et al. for measuring cellular protein content. Skehan et al., "New Colorometric Cytotoxicity Assay for Anticancer Drug Screening," *J. Nat'l Cancer*

Inst., 82, 1107 (1990), the disclosure of which is incorporated herein by reference. Cultures were fixed with trichloroacetic acid and then stained for 30 minutes with 0.4% sulforhodamine B dissolved in 1% acetic acid. Unbound dye was removed by acetic acid washes, and the protein-bound dye was extracted with an unbuffered Tris base [tris (hydroxy-methyl)aminomethan] for determination of absorbance at 570 nm in a 96-well microplate reader. The experiments were carried out in duplicate using five to six concentrations of the drugs tested. Data were analyzed via computer software. See, Chou, J, and Chou, T. C., *Dose-Effect Analysis With Microcomputers: Quantitation of $ED_{50}$, $LD_{50}$, Synergism, Antagonism, Low-Dose Risk, Receptor-Ligand Binding and Enzyme Kinetics*, $2^{nd}$ ed., Biosoft, Cambridge (1987); and Chou, T. C., "The Median-Effect Principle and the Combination Index for Quantitation of Synergism and Antagonism," *Synergism and Antagonism in Chemotherapy*, Academic Press, San Diego, 61–102 (1991), the disclosures of which are incorporated herein by reference.

Topo I Mediated DNA Cleavage Assay

For DNA cleavage assay the reaction mixture comprised Tris-HCl buffer 10 mM, pH7.5; $PBR_{322}$ supercoiled double stranded circular DNA (4363 base pairs, from Bochringer Mannheim Biochemicals) 0.125 $\mu$g/ml, drug (camptothecin or its derivatives) concentration at 1, 10 and 100 $\mu$M, in the presence of purified DNA topoisomerase I with final volume of 20 $\mu$l as described previously. Hsiang, Y. H., et al., "Camptothecin Induces Protein-Linked DNA Breaks Via Mammalian DNA Topoisomerase I," *J. Biol. Chem.*, 260, 14873 (1985), the disclosure of which is incorporated herein by reference. Incubation was carried out at 37° C. for 60 min. The reaction was stopped by adding the loading buffer dye (2% sodium dodesyl sulfate, 0.05% bromophenol blue and 6% glycerol). Electrophoresis was carried cut on 1% agarose gel plus ethidium bromide (1 $\mu$g/ml) in TBE buffer (Tris-base-boric acid-EDTA) and ran at 25 V for 18 hrs. Photographs were taken under UV light using Polaroid film type 55/N and developed as indicated by the manufacturer.

Inhibition of Topo I Mediated Relaxation of Supercoiled DNA

To study the inhibiting effect on DNA topoisomerase I mediated relaxatioon of DNA, the method described by Liu and Miller was used. Liu, H. F. et al., "Cleavage of DNA by Mammalian DNA Topoisomerase II," *J. Biol. Chem.*, 258, 15365 (1980), the disclosure of which is incorporated herein by reference. For this assay, 0.18 $\mu$g of $PBR_{322}$ DNA, 0.5 U of Topo I (GIBCO-BRL), various concentrations (1–100 $\mu$M) of camptothecin or an analog, in a reaction mixture (20 $\mu$l) containing 50 mM Tris-HCl, pH 7.5, 120 mM KCl, 10 mM $MgCl_2$, 0.5 mM DTT, 0.5 mM EDTA, 30 $\mu$g/ml BSA, 20 $\mu$g/ml $PBR_{322}$ DNA and various amounts of the enzyme was incubated at 37° C. for 30 min., and stopped with 5% SBS and 150 $\mu$g/ml proteinase K. The samples were loaded onto 1% agarose in TAE running buffer, electrophoresed overnight at 39 V, stained with EtBr, and photographed under UV light.

Antitumor Activity in vivo

Antitumor activities of camptothecin derivatives were tested in $B_6D_2F_1$ mice bearing sarcoma-180 or Lewis lung murine solid tumor. For S-180, $3\times10^6$ cells were innoculated subcutaneously on day 3. Antitumor treatment started on day 1 intraperitoneously twice daily for five days. Tumor volumes on day 7 and day 14 were measured. Average tumor volumes were described as the ratio of treated versus untreated control (T/C). The control (treated with DMSO vehicle only) tumor volumes for day 7 and day 14 were 0.11 $cm^3$ and 0.61 $cm^3$, respectively. The T/C camptothecin is designated with "+++." An increment or decrement of 10% as compared to the camptothecin T/C on day 14 at 2 mg/kg dosage is designated with increase or decrease of one "+" unit, respectively.

For Lewis lung carcinoma, tumor cells ($1\times10^6$) were inoculated subcutaneously on day 0 and treatment started on day 1, intraperitoneously twice daily for five days. The grading of effects was as described above.

As shown Table 1, many of the camptothecin derivatives of formula (1) tested for the antitumor cytotoxicity in vitro exhibited higher potency than camptothecin in one to three cell lines. Most of those compounds exhibiting higher antitumor cytotoxicity also exhibited higher potency in enhancing the DNA-topoisomerase I-mediated cleavage of $PBR_{322}$ DNA, or in inhibiting the DNA-topoisomerase I-mediated relaxation of $PBR_{322}$ DNA. These results suggest excellent correlation between the antitumor cytotoxicity of the camptothecin compounds with their ability to inhibit the functions of DNA-topoisomerase I.

For in vivo chemotherapeutic effects in tumor-bearing mice, for example, 7-trimethylsilyl camptothecin showed better activity than camptothecin against sarcoma 180 in $B_6D_2F_1$ mice at several equivalent doses in a dose dependent manner in terms of tumor volume reduction. Similarly, for Lewis lung carcinoma, 7-trimethylsilyl-11-flouro camptothecin exhibited a similar antitumor effect to camptothecin in terms of tumor volume reduction at 4-fold lower doses than camptothecin. Thus, 7-trimethylsilyl-11-flouro camptothecin is more efficacious than camptothecin in its antitumor effects in vivo.

Stability in Human Blood

Recently the intrinsic fluorescent emissions from the lactone and carboxylate forms of camptothecin have been studied to elucidate their markedly different interactions with human blood components. Burke, T. G. and Mi, Z., "Ethyl substitution at the 7 position extends the half-life of 10-hydroxycamptothecin in the presence of human serum albumin," *J. Med. Chem.* 36: 2580–2582 (1993); Burke, T. G., Mishra, A. K., Wani, M. C. and Wall, M. E., "Lipid bilayer partitioning and stability of camptothecin drugs," *Biochemistry.* 32: 5352–5364 (1993); Burke, T. G. and Mi, Z.: "Preferential Binding of the Carboxylate Form of Camptothecin by Human Serum Albumin," (1993) *Anal. Biochem.* 212, 285–287; Burke, T. G. and Mi, Z., "The Structural Basis of Camptothecin Interactions with Human Serum Albumin: Impact on Drug Stability," (1994) *J. Med. Chem.* 37, 40–46; Burke, T. G. Munshi, C. B., Mi, Z., and Jiang, Y., "The Important Role of Albumin in Determining the Relative Human Blood Stabilities of the Camptothecin Anticancer Drugs," (1995) *J. Pharma. Sci.* 84, 518–519; Mi, Z. and Burke, T. G., "Differential Interactions of Camptothecin Lactone and Carboxylate Forms with Human Blood Components," (1994) *Biochemistry*, 33, 10325–10336; Mi, Z. and-Burke, T. G., "Marked Interspecies Variations Concerning the Interactions of Camptothecin with Serum Albumins: A Frequency-Domain Fluorescence Spectroscopic Study," (1994) *Biochemistry* 33, 12540–12545; Mi, Z., Malak, H., and Burke, T. G., "Reduced Albumin Binding Promotes the Stability and Activity of Topotecan in Human Blood," (1995) *Biochemistry*, 34, 13722–13728, the disclosures of which are incorporated herein by reference.

In phosphate buffered saline (PBS) at pH 7.4, frequency-domain fluorescence lifetime spectroscopy reveals that human serum albumin (HSA) preferentially binds the carboxylate form of camptothecin with a 200-fold higher affinity than the lactone form. These interactions result in camptothecin opening more rapidly and completely in the presence of HSA than in the absence of the protein. In human plasma, pH 7.4 and 37° C., camptothecin lactone opens rapidly and completely to the carboxylate form with a $t_{1/2}$ value of 11 min and an almost negligible % lactone at equilibrium value of 0.2%. In whole blood versus plasma, camptothecin displayed enhanced stability ($t_{1/2}$ value of 22 min and a % lactone at equilibrium value of 5.3%). The enhanced stability of camptothecin lactone in human blood was found to be due to drug associations with the lipid bilayers of red blood cells. Camptothecin binds erythrocyte membranes, the drug localizes within the acyl chain region, and accordingly remains protected from hydrolysis.

The human blood stabilities of the several camptothecin analogues of clinical interest have been compared. As was observed in the case of camptothecin, 9-aminocamptothecin was observed to hydrolyze almost completely (>97%) in PBS solution containing HSA. Although no attempt was made to spectroscopically quantify the relative binding affinities of the lactone and carboxylate forms of the 9-amino congener due to their significantly reduced fluorescence quantum yields relative to camptothecin, HPLC data were consistent with HSA preferentially binding the carboxylate form of this agent over its lactone form. In plasma it was observed that >99.5% of the 9-amino analog converted to carboxylate, a finding which again closely parallels stability data obtained using camptothecin. In whole blood, <0.5% and 5.3% are the fractions of 9-aminocamptothecin and camptothecin, respectively, which remained in the lactone form at equilibrium. The approximately 10-fold higher level of lactone remaining at equilibrium for camptothecin relative to 9-aminocamptothecin may, in part, be accounted for by the enhanced lipophilicity and greater ability of camptothecin to transition from the aqueous environment and into erythrocyte membranes present in whole blood.

In stark contrast to the low levels of lactone remaining at equilibrium in whole human blood for camptothecin and 9-aminocamptothecin (<0.5% and 5.3%, respectively), topotecan (11.9%), CPT-11 (21.0%), and SN-38 (19.5%) all display improved blood stabilities. While lactone levels at equilibrium for topotecan are 20-fold greater than for 9-aminocamptothecin, the corresponding levels of lactone for IRT (CPT-11) and 10-hydroxy-7-ethylcamptothecin (SN-38) are approximately 40-fold greater than in the case of 9-aminocamptothecin. The significant gains in the relative stabilities of topotecan, CPT-11, and SN-38 can be correlated to their favorable interactions with HSA. These agents contain structural substituents at the 7- and 9-positions which hinder and prevent the preferential binding of the carboxylate drug forms by HSA. The technique of time-resolved fluorescence anisotropy has recently been used to demonstrate that, under experimental conditions where camptothecin carboxylate associates with HSA and tumbles in solution closely associated with the protein, the carboxylate forms of topotecan and CPT-11 do not associate with HAS. In the case of SN-38, direct spectroscopic evidence has been obtained which indicates that HSA preferentially binds the lactone form of this agent, thereby shifting the lactone-carboxylate equilibrium to the lactone.

Thus, it is clear from these observations that HSA plays an important role in determining the relative human blood stabilities of the camptothecins. In the cases of camptothecin and 9-aminocamptothecin, the protein acts as a sink for the carboxylate drug form, binding the opened ring species and thereby shifting the lactone-carboxylate equilibria to the carboxylate. However, in the cases of topotecan, CPT-11, and SN-38, no such preferential binding of the carboxylate drug form by HSA is observed. Opposite to the situation with camptothecin and its 9-amino analogue, HSA preferentially binds the lactone form of SN-38 which thereby promotes higher circulatory levels of this biologically active species.

The rapid and extensive loss of active drug that occurs with currently clinically relevant camptothecins indicates that it would be highly advantageous to identify camptothecins with reduced protein binding interactions and improved human blood stabilities. In that regard, the camptothecin analogs of the present invention exhibit unique properties that result in the agents displaying improved human blood stabilities while maintaining high anticancer activities.

Experimental Methods for the Determination of Lipid Bilayer Partitioning (i.e. Lipophilicity) and Lactone Ring Stability Chemicals. All camptothecin analogs were in the 20(S) configuration and were of high purity (>98%) as determined by HPLC assays with fluorescence detection. All other agents were reagent grade and were used without further purification. High purity water provided by a Milli-Q UV PLUS purification system (Bedford, Mass.) was utilized in all experiments.

Drug Stock Solution Preparation. Stock solutions of the drugs were prepared in dimethylsulfoxide (A.C.S. spectrophotometric grade, Aldrich, Milwaukee, Wis.) at a concentration of $2 \times 10^{-3}$ M and stored in dark at 4° C. L-α-Dimyristoylphosphatidylcholine (DMPC) and L-α-dimyristoylphosphatidylglycerol (DMPG) were obtained from Avanti Polar Lipids, Alabaster, Ala., and were used without further purification. All other chemicals were reagent grade and were used without further purification.

Vesicle Preparation. Small unilamellar vesicle (SUV) suspensions were prepared the day of an experiment by the method of Burke and Tritton, "The Structure Basis of Anthracycline Selectivity for Unilamellar Phophatidylcholine Vesicles: An Equilibrium Binoinl Study," *Biochem* 24:1768–1776 (1985). Briefly, stock lipid suspensions containing 200 mg/mL lipid in phosphate buffered saline (PBS, pH 7.4) were prepared by Vortex mixing for 5–10 min above the $T_M$ of the lipid. The lipid dispersions were then sonicated using a bath-type sonicator (Laboratory Supplies Co., Hicksville, N.Y.) for 3–4 h until they became optically clear. A decrease in pH from 7.4 to 6.8 was observed for the SUV preparations of DMPG; therefore, the pH of these SUV suspensions was adjusted to 7.4 using small quantities of 2.5 M NaOH in PBS, followed by additional sonication. Each type of vesicle suspension was annealed for 30 min at 37° C. and then used in an experiment.

Fluorescence Instrumentation. Steady-state fluorescence measurements were obtained on a SLM Model 9850 spectrofluorometer with a thermostated cuvette compartment. This instrument was interfaced with an IBM PS/2 model 55 SX computer. Excitation and emission spectra were recorded with an excitation resolution of 8 nm and an emission resolution of 4 nm. In all cases spectra were corrected for background fluorescence and scatter from unlabeled lipids or from solvents by subtraction of the spectrum of a blank. Steady-state fluorescence intensity measurements were made in the absence of polarizers. Steady-state anisotropy (a) measurements were determined with the instrument in the "T-format" for simultaneous measurement of two polarized intensities. The alignment of polarizers was checked routinely using a dilute suspension of 0.25 "m polystyrene microspheres (Polysciences, Inc, Warrington, Pa.) in water and anisotropy values of >0.99 were obtained. Alternatively, polarizer orientation was checked using a dilute solution of glycogen in water. The anisotropy was calculated from $a=(I_{VV}-GI_{VH})/(I_{VV}+GI_{VH})$, where $G=I_{VH}/I_{HH}$ and the subscripts refer to vertical and horizontal orientations of the excitation and emission polarizers, respectively.

Anisotropy measurements for camptothecins were conducted using exciting light of 370 nm and long pass filters on each emission channel in order to isolate the drug's fluorescence signal from background scatter and/or residual fluorescence. All emission filters were obtained from Oriel Corp (Stamford, Conn.). The combination of exciting light and emission filters allowed adequate separation of fluorescence from background signal. The contribution of background fluorescence, together with scattered light, was typically less than 1% of the total intensity. Since the lactone rings of camptothecin and related congeners undergo hydrolysis in aqueous medium with half-lives of approximately 20 min., all measurements were completed within the shortest possible time (ca. 0.5 to 1 min) after mixing the drug stock solution with thermally pre-equilibrated solutions such that the experiments were free of hydrolysis product.

Determination of Equilibrium Binding Constants. The method of fluorescence anisotropy titration reported in Burke, T. G., Mishra, A. K., Wani, M. C. and Wall, M. E. "Lipid bilayer partitioning and stability of camptothecin drugs," *Biochemistry*. 32: 5352–5364 (1993) was employed to determine the concentrations of free and bound species of drug in liposome suspensions containing a total drug concentration of $1 \times 10^{-6}$ M and varying lipid concentrations. All experiments were conducted in glass tubes. The overall association constants are defined as $K=[A_B]/[A_F][L]$ where $[A_B]$ represents the concentration of bound drug, $[A_F]$ represents the concentration of free drug, and $[L]$ represents the total lipid concentration of the sample. Double-reciprocal plots of the binding isotherms {1/(bound fraction of drug) vs. 1/[lipid]} were linear and K values were determined from their slopes by the method of linear least squares analysis. A computer program based on the $K=[A_B]/[A_F][L]$ relationship was written to predict bound drug levels for specified values of K and total drug.

Kinetics of Lactone Ring Opening. The hydrolysis kinetics of camptothecins in the presence of different blood components were determined by a quantitative C18 reversed-phase high-performance liquid chromatography (HPLC) assay as described in the literature. Mi and Burke (1994), supra. The preparation of whole blood and fractionated blood samples was carried out as described previously. Crystallized HSA of high purity (>97%) from Sigma Chemical (St. Louis, Mo.) was used. HSA stock solutions were prepared in PBS buffer with a final pH of 7.40±0.05. HSA concentrations were determined by UV absorbance at 278 nm using an extinction coefficient of 39,800 $M^{-1}cm^{-1}$ (Porter, 1992). All other agents were reagent grade and were used without further purification. High purity water provided by a Milli-Q UV PLUS purification system (Bedford, Mass.) was utilized in all experiments.

Anticancer Activities of Highly Lipophilic Camptothecins of the Present Invention Determined In Vitro in Cell Culture Experiments Cells. Cytotoxicity measurements were conducted using MDA-MB-435 tumorigenic human breast cancer cells. The cells were exposed to a range of drug concentrations for 72 hr exposure periods and then viability was assessed using a sulphorrhodamine B (SRB) assay. SRB assays were performed using a standard assay.

Figure 12:
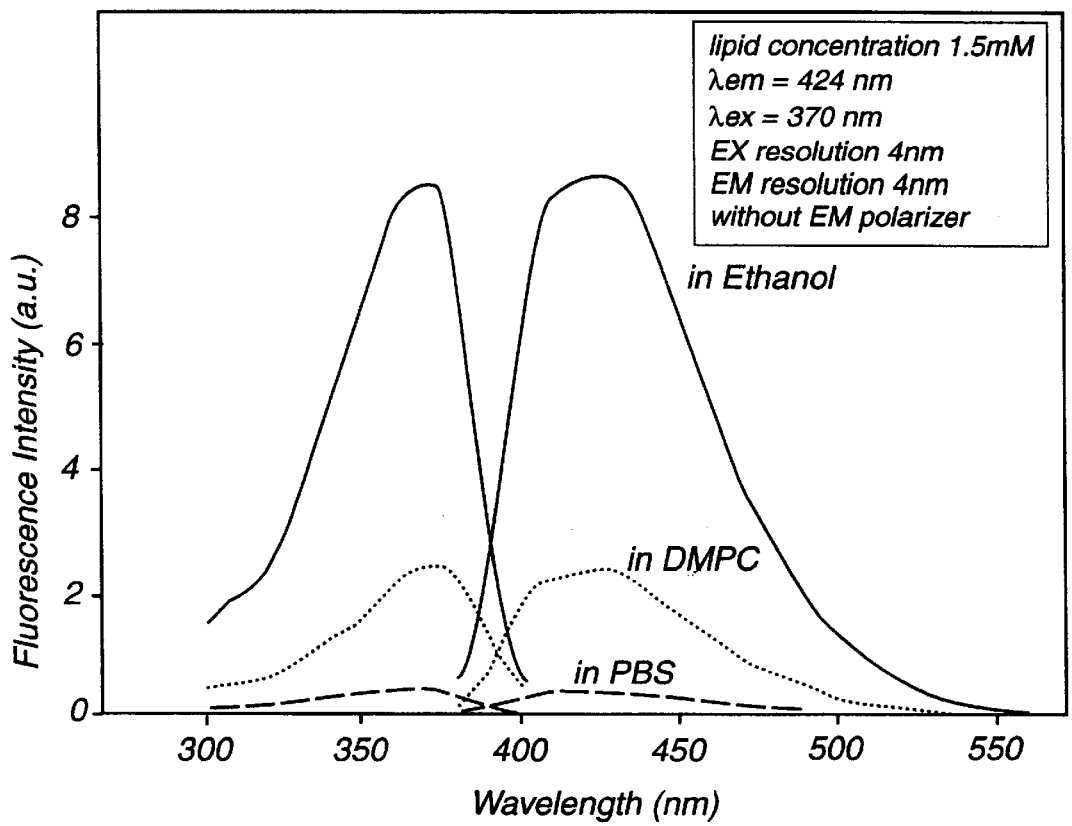
FIG. 12 is an illustration of excitation and emission fluorescence spectra of 1 $\mu$M (20S)-7-[(2-trimethylsilyl)ethyl]camptothecin, 7-TMSEt CPT, (36c) (DB-172).
Figure 13:
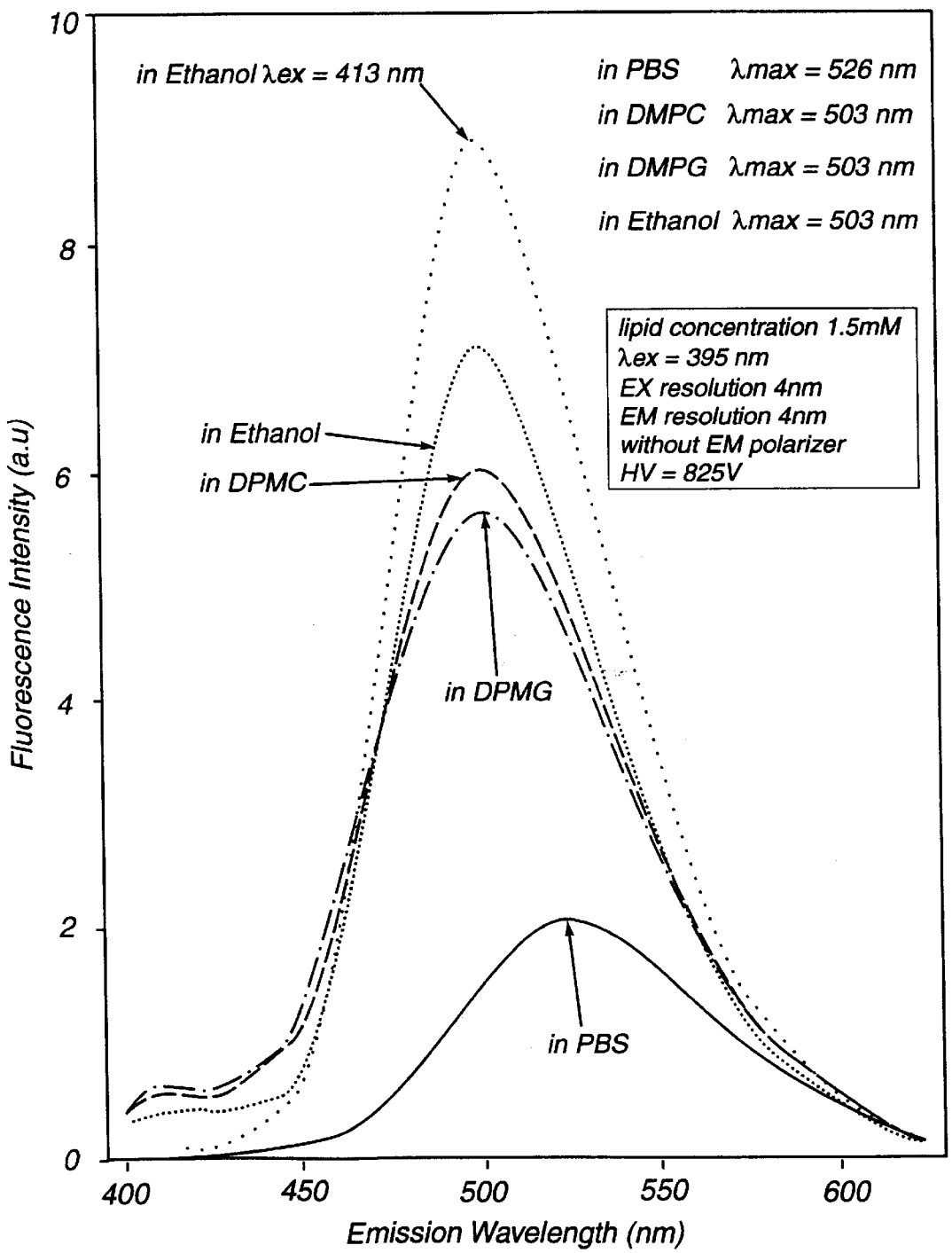
FIG. 13 is an illustration of emission fluorescence spectra of 1 $\mu$M (20S)-10-amino-7-[(2-trimethylsilyl)ethyl]camptothecin, 10-NH2-7-TMSEt CPT (DB-173).
Figure 14:
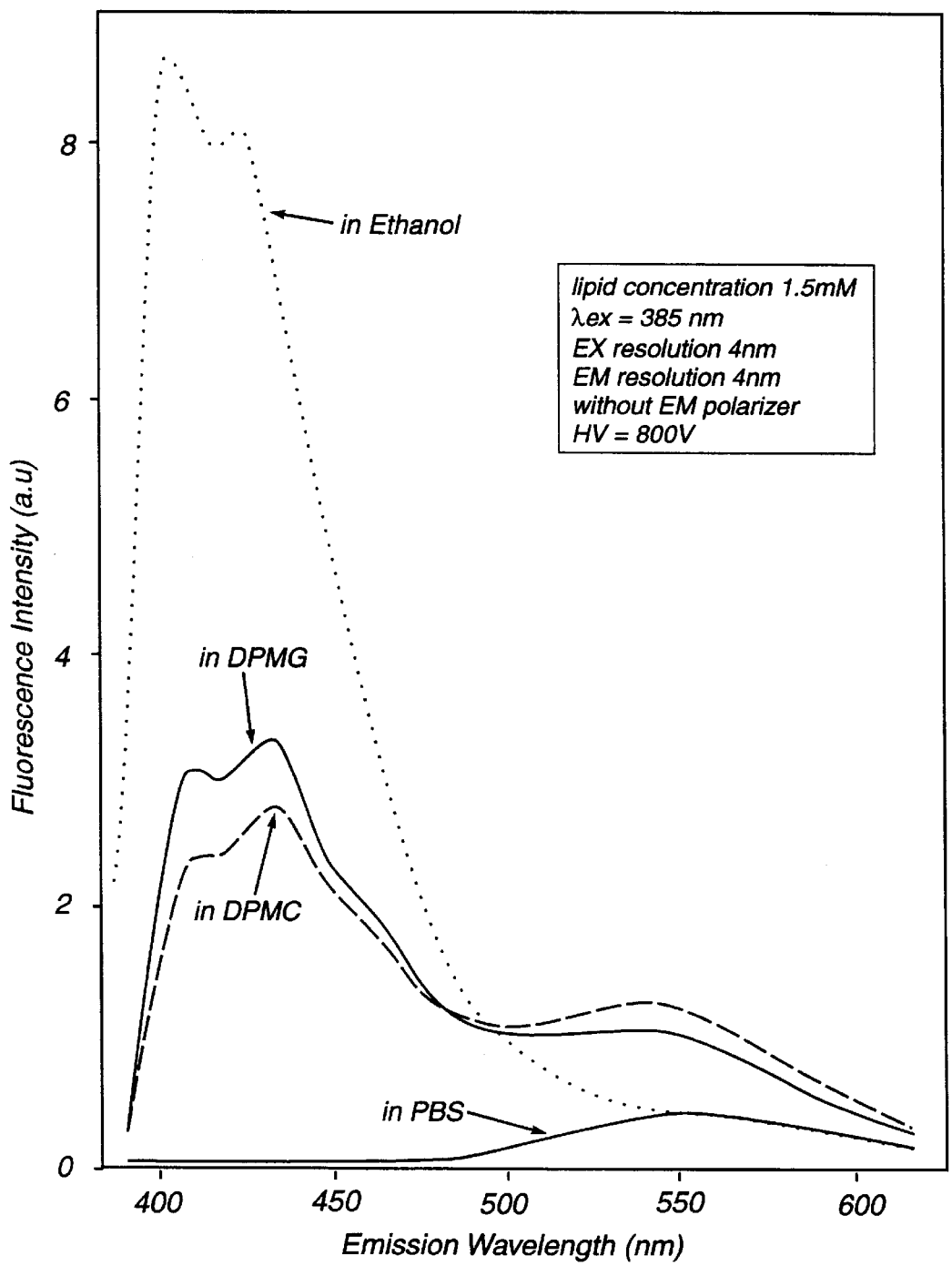
FIG. 14 is an illustration of emission fluorescence spectra of 1 $\mu$M (20S)-10-hydroxy-7-[(2-trimethylsilyl)ethyl]camptothecin, 10-OH-7-TMSEt CPT (DB-174).
Figure 15:
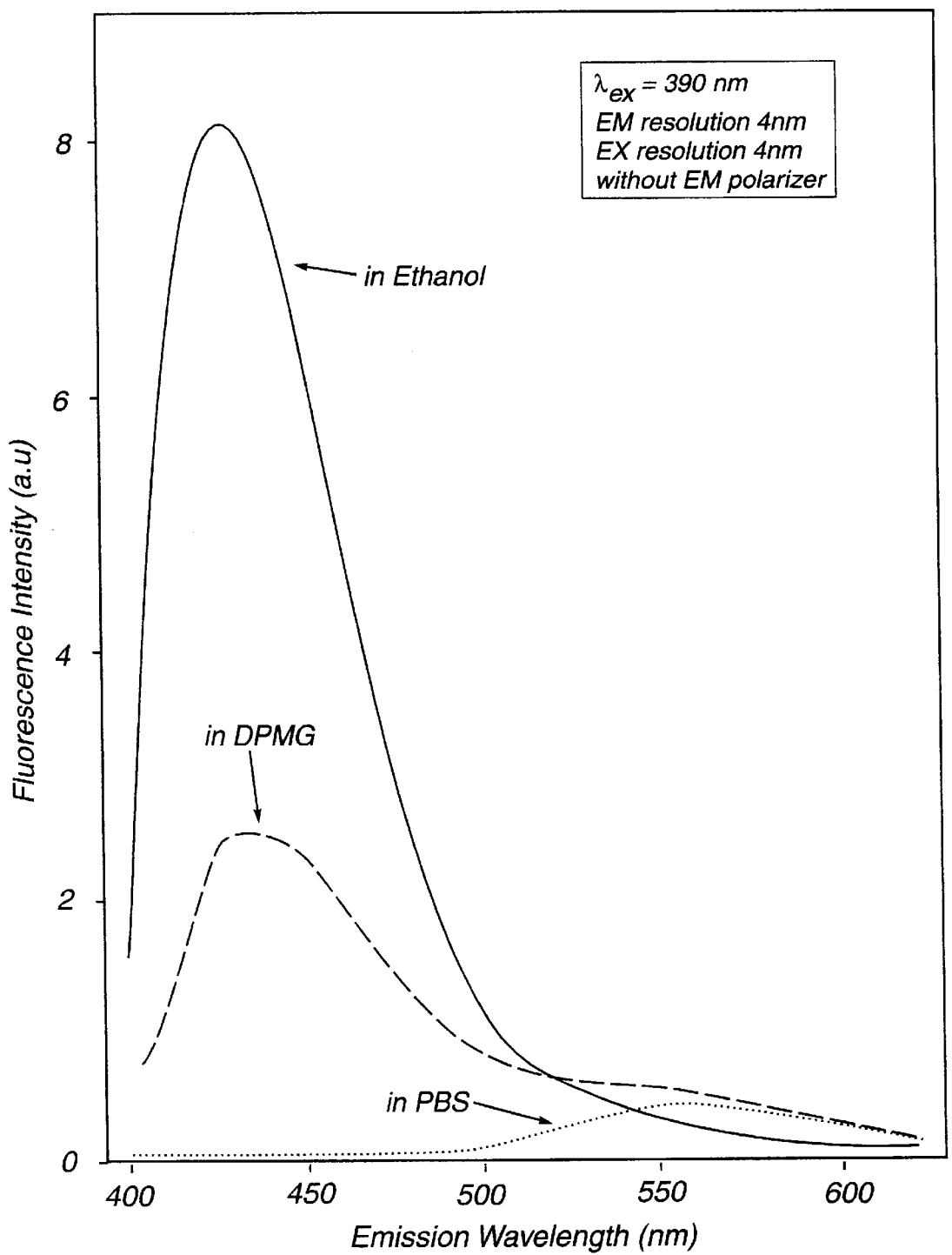
FIG. 15 is an illustration of fluorescence spectra of 1 $\mu$M (20S)-10-hydroxy-7(tert-butyldimethylsilyl)camptothecin, 10-OH-7-TBS CPT (DB-67) in ethanol, 0.29 M DMPG and PBS.

Fluorescence Anisotropy Titration Demonstrates that the Camptothecin Analogs of the Present Invention Display Exceptionally High Equilibrium Association Constants for Lipid Vesicles FIGS. 12 through 15 depict the fluorescence excitation and emission spectra of several of the new camptothecin analogs. FIG. 12 summarizes the excitation and emission spectra of 1 "M DB-172 in phosphate buffered saline solution. The figure indicates that upon introduction of lipid bilayers into the sample there is an increase in the fluorescence emission of the compound, indicative of an interaction between the drug and the membrane. Upon changing the solvent to ethanol the fluorescence also changes. FIGS. 13 through 15 summarize the emission spectra of DB-173, DB-174, and DB-67, respectively, in the presence and absence of membranes. In each case there is a marked increase in fluorescence intensity as the drug partitions into the lipid bilayer. In each case there is also a prominent blue-shifting or shift in the emission spectra to lower wavelength upon drug interaction with membrane. The spectral data presented in FIGS. 12 through 15 clearly indicate that the new agents are fluorescent and the spectral parameters of the drugs change upon addition of lipid bilayer membranes to the samples. Table 2 compares the maximum excitation and emission wavelengths of new campothecin analogs with congeners that have been made previously. The intrinsic fluorescent nature of the camptothecins allows for the sensitive method of steady-state fluorescence anisotropy titration to be employed to determine the strength of the binding interactions of the various analogs with lipid bilayers.

TABLE 2

Fluorescence Spectral Parameters for camptothecin analogs in solution and bound to DMPC and DMPG SUVs.

| Compound (S) | Excitation (nm) PBS | Emission (nm) PBS | Emission (nm) DMPC | Emission (nm) DMPG |
|---|---|---|---|---|
| camptothecin | 367 | 430 | 422 | 415 |
| 7-methylcamptothecin | 366 | 421 | 418 | 405 |
| 7-ethylcamptothecin | 367 | 422 | 419 | 406 |
| 7-propylcamptothecin | 366 | 422 | 419 | 406 |
| 7-methyl-10-ethoxycamptothecin | 376 | 430 | 401 | 400 |
| 7-ethyl-10-methoxycamptothecin | 376 | 430 | 403 | 406 |
| 7-propyl-10-methoxycamptothecin | 376 | 430 | 404 | 404 |
| DB-67 | 400 | 550 | 445 | 440 |
| DB-172 | 370 | 424 | 424 | 422 |
| DB-173 | 395 | 526 | 503 | 502 |
| DB-174 | 380 | 550 | 433 | 431 |
| DB-202 | 377 | 450 | 439 | 437 |
| CHJ-792 | 400 | 531 | 517 | 519 |

The following designations are used herein: DB-172, (20S)-7-[(2-trimethylsilyl)ethyl]camptothecin (36c); DB-173, (20S)-10-amino-7-[(2-trimethylsilyl)ethyl] camptothecin (36b); DB-174, (20S)-10-hydroxy-7-[(2-trimethylsilyl)ethyl] camptothecin (36a); DB-67, (20S)-10-hydroxy-7(tert-butyldimethylsilyl)camptothecin; DB-148, (20S)-7-(3-chloropropyldimethylsilyl)camptothecin; DB-158, (20S)-10-hydroxy-7-(3-chloropropyldimethylsilyl) camptothecin; DB-202, (20S)-7(tert-butyldimethylsilyl) camptothecin; CHJ-792, 10-amino-7-trimethylsilylcamptothecin (20); DB-124, 10-hydroxy-7-(3-dimethylaminopropyldimethylsilyl) camptothecin hydrochloride salt; and DB-104, 7-(3-dimethylaminopropyldimethylsilyl) camptothecin hydrochloride salt.

A steady-state fluorescence anisotropy (a) measurement is related to the rotational rate of the fluorescent molecule through the Perrin Equation:

$$a_o/a = 1 + (\tau/\Phi)$$

where $a_o$ is the limiting fluorescence anisotropy in the absence of depolarizing rotations, $\tau$ is the excited-state lifetime, and $\Phi$ is the rotational correlation time of the fluorophore. The above equation states that changes in either the $\tau$ or $\Phi$ values of a fluorescent compound can modulate its steady-state anisotropy.

The excited-state lifetime values of camptothecin in PBS, glycerol, and methanol were examined at 37° C. The lifetime values were determined to be 4.7 ns, 3.8 ns, and 3.5 ns, respectively. Similarly, camptothecin's lifetime value when associated with DMPC bilayers were measured at 37° C., and the average value for membrane-bound drug was found to be 3.7 ns.

Thus the lifetime measurements described above indicate that camptothecin's excited-state lifetime is relatively insensitive to alterations in microenvironment (e.g. a change in solvent or fluorophore relocation from an aqueous milieu to a phospholipid membrane). For a fluorophore whose $\tau$ value remains relatively constant during a transition which strongly impacts on its rotational motion (such as a change in solvent viscosity or fluorophore binding to large macromolecular assemblies such as liposomal particles), the Perrin equation indicates a direct relationship between a and $\Phi$ values will exist (that is, as the $\Phi$ value of the fluorescent compound increases, then so too does its steady-state anisotropy value).

Steady-state fluorescence anisotropy values of the camptothecin analogues are highly sensitive to solvent viscosity and to associations with small unilamellar lipid vesicles. For example, topotecan has an a value of 0.008 in PBS, but its a value increases 9-fold and 40-fold in the viscous solvents octanol and glycerol, respectively. A 21-fold enhancement in the a value of camptothecin is observed upon binding of drug to vesicles composed of either DMPC or DMPG. Because of the sensitivity of a of the camptothecin drugs to membrane associations, the method of fluorescence anisotropy titration was employed to study the equilibrium binding of camptothecin analogs with lipid bilayers. As described previously, the experiment consisted of determining the a values for a set of samples where the drug concentration in each was held constant (typically 1 or 2 $\mu$M), while the lipid concentration among the members of a set was varied from 0 to 0.29 M.

Figure 16:
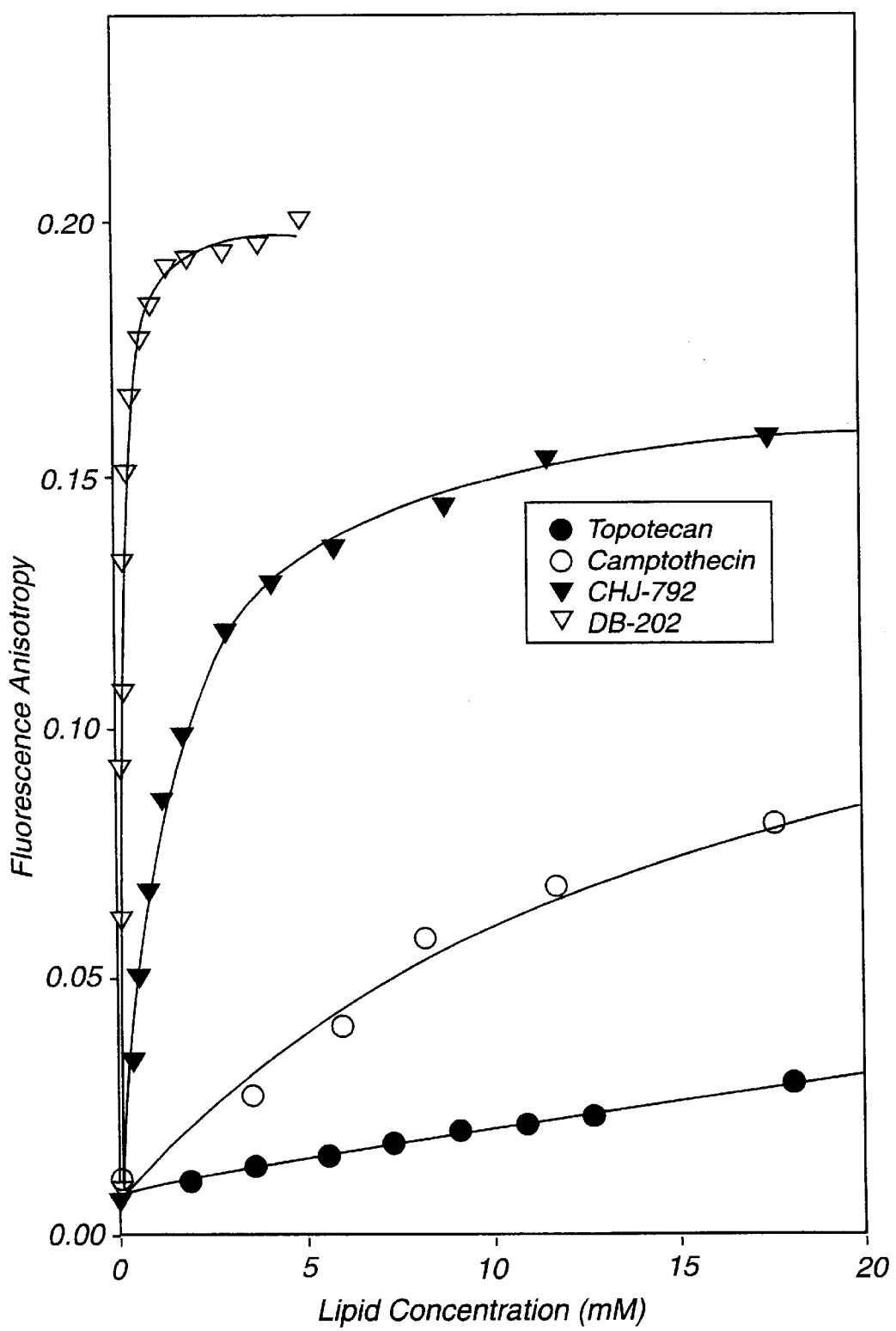
FIG. 16 is an illustration of equilibrium binding of camptothecin analogs to DMPC.
Figure 17:
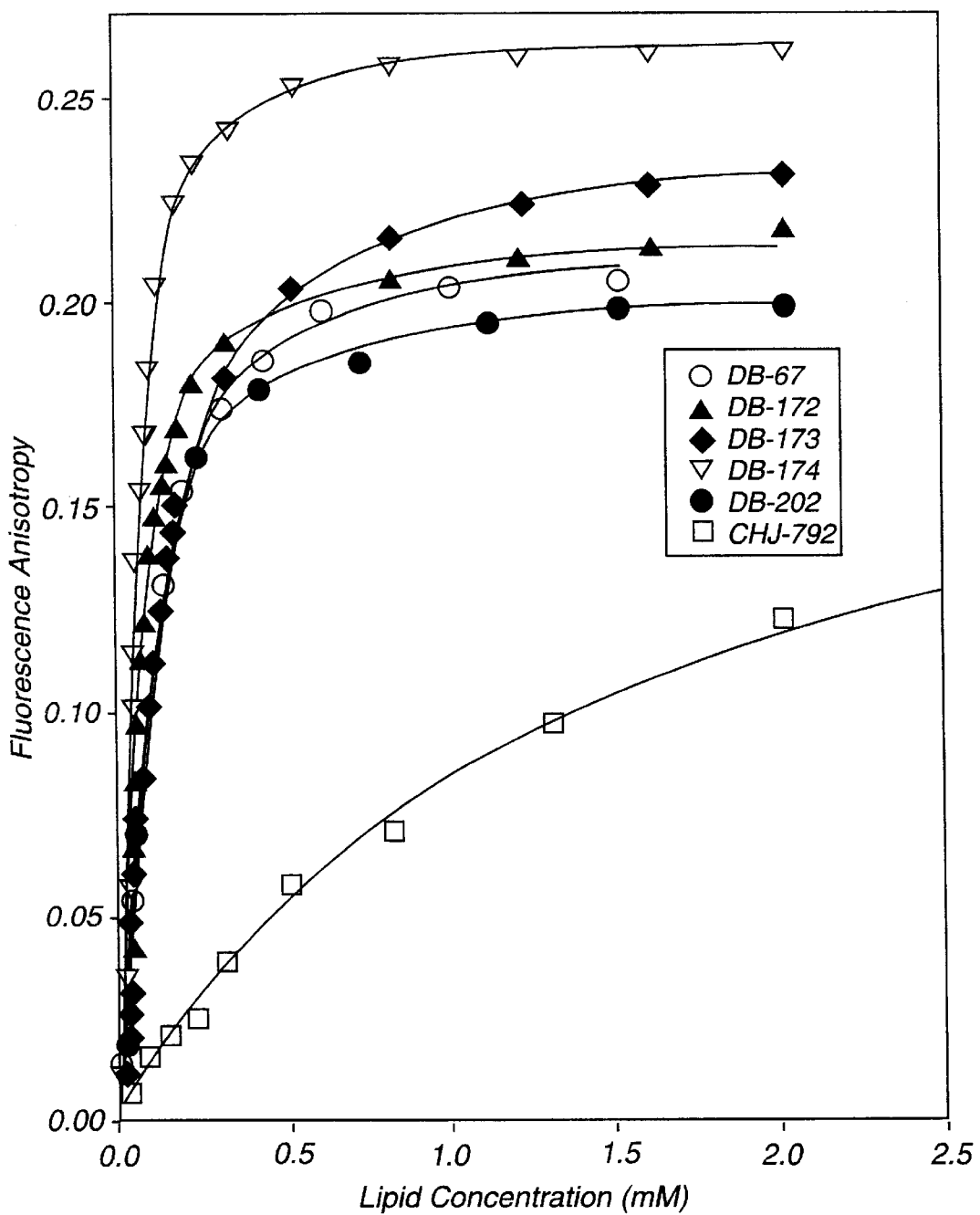
FIG. 17 is an illustration of equilibrium binding of highly lipophilic camptothecin analogs of the present invention to DMPC.
Figure 18:
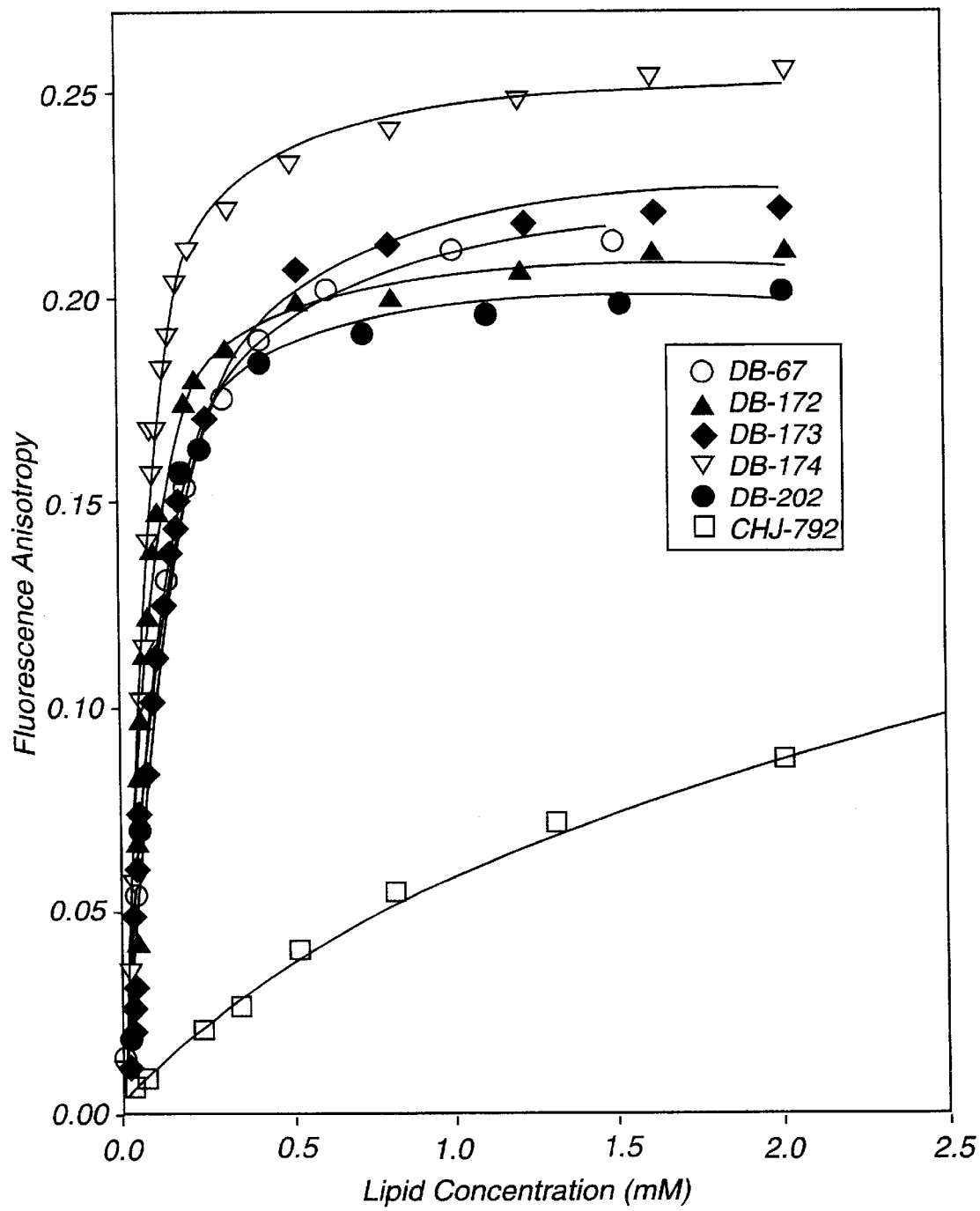
FIG. 18 is an illustration of equilibrium binding of highly lipophilic camptothecin analogs of the present invention to DMPG.
Figure 19:
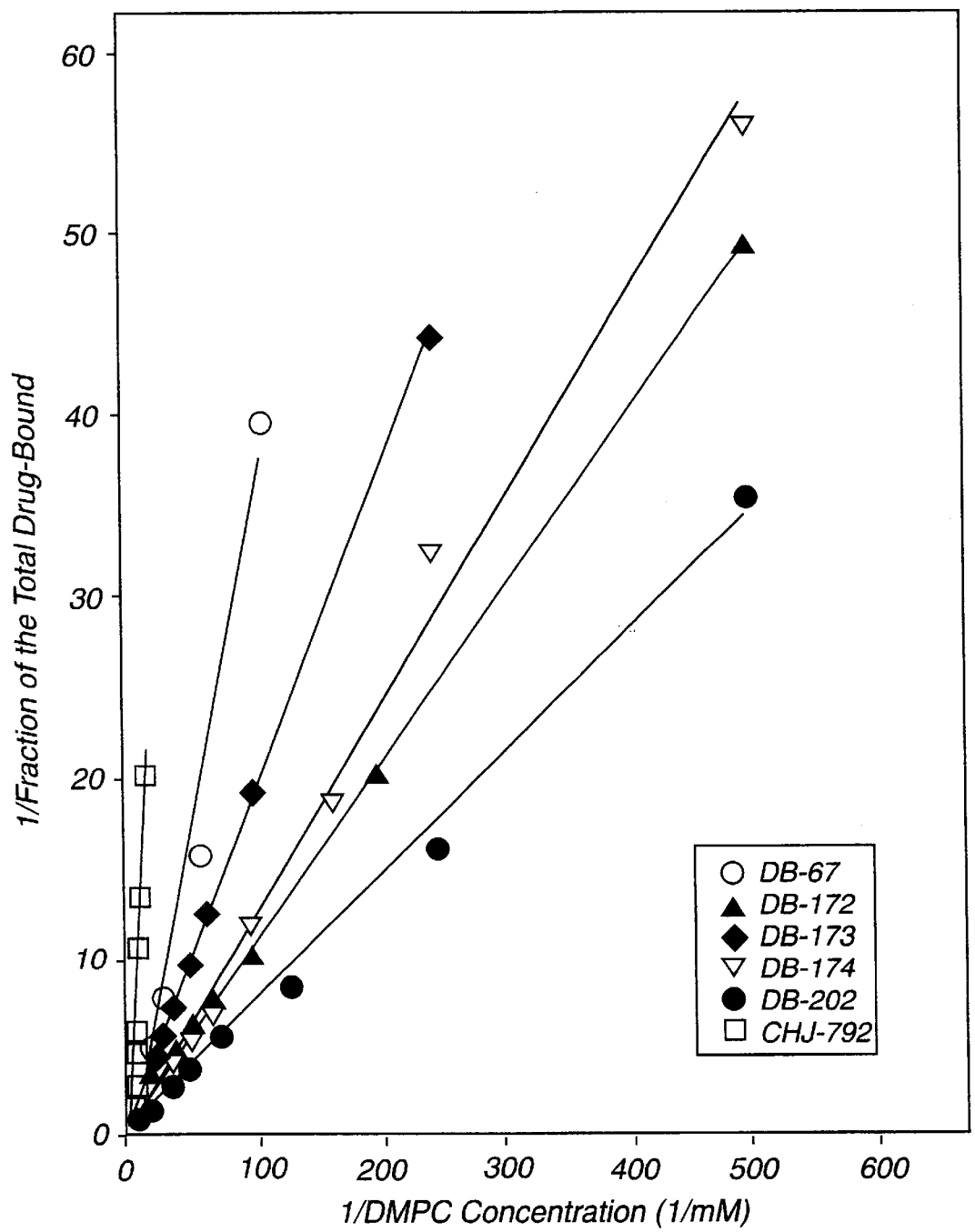
FIG. 19 is an illustration of double-reciprocal plots for the binding of highly lipophillic camptothecin analogs of the present invention to DMPC small unilamellar vesicles (SUVs) at 37° C.
Figure 20:
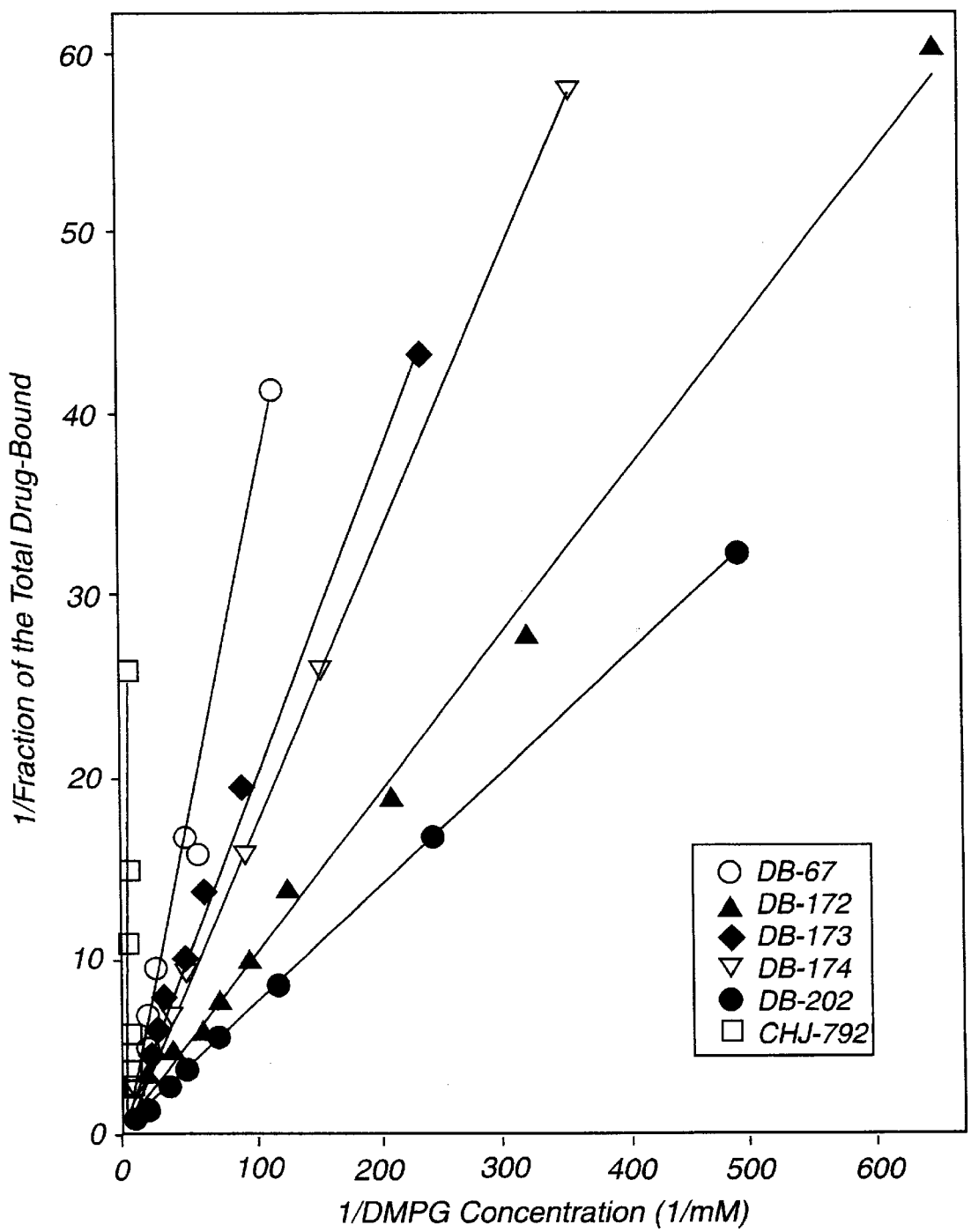
FIG. 20 is an illustration of double-reciprocal plots for the binding of highly lipophillic camptothecin analogs of the present invention to DMPG SUVs at 37° C.

As a consequence of the brilliant fluorescence emissions from the newly synthesized camptothecins (a summary of the spectral parameters can be found in Table 2), the adsorption isotherms summarized in FIGS. 16 through 18 were relatively free from any background signal. Using drug concentrations of 1 $\mu$M and long pass filters to isolate emitted light from background signal (that is, scattered exciting light and extraneous fluorescence signal due to the possible presence of impurities), signal levels from drugs dissolved in PBS buffer were typically 99.97% in the absence of membrane and greater than 98% in the presence of membrane. Adsorption isotherms were used to determine overall association constants for the camptothecin drugs. Overall association constants are defined as:

$$K = [A_B]/[A_F][L]$$

where $[A_B]$ represents the concentration of bound drug, $[A_F]$ represents the concentration of free drug, and $[L]$ represents the total lipid concentration in the vesicle suspension. This equation is valid when the concentration of free lipid is approximately equal to the concentration of total lipid (that is, the concentration of free lipid is in significant excess over the concentration of bound drug). Provided this condition is satisfied, K may be determined from the inverse of the slope of a double reciprocal plot. In such a double reciprocal plot (representative data are shown in FIGS. 19 and 20), 1/fraction of the total drug bound is plotted vs. 1/lipid concentration, with a y-intercept value of 1 (for a system displaying binding site homogeneity). Such double-reciprocal plots for the associations of the new camptothecin analogs with DMPC and DMPG small unilamellar vesicle (SUV) preparations were linear with good correlation coefficients. The linearity of these plots, as well as the corresponding plots for drug associations with other types of membrane preparations, indicates that fluorophore binding at these lipid concentrations is adequately described by the above equation.

The studies summarized in Table 3 examine the structural basis of camptothecin associations for lipid bilayers. Two types of membrane were included in these studies which were conducted under near physiological conditions of pH and temperature; these membranes include fluid-phase and electroneutral L-α-dimyristoylphosphatidylcholine (DMPC); and fluid-phase and negatively-charged L-α-dimyristoylphosphatidylglycerol (DMPG). DMPC and DMPG have identical chain length but the charge on their head groups differ.

TABLE 3

Overall association constants for camptothecin analogs interacting with unilamellar vesicles of electroneutral DMPC, negatively- charged DMPG in PBS buffer at PH 7.4 and 37° C.

| Compound | $K_{DMPC}$ (M$^{-1}$) | $K_{DMPG}$ (M$^{-1}$) |
| --- | --- | --- |
| 20(S)-camptothecin | 100 | 100 |
| 7-methyl-20(S)-camptothecin | 150 | 180 |
| 7-ethyl-20(S)-camptothecin | 250 | 300 |
| 7-propyl-20(S)-camptothecin | 540 | 600 |
| 7-methyl-10-methoxycamptothecin | 220 | 200 |
| 7-ethyl-10-methoxycamptothecin | 340 | 330 |
| 7-propyl-10-methoxycamptothecin | 440 | 570 |
| 7-methyl-10-hydroxycamptothecin | 220 | 90 |
| 7-ethyl-10-hydroxycamptothecin | 260 | 160 |
| 7-propyl-10-hydroxycamptothecin | 550 | 250 |
| 7-butyl-10-hydroxycamptothecin | 2100 | 1270 |
| DB-67 | 2700 | 2800 |
| DB-172 | 10500 | 10600 |
| DB-172 (Carboxylate form) | 385 | 155 |
| DB-173 | 5800 | 5800 |
| DB-174 | 9000 | 6600 |
| DB-174 (Carboxylate form) | 540 | 60 |
| CHJ-792 | 820 | 360 |

In the studies of Table 3, binding isotherms were constructed using the method of fluorescence anisotropy titration, and K values were determined from the slops of double-reciprocal plots. The K values are subject to 10% uncertainty. overall, the most striking feature of the data contained in Table 3 is the strong modulation which can be achieved through either a sole substitution at the 7 position or dual substitution at the 7 and 10 positions. Included in Table 3 are previously known camptothecin compounds. Data for these agents were included to show the highly lipophilic nature of the new camptothecins relative to the previous compounds. Topotecan was found to have a K value for DMPC liposomes some 10 times less than that for camptothecin. From Table 3 it is clear that the compounds of the present invention are much more lipophilic than either camptothecin or topotecan. For example, the affinities of DB67 for membranes composed of DMPC or DMPG are 27-fold and 28-fold greater that the corresponding values for camptothecin. DB172 and DB174 are some 100-fold and 90-fold more apt to bind DMPC membranes when compared with camptothecin. DB173 is also highly lipophilic, displaying a K value for DMPC some 58-fold greater than that observed for camptothecin. In summary, the novel compounds of the present invention listed in Table 3 were found to display the highest membrane affinities by far when compared against other, previous camptothecin analogs containing the same $\alpha$-hydroxy-$\delta$-lactone ring system.

Figure 21:
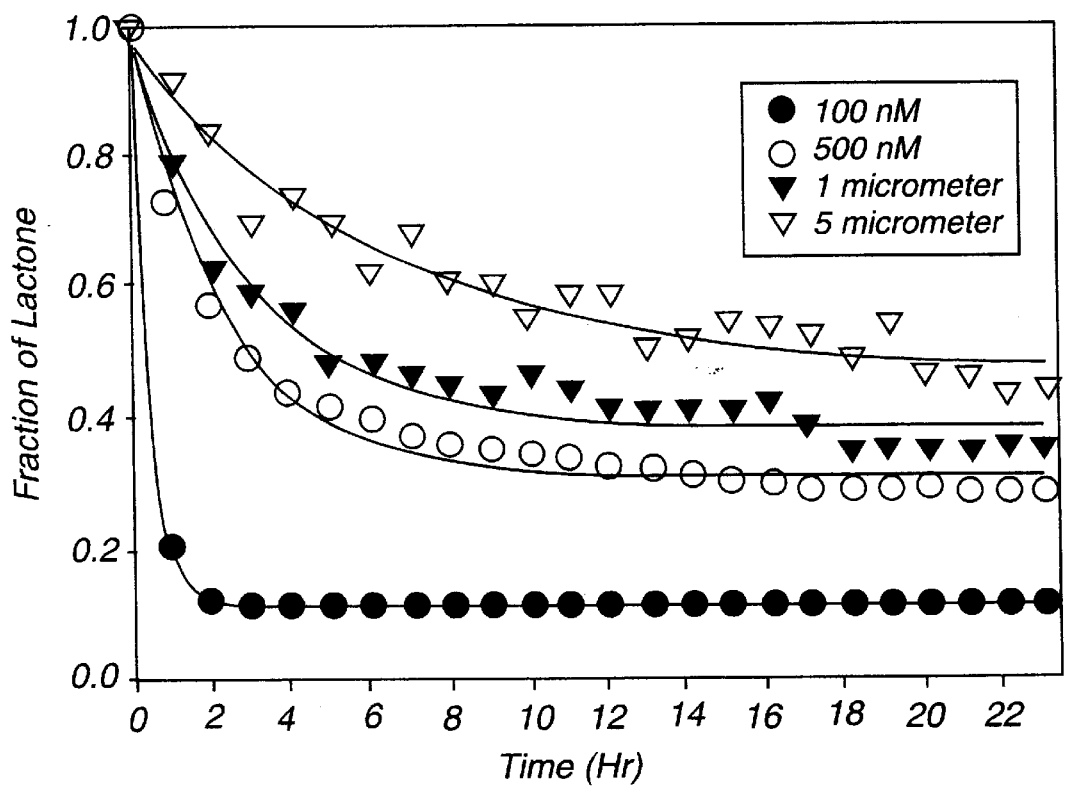
FIG. 21 is an illustration of the stability of DB-172 in PBS buffer pH 7.4 at 37° C.

Comparison of the Behavior of the Highly Lipophilic Camptothecins in Aqueous Solution FIG. 21 summarizes the stability of DB172 in phosphate buffered saline (PBS) buffer, pH 7.4, at physiological temperature. Shown in the figure are plots of lactone fraction as a function of time for DB172 at different concentrations. Drug was added to solution from a concentrated DMSO stock solution such that the volumes of DMSO were very small (less than 0.5%) relative to the volume of water. The drug stability was found to be markedly dependent on the drug concentration added. At the more dilute drug concentrations the drug hydrolyzes as previously observed for other camptothecins containing the $\alpha$-hydroxy-$\delta$-lactone moiety. At high drug concentrations marked stabilization of the lactone ring of DB-172 was observed, a finding which is not typically observed for other camptothecins.

Figure 22:
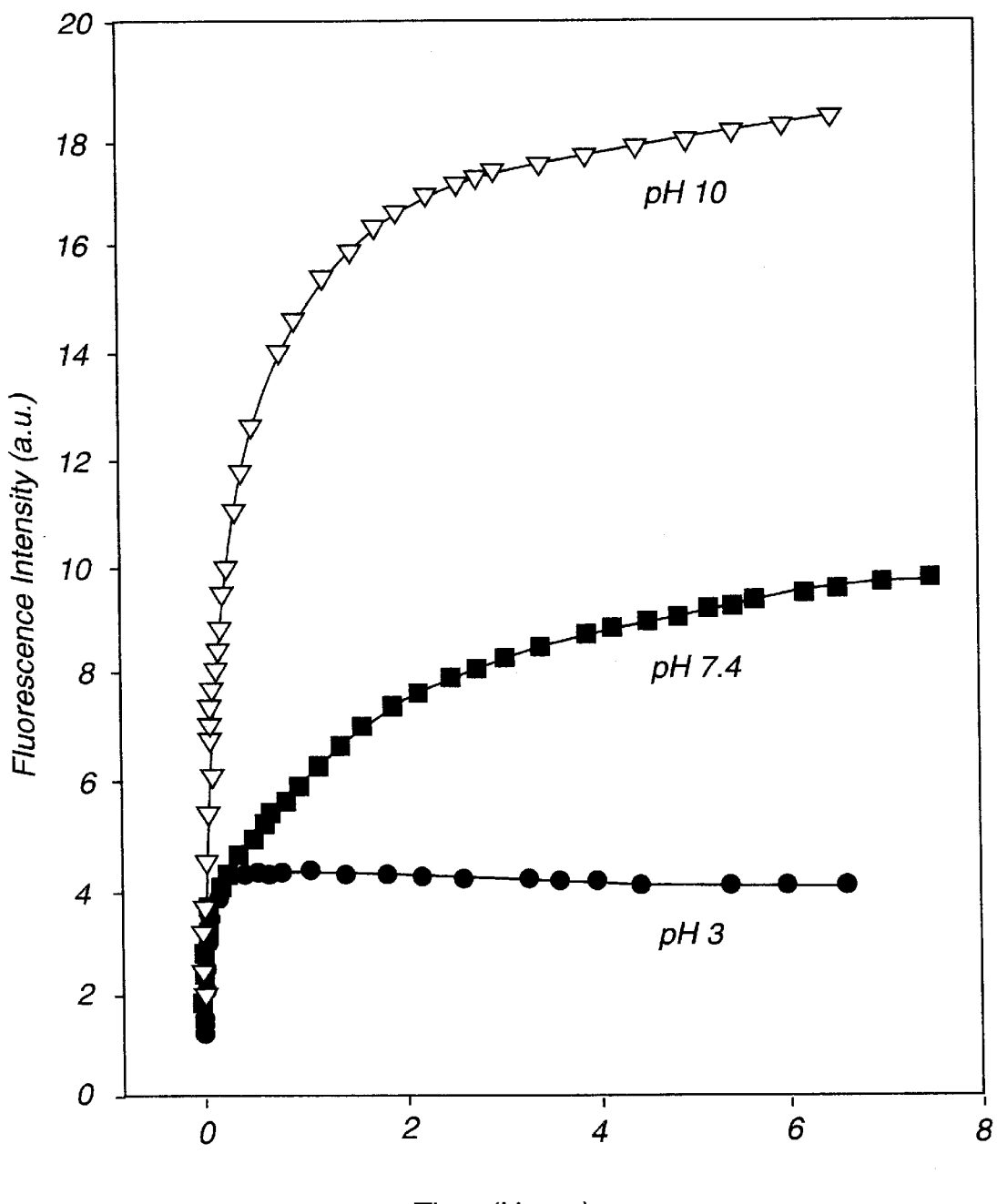
FIG. 22 is an illustration of the dependence of fluorescence intensity of DB-172 on time and drug concentration.

FIG. 22 summarizes the dependence of the fluorescence intensity of DB172 as a function of time and pH. In these experiments DB172 is added to solution as the lactone form. At low pH where the drug remains in the lactone form, the change in intensity with time is the lowest. At pH 10, where the conditions are such that the lactone more readily hydrolyzes and forms carboxylate, a significant change in fluorescence intensity is observed. It appears that a pH 10 nonfluorescent micellular aggregates composed of lactone disassemble and form open-ring carboxylate forms that tend to exist in solution as monomeric fluorescent species.

Figure 23:
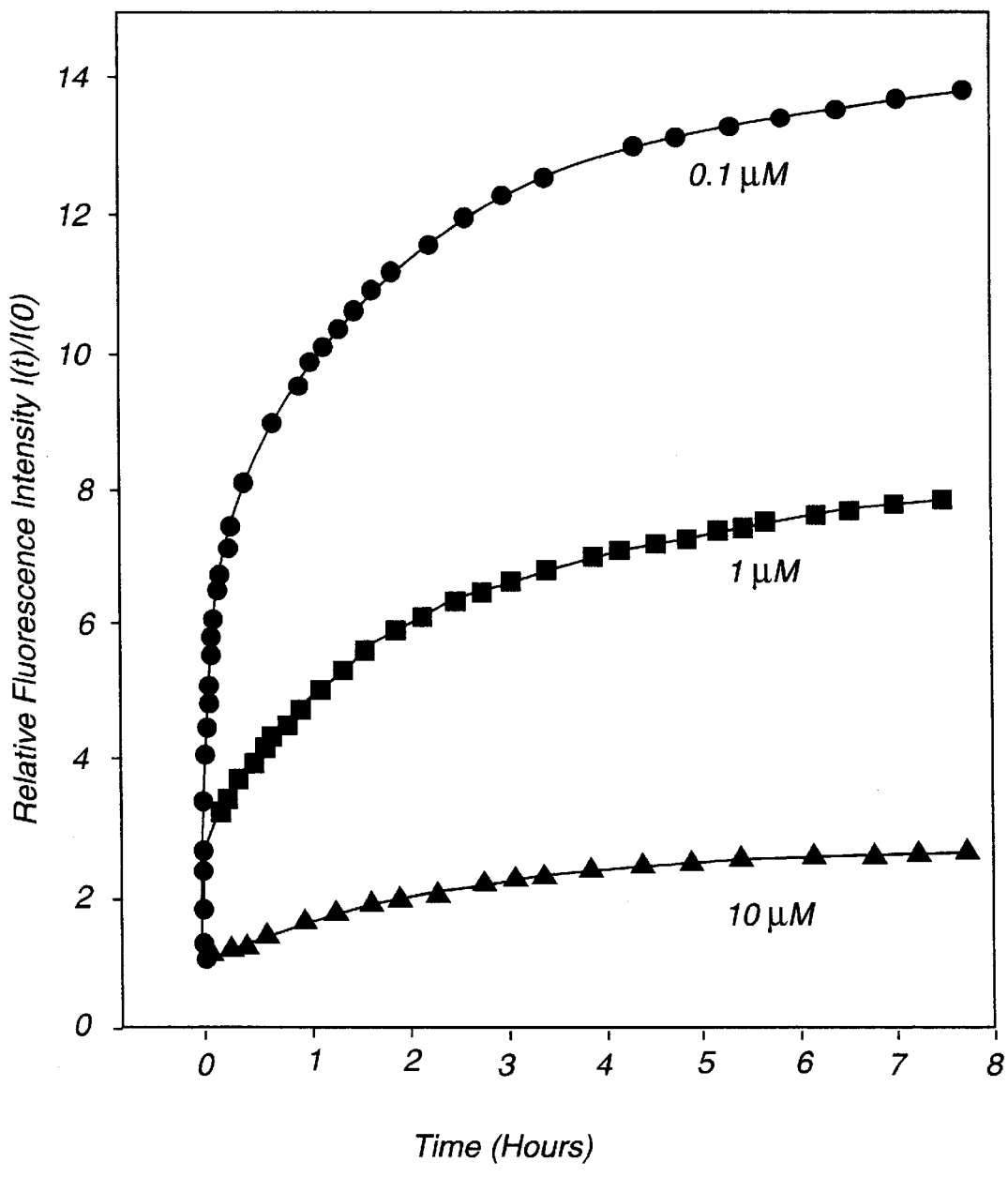
FIG. 23 is an illustration of the fluorescence intensity of DB-172 in dependence on time and concentration.
Figure 24:
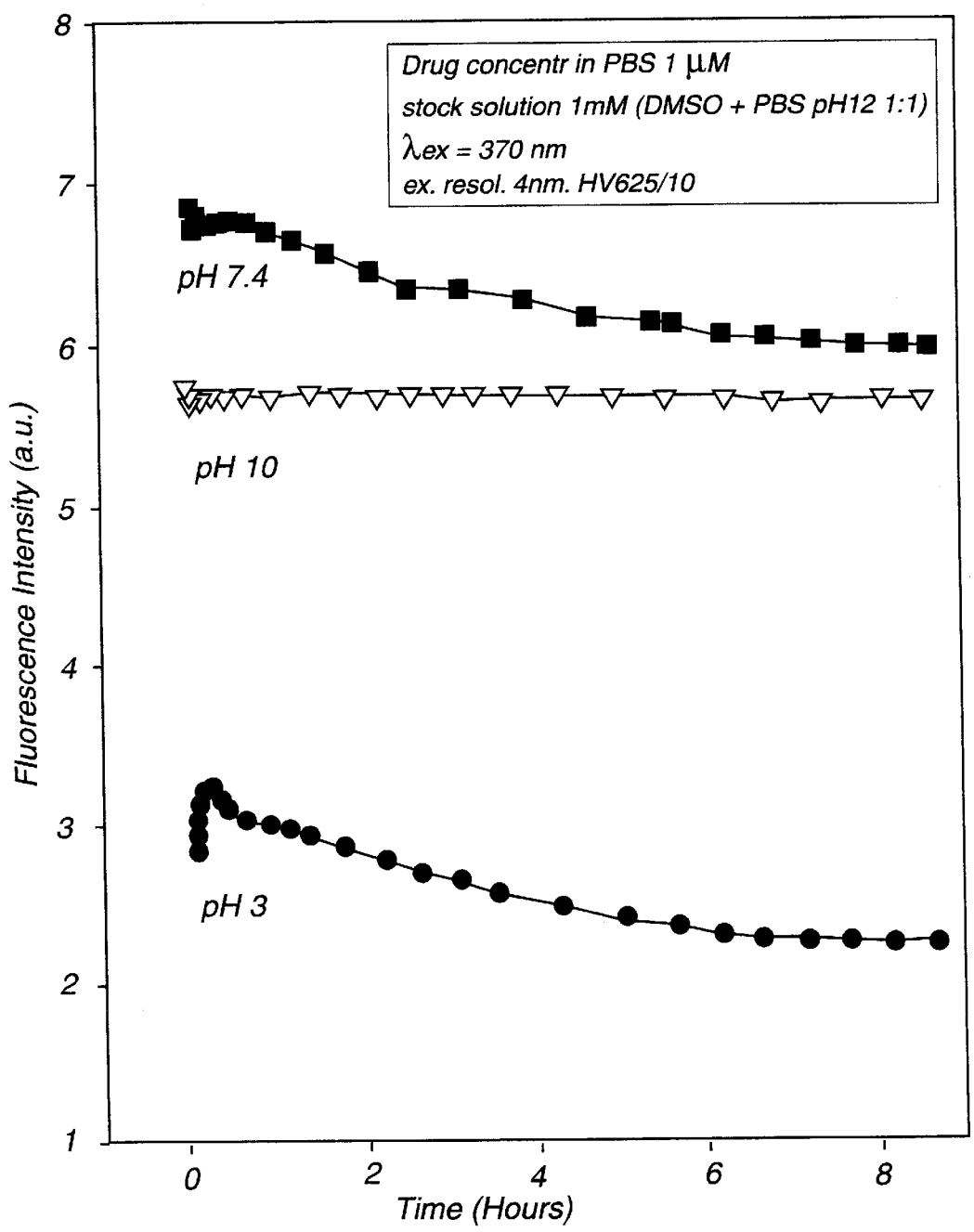
FIG. 24 is an illustration of the dependence of the total fluorescence intensity on time and pH for the carboxylate form of DB-172.

FIG. 23 explores the fluorescence intensity of DB172 as a function of concentration. Following the addition of low concentration of lactone drug to solution, the change in fluorescence signal is the greatest whereas at high drug concentration ($10^{-n}$M) the fluorescence intensity changes are minimal. It is believed that a low concentration the micellular aggregates of DB172 displaying reduced fluorescence can disassemble and form fluorescent carboxylate species, but at higher drug concentration the equilibrium favors that the agent remains in the aggregated or reduced fluorescence state. FIG. 24 shows that when the carboxylate form of DB172 is added to solution at pH 10, no change in fluorescence signal is observed at pH 10 while at lower pH values where lactone can form the fluorescence intensity decreases with time. Once again this decrease in fluorescence that occurs at reduced pH appear to be due to the formation of lactone aggregates of reduced fluorescence quantum yield.

Figure 25:
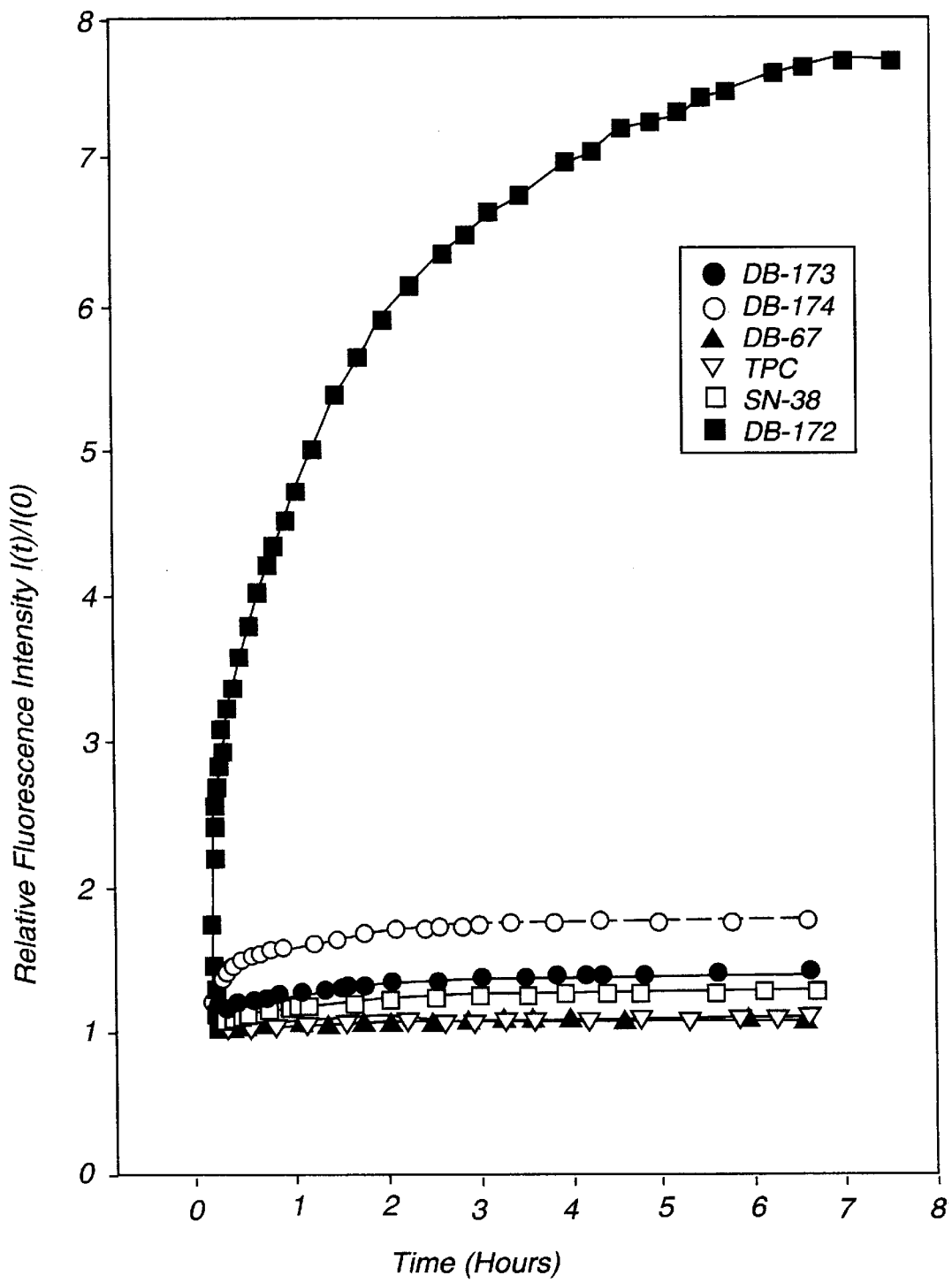
FIG. 25 is an illustration of the dependence of total fluorescence intensity on time for several camptothecin analogs of the present invention.

FIGS. 21 through 24 are consistent with the unusual ability of DB172 lactone to self-associate and form micelles at micromolar drug concentrations. The micellular DB172 aggregates display a reduced fluorescence. If conditions allow for hydrolysis to occur such that carboxylate forms, there is an increase in the fluorescence intensity of the sample. FIG. 25 compares the relative change in the fluorescence emission of a sample following addition of lactone drug forms to solution. In these experiments the values for each drug are normalized to a value of 1 at time equals to zero, and the ability of the various analogs to disassociate in the event the drugs are aggregated at time=0 is monitored with time. For several of the agents, hydrolysis to form carboxylate occurs in the solution. Since the carboxylate forms are less likely to self-associate and exhibit reduced fluorescence, disruption of the aggregates by drug hydrolysis proceeds with an increase in fluorescence intensity. While DB172 self-associates to an exceptionally high degree at time=0, the other agents self-associate to a much lesser extent and hence their signals are more constant with time and not as sensitive to hydrolysis reactions. DB173 and DB67 appear to be much more likely to be found in solution as monomeric drug relative to DB172. This could be a favorable characteristic in that solutions for administration to a patient will be more homogeneous than the aggregated DB172 particle suspensions.

Markedly Enhanced Stabilities of Highly Lipophilic Camptothecins in Human Blood

Figure 26:
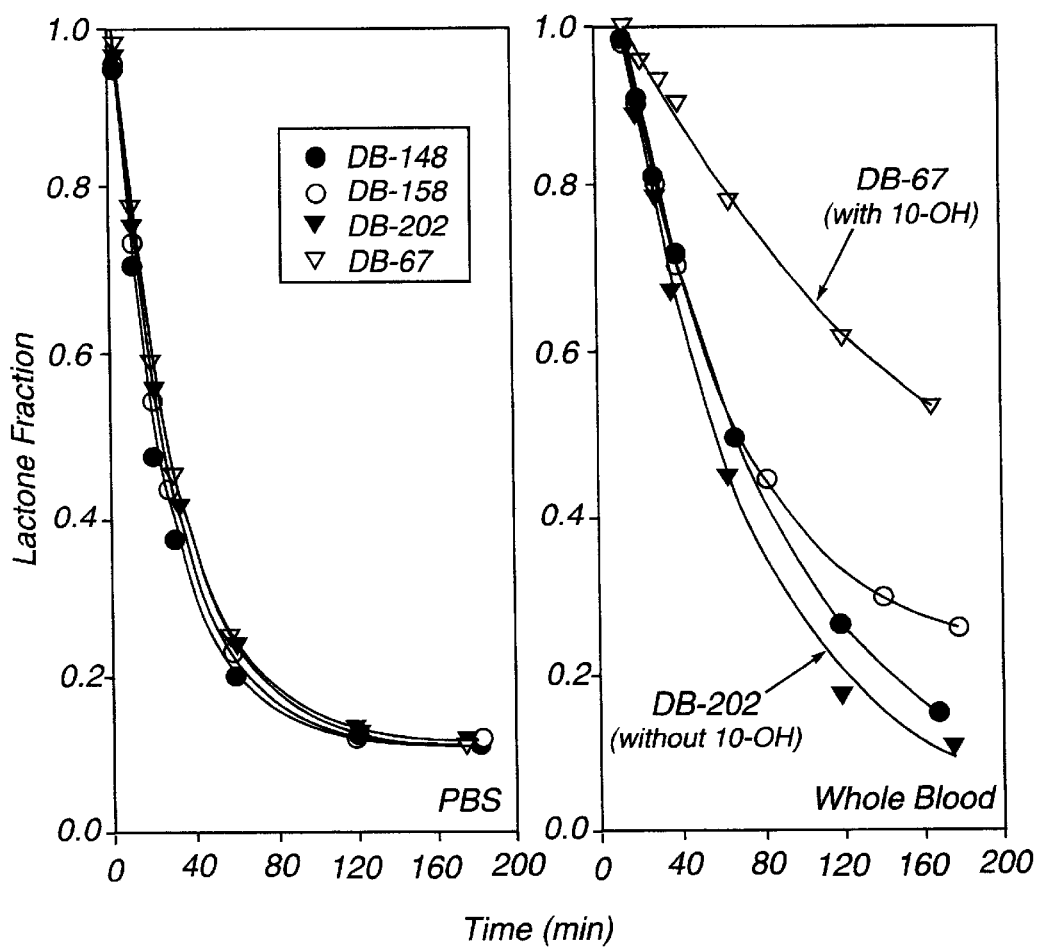
FIG. 26 is an illustration of the drug stability of several camptothecin analogs of the present invention in phosphate buffered saline (PBS) and human blood.
Figure 27:
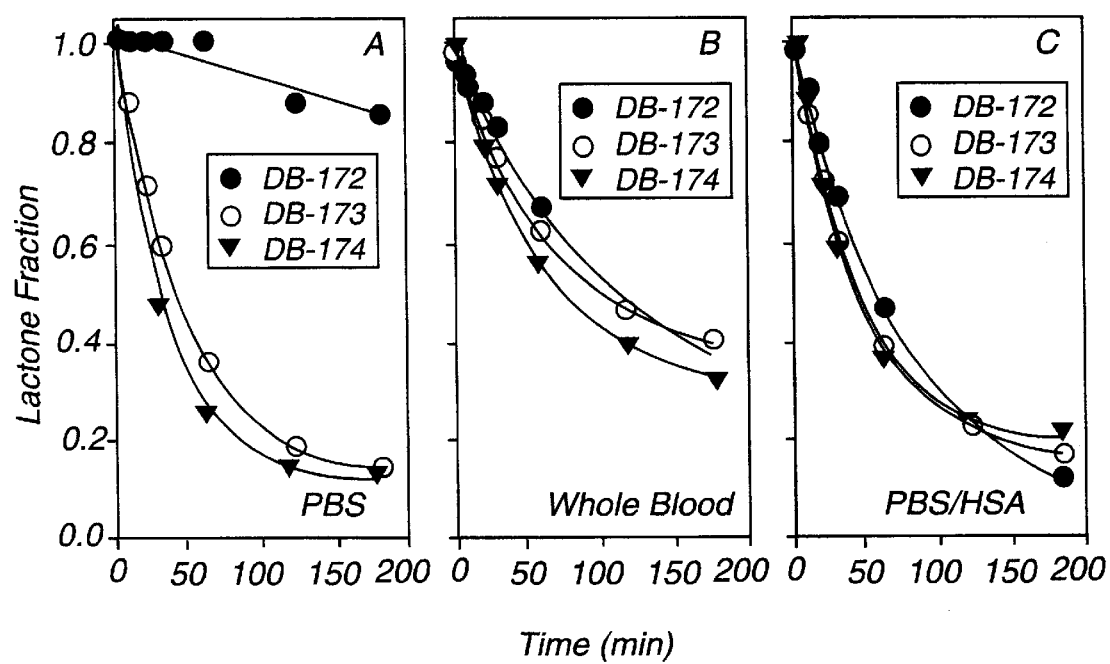
FIG. 27 is an illustration of the drug stability of several camptothecin analogs of the present invention in PBS, whole blood and PBS) human serum albumin (HSA).

In was also demonstrated that the active lactone forms of highly lipophilic camptothecins of the present invention also persist for much longer times in human tissues such as blood when compared with water-soluble analogs. FIG. 26 compares the stabilities of several new camptothecin analogs in their free form in PBS buffer (Panel A) versus in whole blood (Panel B). These compounds include: 7-t-butyldimethylsilylcamptothecin (DB202), 7-t-butyldimethylsilyl-10-hydroxycamptothecin (DB67), 7-(3-chloropropyl)dimethylsilylcamptothecin (DB148), and 7-(3-chloropropyl)-dimethylsilyl-10-hydroxycamptothecin (DB158). FIG. 27 summarizes the stability data for DB172, DB173 and DB174 in PBS buffer only (Panel A), PBS buffer containing physiologically relevant 30 mg/ml levels of HSA (Panel B), and human blood (Panel C). All experiments were carried out at physiological temperature.

The highly biologically-active and lipophilic compound, 7-t-butyldimethylsilyl-10-hydroxycamptothecin (DB-67), was found to display superior stability in human blood, with a $t_{1/2}$ of 130 min and a % lactone at equilibrium value of 30 (compare with % lactone at equilibrium values in whole human blood for 9-aminocamptothecin (<0.3%), camptothecin (5.3%), topotecan (8.6%), CPT-11 (21.0%), and SN-38 (19.5%)). The stability data are summarized in Table 4. The new DB67 agent was found to be 25-times more lipophilic than camptothecin, and its 10-hydroxy functionality was found to markedly aid in promoting stability in the presence of HSA. DB67 may be an ideal candidate for the treatment of brain cancer. With intrinsic activity several-fold greater than camptothecin, DB67 displays very high equilibrium lactone levels in human blood, is not tightly bound to human albumin like camptothecin and 9-aminocamptothecin, and is highly lipophilic which should enable the agent to more readily cross the blood brain barrier.

TABLE 3

Stability parameters for Camptothecin analogs in different biological fluids.

| DRUG NAME and FLUID | $t_{1/2}$ (minutes) | % Lactone at Equilibrium |
|---|---|---|
| DB 202 | | |
| Whole Blood | 71.9 +/- 4.2 | 1.0 +/- 0.1 |
| HSA | 46.3 +/- 1.0 | 0.1 +/- 0.2 |
| PBS | 27.9 +/- 1.9 | 12.2 +/- 0.4 |
| RBC | 79.4 +/- 3.3 | 59.4 +/- 0.0 |
| DB 148 | | |
| Whole Blood | 85.6 +/- 9.2 | 2.2 +/- 3.6 |
| HSA | 16.0 +/- 0.2 | 2.7 +/- 0.2 |
| PBS | 23.3 +/- 2.4 | 12.0 +/- 0.5 |
| RBC | 59.7 +/- 2.9 | 43.4 +/- 0.8 |
| DB 67 | | |
| Whole Blood | 133.0 +/- 15.9 | 30.5 +/- 1.9 |
| HSA | 119.0 +/- 5.3 | 10.5 +/- 2.0 |
| PBS | 31.8 +/- 0.4 | 10.2 +/- 0.3 |
| RBC | 51.4 +/- 0.5 | 41.4 +/- 0.7 |
| CHJ 792 | | |
| Whole Blood | 37.6 +/- 6.2 | 12.3 +/- 0.0 |
| HSA | 32.0 +/- 1.3 | 3.7 +/- 0.3 |
| PBS | 31.3 +/- 0.6 | 10.5 +/- 0.3 |
| DB 158 | | |
| Whole Blood | 65.3 +/- 9.0 | 17.8 +/- 2.0 |
| HSA | 48.0 +/- 0.9 | 17.2 +/- 0.7 |
| PBS | 29.5 +/- 1.7 | 11.3 +/- 1.8 |
| RBC | 67.7 +/- 8.5 | 50.2 +/- 1.7 |
| 7 TMS | | |
| Whole Blood | 54.6 +/- 3.6 | 23.7 +/- 0.0 |
| HSA | 58.5 +/- 6.8 | 16.4 +/- 1.9 |
| PBS | 34.6 +/- 1.0 | 11.1 +/- 0.1 |
| SN 38 | | |
| Whole Blood | 50.7 +/- 1.4 | 20.2 +/- 1.9 |
| HSA | 88.1 +/- 2.9 | 24.3 +/- 0.7 |
| Topotecan | | |
| Whole Blood | 30.9 +/- 1.4 | 8.61 +/- 0.4 |
| HSA | 22.1 +/- 0.7 | 7.06 +/- 0.3 |
| DB172 | | |
| Whole Blood | 106.6 +/- 10.8 | 24.1 +/- 2.6 |
| HSA | 86.1 +/- 10.3 | 4.3 +/- 1.0 |
| DB173 | | |
| Whole Blood | 69.0 +/- 4.0 | 36.3 +/- 1.7 |
| HSA | 49.0 +/- 1.3 | 15.5 +/- 0.5 |
| PBS | 45.3 +/- 2.0 | 11.9 +/- 0.3 |
| DB 174 | | |
| Whole Blood | 40.3 +/- 3.2 | 33.0 +/- 0.4 |
| HSA | 37.7 +/- 0.9 | 20.4 +/- 0.2 |
| PBS | 29.7 +/- 0.4 | 13.7 +/- 0.7 |
| DB 124 | | |
| Whole Blood | 63.1 +/- 7.4 | 31.8 +/- 0.8 |
| HSA | 40.0 +/- 0.3 | 12.2 +/- 0.3 |
| PBS | 30.3 +/- 1.0 | 8.9 +/- 0.3 |
| DB 104 | | |
| Whole Blood | 77.2 +/- 1.8 | 48.1 +/- 2.0 |
| HSA | 29.6 +/- 0.8 | 8.5 +/- 0.2 |
| PBS | 24.1 +/- 1.0 | 7.5 +/- 0.2 |
| Camptothecin | | |
| Whole Blood | 21.6 +/- 2.6 | 5.3 +/- 0.6 |
| HAS | 11.9 +/- 0.3 | <0.5 |
| PBS | 23.8 +/- 1.3 | 17 +/- 2.0 |

Also noteworthy are the very high human blood stabilities of DB-173 (36% lactone at equilibrium) and DB174 (33% lactone at equilibrium). These values are significantly greater than clinically relevant water-soluble camptothecins and they compete favorably with lipophilic camptothecins such as DB-172 that contain an unsubstituted A-ring.

Highly Lipophilic Camptothecins Display Oral Bioavailibility

Figure 28:
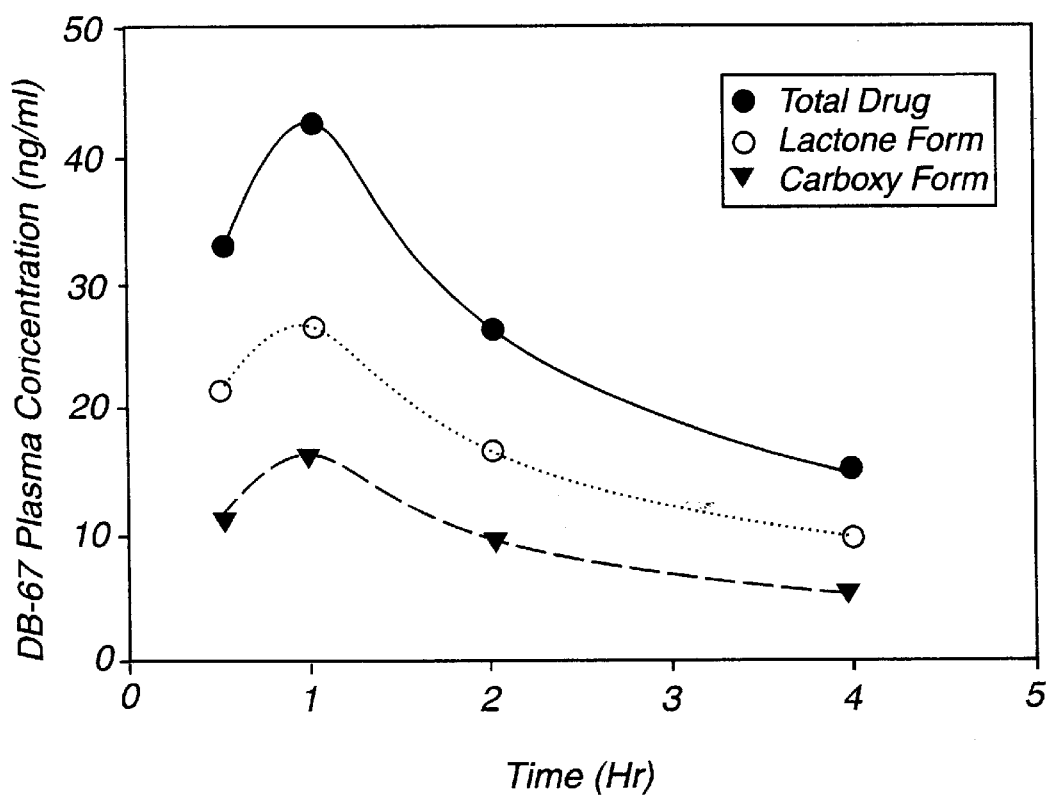
FIG. 28 is an illustration of the plasma concentration of DB-67 after oral dosage.

FIG. 28 contains data which demonstrate that DB-67 is absorbed from the gastrointestinal tract. To evaluate the blood levels achieved following dosing at 5 mg/kg, four animals were given 0.1 ml intrastomach injections of DB-67 dissolved in DMSO. The stock contained DB67 at a concentration of 1.6 mg/ml. At time points of 30 min, 1 hr, 2 hr, and 4 hr, 1 ml samples of blood were drawn and collected by heart puncturing. The samples were centrifuged for 3 min and stored frozen until analysis was carried out. Note that DB67 levels rise above the 40 ng/ml level with much of the drug persisting as active lactone drug. Thus, the novel highly lipophilic analogs described here may be administered orally and will appear in the bloodstream following administration.

Highly Lipophilic Camptothecins Display High Anticancer Potency Even in the Presence Human Serum Albumin As discussed previously, the spontaneous hydrolysis of camptothecin in aqueous solution yields the ring-opened carboxylate form which is far less active than the ring-closed lactone form. Therefore, the equilibrium between the lactone and carboxylate forms is a most important determinant of the drug activities. Previous studies indicated that human serum albumin (HSA) greatly affects the equilibrium in favor of the carboxylate for camptothecin by preferentially interacting with the carboxylate form. Because of this HSA effect, levels of the biologically-active lactone form of camptothecin can be attenuated at the tumor site. The drug-HSA interactions can be manipulated by drug structural modification: A 10-OH substitution decreases the affinity of drug for HSA approximately 20-fold and an additional 7-ethyl substitution further alters the binding in favor of the lactone form. To determine the impact of HSA on the cytotoxicities of the blood-stable camptothecin analogs of the present invention, the cytotoxic effects of the camptothecin analogs were studied.

Sulphorhodamine B (SRB) assay was used. This assay measures the total protein levels in the living cells. Proteins from dead cells are lysed and removed in the washing step before TCA fixation. However, it is possible that cells in the early stage of death still have their membrane integrity and therefore retain the protein contents inside. As a result, the optical density at 490 nm can sometimes be overestimated and the cytotoxicity underestimated. To validate the SRB assay, a diverse range of chemotherapeutic agents have been tested across multiple panels of tumor cell lines, and close correlations have been found with standard tetrazolium (MIT) assay and clonogenic assays. The SRB assay is now a well regarded assay and was recently approved by NCI as a standard assay for anticancer drug screening.

The cytotoxicities of various camptothecins against MDA-MB-435 tumorigenic metastatic human breast cancer cells in the absence and presence of 1 mg/ml HSA are summarized in Table 5. The cytotoxicity values for cells exposed to drug for 72 hrs. are summarized in Table 5. Overall, HSA is able to strongly attenuate the $IC_{50}$ values of camptothecin, but the extent to which HSA modulates the cytotoxicities of the new highly lipophilic analogs is significantly reduced. In fact, 1 mg/ml HSA had no effect on the cytotoxic activity of DB173. In the presence of HAS, DB173 displays a low nM potency against the human breast cancer cells. The ability of the agents to remain potent even in the presence of albumin is potentially significant because of the great abundance of this protein throughout the blood and tissue of the body.

TABLE 4

IC$_{50}$ Values of Camptothecin and Analogs Against MDA-MB-435 Tumorogenic Metastatic Human Breast Cancer Cells in the Absence and Presence of Human Serum Albumin.

| Compound | IC$_{50}$ (nM) (w/o HSA) | IC$_{50}$ (nM) (w/HSA) |
|---|---|---|
| Camptothecin | 8 | >200 |
| 7-Ethyl-10-Hydroxycamptothecin (SN-38) | 20 | — |
| DB-174 | 12 | — |
| DB-67 | 7 | 22 |
| DB-173 | 4 | 4 |

The present inventors have thus discovered that introduction of a silyl group or a silylyalkyl group (for example, a trimethylsilyl group or a trimethylsilylethyl group) at position 7 of the camptothecin structure typically results in a compound with better anti-tumor activity and human blood stability than camptothecin (see, for example, the compound of Example 1 as compared to (20S)-CPT) and other previous camptothecin analogs. Dual substitution at the 7 and 10 positions is even more favorable (see, for example, compounds DB-173 and DB-174). The silyl group or the silylalkyl group is also beneficial in the irinotecan series (see, for example, the compound of Example 6 as compared to irinotecan).

The anti-tumor activity remains essentially unchanged when a hydroxy group is introduced at position 10 of the compound of Example 1 to produce the compound of Example 5. The compound of Example 6 is a relative of SN-38, the active metabolite of irinotecan. High activities were also observed in the present studies when a trimethylsilyl group was introduced in conjunction with a fluoro atom at position 11 (see, for example, the compound of Example 7), or a primary amine group at positions 10 or 11 (see, respectively, Examples 8 and 9). Introduction of a fluoro atom in position 12 also results in an analog only approximately 2 times less potent than camptothecin (see, Example 11 as compared to (20S)-CPT). This result is surprising considering the poor activity of the 12-substituted camptothecins reported previously in the literature.

The novel camptothecin analogs of the present invention have unique biophysical and physiological properties. These highly lipophilic camptothecin analogs with B-ring modifications and A- and B-ring modifications display markedly improved α-hydroxy-δ-lactone ring stability in human blood. The camptothecin analogs of the present invention also display oral bioavailibility and potent anticancer activity even in the presence of human serum albumin.

A mammal (human or animal) may thus be treated by a method which comprises the administration to the mammal of a pharmaceutically effective amount of a compound of formula (1) or a pharmaceutically acceptable salt thereof. The condition of the mammal can thereby be improved.

The compounds of the present invention can be administered in a variety of dosage forms including, for example: parenterally (for example, intravenously, intradermally, intramuscularly or subcutaneously); orally (for example, in the form of tablets, lozengers, capsules, suspensions or liquid solutions); rectally or vaginally, in the form of a suppository; or topically (for example, as a paste, cream, gel or lotion).

Optimal dosages to be administered may be determined by those skilled in the art and will vary with the particular compound of formula (1) to be used, the strength of the preparation, the mode of administration, the time and frequency of administration, and the advancement of the patient's condition. Additional factors depending on the particular patient will result in the need to adjust dosages. Such factors include patient age, weight, gender and diet. Dosages may be administered at once or divided into a number of smaller doses administered at varying intervals of time.

EXAMPLES

The following examples are provided for illustration of the invention and are not intended to be limiting thereof.

Example 1

Preparation of (20S)-7-trimethylsilylcamptothecin

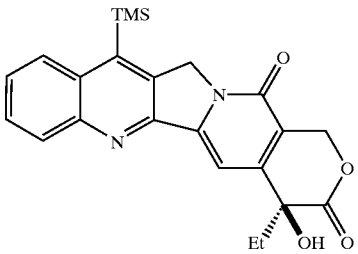

(1) (S)-4-Ethyl-4-hydroxy-6-iodo-3-oxo-7-(3-trimethylsilyl-2-propynyl)-1H-pyrano[3,4-C]-8-pyridone To a solution of (S)-4-ethyl-4-hydroxy-6-iodo-3-oxo-1H-pyrano[3,4-c]-8-pyridone [iodopyridone (2), 250 mg, 0.746 mol] in DME (2.5 mL) and DMF (0.60 mL) at 0° C. under argon was added 60% NaH in mineral oil (31.3 mg, 0.783 mmol). LiBr (150 mg, 1.75 mmol) was added 10 min latter. After 15 min at room temperature, 3-trimethylsilyl-2-propynyl bromide (430 mg, 2.24 mmol) was injected and the reaction mixture was heated in the dark at 65° C. for 20 h. The final solution was poured into brine (20 mL), extracted with AcOEt (6×15 mL) and dried (Na$_2$SO$_4$). The residue obtained after removal of the solvents was subjected to flash-chromatography (CHCl$_3$/AcOEt 95:5) to give 283 mg (85%) of a foam: $[\alpha]^{20}_D$+36.7 (c 1, CHCl$_3$); IR (neat, cm$^{-1}$) 3384, 2940, 2166, 1730, 1634, 1518, 1406, 1130, 841, 752; $^1$H NMR (300 MHz, CDCl$_3$) δ 0.14 (s, 9 H), 0.95 (t, J=7.4 Hz, 3 H), 1.77 (m, 2 H), 3.66 (s, 1 H), 5.00 (d, J=17.2 Hz, 1 H), 5.10 (d, J=16.4 Hz, 1 H), 5.15 (d, J=17.2 Hz, 1 H), 5.49 (d, J=16.4 Hz, 1 H), 7.16 (s, 1 H); $^{13}$C NMR (75 MHz, CDCl$_3$) δ −0.40, 7.7, 31.5, 44.5, 66.3, 71.8, 90.9, 97.9, 116.5, 118.1, 148.6, 157.9, 173.3; HRMS (EI) m/z calcd for C$_{16}$H$_{20}$INO$_4$Si (M$^+$) 445.0206, found 445.0203; LRMS (EI) m/z 445 (M$^+$), 430, 416, 386.

(2) (20S)-7-Trimethylsilylcamptothecin

A solution of the compound prepared in (1) (36.6 mg, 0.082 mmol), phenyl isonitrile (0.25 mmol) and hexamethylditin (42 mg, 0.123 mmol) in benzene (1.3 mL) under argon was irradiated at 70° C. with a 275W GE sunlamp for 10 h. The final reaction mixture was concentrated and subjected to flash-chromatography (CHCl$_3$/MeOH 96:4) to provide 18.8 mg (54%) of a slightly yellow solid: [α]$_D^{20}$+ 39.0 (c 0.2, CHCl$_3$/MeOH 4:1); $^1$H NMR (300 MHz, CDCl$_3$/CD$_3$OD 3:1) δ0.50 (s, 9 H), 0.83 (t, J=7.4 Hz, 3 H), 1.74 (m, 2 H), 3.72 (br s, 1 H), 5.12 (d, J=16.4 Hz, 1 H), 5.16 (br s, 2 H), 5.47 (d, J=16.4 Hz, 1 H), 7.49 (t, J=8.1 Hz, 1 H), 7.54 (s, 1 H), 7.62 (t, J=8.1 Hz, 1 H), 8.02 (d, J=8.1 Hz, 1 H), 8.07 (d, J=8.1 Hz, 1 H); $^{13}$C NMR (75 MHz, CDCl$_3$/CD$_3$OD 3:1) δ0.9, 7.2, 29.3, 31.0, 51.7, 65.5, 98.3, 118.4, 127.3, 128.0, 129.7, 130.0, 131.8, 134.3, 144.7, 145.6, 147.3, 151.1, 173.5; HRMS (EI) m/z calcd for C$_{23}$H$_{24}$N$_2$O$_4$Si (M$^+$) 420.1505, found 420.1501; LRMS (EI) m/z 420 (M$^+$), 391, 376, 361, 347, 320, 291.

Example 2

Preparation of (20S)-7-tert-butyldimethylsilylcamptothecin (DB-202)

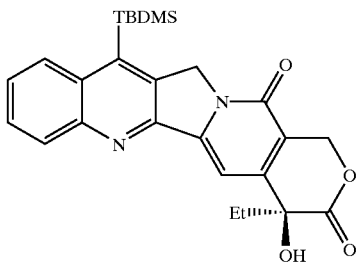

(1) (S)-4-Ethyl-4-hydroxy-6-iodo-3-oxo-7-(3-tert-butyldimethylsilyl-2-propynyl)-1H-pyrano[3,4-c]-8-pyridone Following the procedure described in Example 1-(1), iodopyridone (2) (200 mg, 0.60 mmol) and 3-tert-butyldimethylsilyl-2-propynyl bromide (280 mg, 1.20 mmol) provided, after flash-chromatography (CH$_2$Cl$_2$/AcOEt 9:1), 173 mg (59%) of a white foam: [α]$_D^{20}$+58 (c 0.2, CHCl$_3$); IR (CHCl$_3$, cm$^{-1}$) 3548, 2950, 2927, 2859, 1745, 1648, 1526; $^1$H NMR (300 MHz, CDCl$_3$) δ0.08 (s, 6 H), 0.92 (m, 12 H), 1.79 (m, 2 H), 3.77 (br s, 1 H), 5.00–5.25 (m, 3 H), 5.50 (d, J=16.4 Hz, 1 H) 7.19 (s, 1 H); $^{13}$C NMR (75 MHz, CDCl$_3$) δ–4.9, 7.63, 16.6, 26.0, 31.6, 44.5, 66.3, 71.8, 89.4, 98.6, 100.0, 116.5, 118.1, 148.6, 158.0, 173.2; HRMS (EI) m/z calcd for C$_{19}$H$_{26}$INO$_4$Si (M$^+$) 487.0679, found 487.0676; LRMS (EI) m/z 487 (M$^+$), 430, 386, 96, 81, 57.

(2) (20S)-7-tert-butyldimethylsilylcamptothecin

Following the procedure described in Example 1-(2), the compound prepared in (1) (48.7 mg, 0.10 mmol) afforded, after flash-chromatographies (CH$_2$Cl$_2$/MeOH 96:4; CH$_2$Cl$_2$/acetone 9:1), 24.8 mg (54%) of an off yellow solid: [α]$_D^{20}$+ 35.5 (c 0.2, CHCl$_3$); IR (CHCl$_3$, cm$^{-1}$) 3028, 2980, 2960, 2932, 2859, 1741, 1658, 1600, 1555, 1257, 1198, 1158, 1045; $^1$H NMR (300 MHz, CDCl$_3$) δ0.69 (s, 6 H), 0.98 (s, 9 H), 1.03 (t, J=7.3 Hz, 3 H), 1.86 (m, 2 H), 3.86 (s, 1 H), 5.29 (d, J=16.3 Hz, 1 H), 5.31 (s, 2 H), 5.73 (d, J=16.3 Hz, 1 H), 7.60 (d, J=6.3 Hz, 1 H), 7.60 (t, J=7.0 Hz, 1 H), 7.66 (s, 1 H), 7.74 (t, J=7.3 Hz, 1 H) 8.20 (t, J=8.1 Hz, 2 H); $^{13}$C NMR (75 MHz, CDCl$_3$) δ–0.56, 7.80, 19.2, 27.1, 31.6, 52.4, 66.3, 72.8, 97.7, 118.2, 127.0, 129.5, 129.6, 130.8, 132.7, 136.0, 143.0, 146.4, 148.0, 150.1, 150.6, 157.4, 173.9; HRMS (EI) m/z calcd for C$_{26}$H$_{30}$N$_2$O$_4$Si (M$^+$) 462.1974, found 462.1975; LRMS (EI) m/z 462 (M$^+$), 450, 361, 331, 304, 245, 223, 57.

Example 3.

Preparation of (20S)-7-tert-butyldiphenylsilylcamptothecin

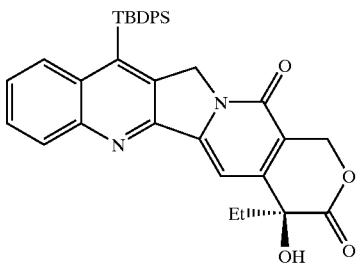

(1) (S)-4-Ethyl-4-hydroxy-6-iodo-3-oxo-7-(3-tert-butyldiphenylsilyl-2-propynyl)-1H-pyrano[3,4-c]-8-pyridone Following the procedure described in Example 1-(1), iodopyridone (2) (200 mg, 0.60 mmol) and 3-tert-butyldiphenylsilyl-2-propynyl bromide (428 mg, 1.20 mmol) provided, after flash-chromatography (CH$_2$Cl$_2$/AcOEt 9:1), 258 mg (70%) of a white foam: [α]$_D^{20}$+45.1 (c 0.2, CHCl$_3$); IR (CHCl$_3$, cm$^{-1}$) 3546, 2928, 2855, 1741, 1658, 1526; $^1$H NMR (300 MHz, CDCl$_3$) δ0.97 (t, J=7.3 Hz, 3 H), 1.08 (s, 9 H), 1.80 (m, J=7.1 Hz, 2 H), 3.76 (br s, 1 H), 5.13 (d, J=16.4 Hz, 1 H), 5.29 (d, J=2.5 Hz, 2 H), 5.52 (d, J=16.4 Hz, 1 H), 7.22 (s, 1 H), 7.32–7.40 (m, 6 H), 7.76–7.78 (m, 4 H); $^{13}$C NMR (75 MHz, CDCl$_3$) δ7.6, 18.6, 27.0, 31.6, 44.6, 60.4, 66.3, 71.8, 86.5, 99.9, 102.2, 116.6, 127.7, 129.6, 132.6, 135.6, 148.7, 157.8, 173.2; HRMS (EI) m/z calcd for C$_{25}$H$_{21}$INO$_4$Si (M-C$_4$H$_9^+$) 554.0279, found 554.0285; LRMS (EI) m/z 554 (M-C$_4$H$_9^+$), 587, 510, 220, 143, 105.

(2) (20S)-7-tert-butyldiphenylsilylcamptothecin

Following the procedure described in Example 1-(2), the compound prepared in (1) (61.1 mg, 0.10 mmol) yielded, after flash-chromatographies (CH$_2$Cl$_2$/MeOH 96:4; CH$_2$Cl$_2$/acetone 9:1), 26.5 mg (45%) of a light yellow solid: [α]$_D^{20}$+ 35.2 (c 0.2, CHCl$_3$); IR (CHCl$_3$, cm$^{-1}$) 3003, 2984, 2969, 2958, 2935, 1741, 1658, 1599, 1555, 1428, 1226, 1216, 1158, 1102; $^1$H NMR (300 MHz, CDCl$_3$) δ1.00 (t, J=7.3 Hz, 3 H), 1.44 (s, 9 H), 1.84 (m, 2 H), 3.75 (s, 1 H), 4.21 (d, J=5.7 Hz, 2 H), 5.19 (d, J=16.3 Hz, 1 H), 5.64 (d, J=16.3 Hz, 1 H), 7.43 (m, 5 H), 7.51 (t, J 7.3 Hz, 2 H), 7.62 (s, 1 H), 7.69 (m, 5 H), 8.10 (d, J=8.5 Hz, 1 H), 8.22 (d, J=8.2 Hz, 1 H); $^{13}$C NMR (75 MHz, CDCl$_3$) δ7.9, 20.4, 30.2, 31.6, 52.2, 66.4, 72.8, 97.5, 118.2, 126.3, 128.6, 129.8, 130.3, 130.7, 131.9, 132.2, 134.6, 134.64, 136.4, 136.5, 138.1, 140.9, 146.2, 148.4, 149.9, 151.3, 157.1, 174.1; HRMS (EI) m/z calcd for C$_{36}$H$_{34}$N$_2$O$_4$Si (M$^+$) 586.2281, found 586.2288; LRMS (EI) m/z 586 (M$^+$), 542, 529, 485, 428, 407, 321, 181, 131, 69.

Example 4

Figure 3:
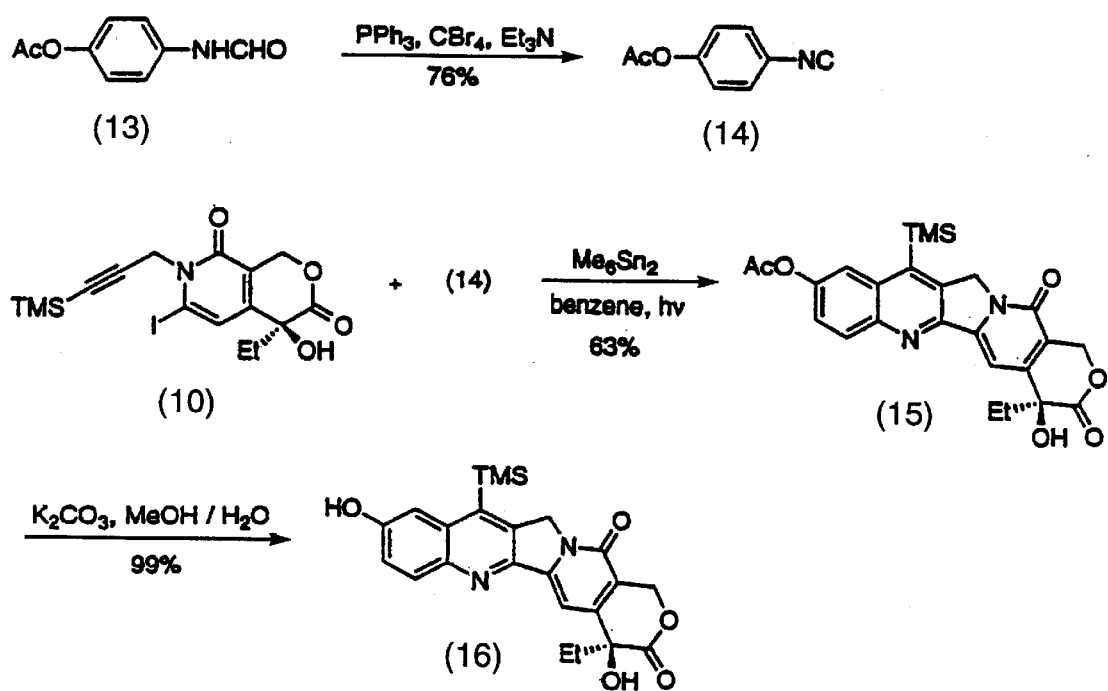
FIG. 3 is an illustration of a synthesis of (20S)-10-acetoxy-7-trimethylsilylcamptothecin and (20S)-10-hydroxy-7-trimethylsilylcamptothecin.
Figure 4:
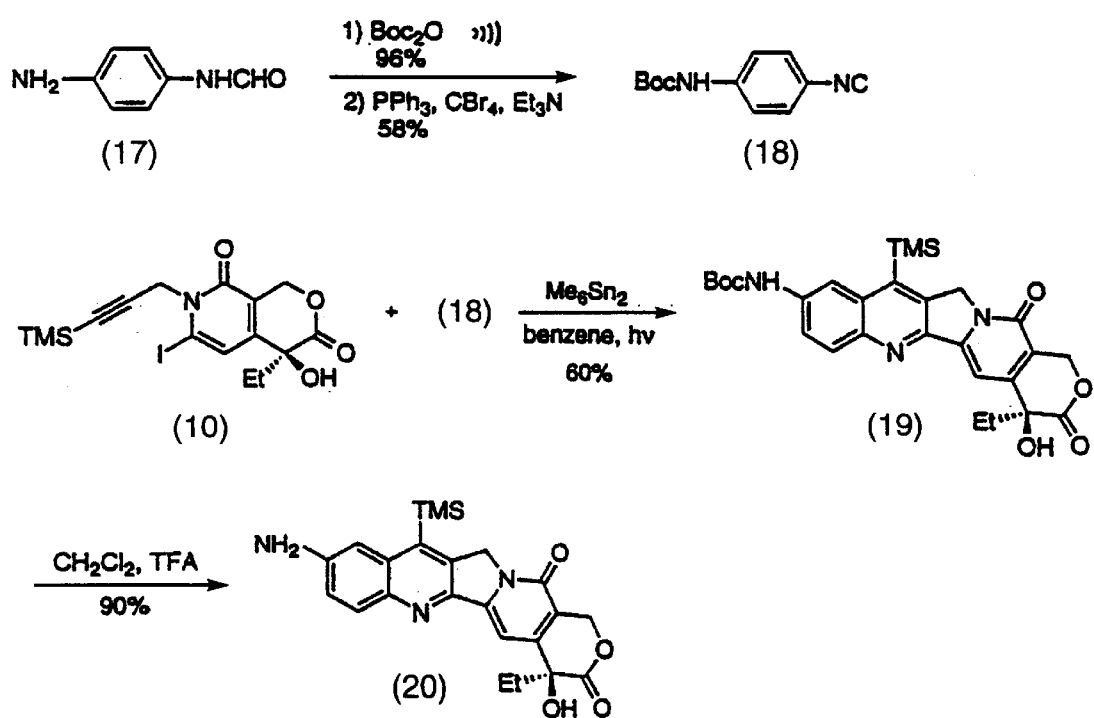
FIG. 4 is an illustration of a synthesis of (20S)-10-amino-7-trimethylsilylcamptothecin.

Preparation of (20S)-10-acetoxy-7-trimethylsilylcamptothecin (see FIG. 3)

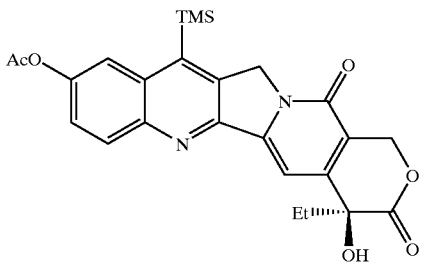

(1) 4-Acetoxyphenyl Isonitrile (14)

To a solution of 4-acetoxyformanilide (13) (358 mg, 1.0 mmol) in $CH_2Cl_2$ (10 mL) at 0° C. were successively added tetrabromomethane (0.70 g, 2.1 mmol), triphenylphosphine (525 mg, 2.1 mmol), and triethylamine (320 mL, 2.1 mmol), and the resulting mixture was refluxed in the dark for 3 h. After evaporation of the solvents, the crude was triturated in ice-cooled $Et_2O$ (20 mL) and filtered. The solvent was evaporated and the residue was purified by flash-chromatography (hexanes/AcOEt 8:2) to afford 243 mg (76%) of a slightly brown solid: IR (neat, cm$^{-1}$) 2127, 1768, 1501, 1370, 1201, 1180, 909; $^1$H NMR (300 MHz, $CDCl_3$) $\delta$2.29 (s, 3 H), 7.11 (d, J=8.8 Hz, 2 H), 7.38 (d, J=8.8 Hz, 2 H); $^{13}$C NMR (75 MHz, $CDCl_3$) $\delta$21.0, 122.8, 127.6, 150.8, 164.3, 168.8; HRMS (EI) m/z calcd for $C_9H_7NO_2$ (M$^+$) 161.0477, found 161.0474; LRMS (EI) m/z 161 (M$^+$), 133, 119, 91.

(2) (20S)-10-Acetoxy-7-trimethylsilylcamptothecin (15)

Following the procedure described in Example 1-(2), the compound prepared in Example 1-(1) (44.5 mg, 0.10 mmol) and the compound prepared in (1) (48.3 mg, 0.30 mmol) provided, after flash-chromatography ($CHCl_3$/acetone 10:1), 29.9 mg (63%) of a slightly yellow oil: $[\alpha]_D^{20}$+29.9 (c 0.5, $CHCl_3$); $^1$H NMR (300 MHz, $CDCl_3$) $\delta$0.61 (s, 9 H), 0.98 (t, J=7.4 Hz, 3 H), 1.86 (m, 2 H), 2.38 (s, 3 H), 4.13 (br s, 1 H), 5.24 (d, J=16.4 Hz, 1 H), 5.27 (s, 2 H), 5.68 (d, J=16.4 Hz, 1 H), 7.46 (dd, J=9.2, 2.5 Hz, 1 H), 7.60 (s, 1 H), 7.96 (d, J=2.5 Hz, 1 H), 8.13 (d, J=9.2 Hz, 1 H); $^{13}$C NMR (75 MHz, $CDCl_3$) $\delta$1.4, 7.8, 21.4, 31.5, 51.7, 66.2, 97.6, 118.3, 118.9, 124.6, 132.1, 135.0, 145.7, 146.1, 148.9, 150.1, 150.7, 157.3, 169.1, 173.7; HRMS (EI) m/z calcd for $C_{25}H_{26}N_2O_6Si$ (M$^+$) 478.1560, found 478.1582; LRMS (EI) m/z 478 (M$^+$), 436, 392, 377, 336, 277.

Example 5

Preparation of (20S)-10-hydroxy-7-trimethylsilylcamptothecin (16)

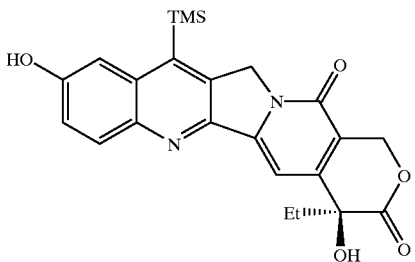

A solution of the compound (15) prepared in Example 5-(2) (16.8 mg, 0.035 mmol) and $k_2CO_3$ (9.6 mg, 0.070 mmol) in MeOH (100 mL) and $H_2O$ (100 mL) was stirred 1 h 30 at room temperature. The reaction mixture was acidified with AcOH (2 drops), diluted with brine (10 mL) and extracted with AcOEt (10×10 mL). The combined organic layers were dried ($Na_2SO_4$) and evaporated, and the residue was purified by flash-chromatographies ($CHCl_3$/MeOH/AcOH 90:10:2; $CHCl_3$/acetone 2:1) to give 15.1 mg (99%) of a white solid: $[\alpha]_D^{20}$+18.9 (c 0.2, $CHCl_3$/MeOH 4:1); $^1$H NMR (300 MHz, $CDCl_3/CD_3OD$ 4:1) $\delta$0.45 (s, 9 H), 0.84 (t, J=7.3 Hz, 3 H), 1.75 (m, 2 H), 5.12 (br s, 2 H), 5.12 (d, J=16.3 Hz, 1 H), 5.48 (d, J=16.3 Hz, 1 H), 7.24 (dd, J=9.1, 2.5 Hz, 1 H), 7.39 (d, J=2.5 Hz, 1 H), 7.87 (d, J=9.1 Hz, 1 H); $^{13}$C NMR (75 MHz, $CDCl_3/CD_3OD$ 4:1) $\delta$0.8, 7.4, 31.1, 51.8, 65.7, 97.5, 109.8, 117.5, 122.3, 131.3, 133.7, 134.6, 141.7, 142.6, 146.3, 147.5, 151.1, 156.3, 157.6; HRMS (EI) m/z calcd for $C_{23}H_{24}N_2O_5Si$ (M$^+$) 436.1454, found 436.1450; LRMS (EI) m/z 436 (M$^+$), 392, 377, 336, 323.

Reaction of this compound with $NH_2CH_2CH_2NMe_2$ followed by EtCOCl provided the open E-ring analog for biological testing.

Example 6

Figure 6:
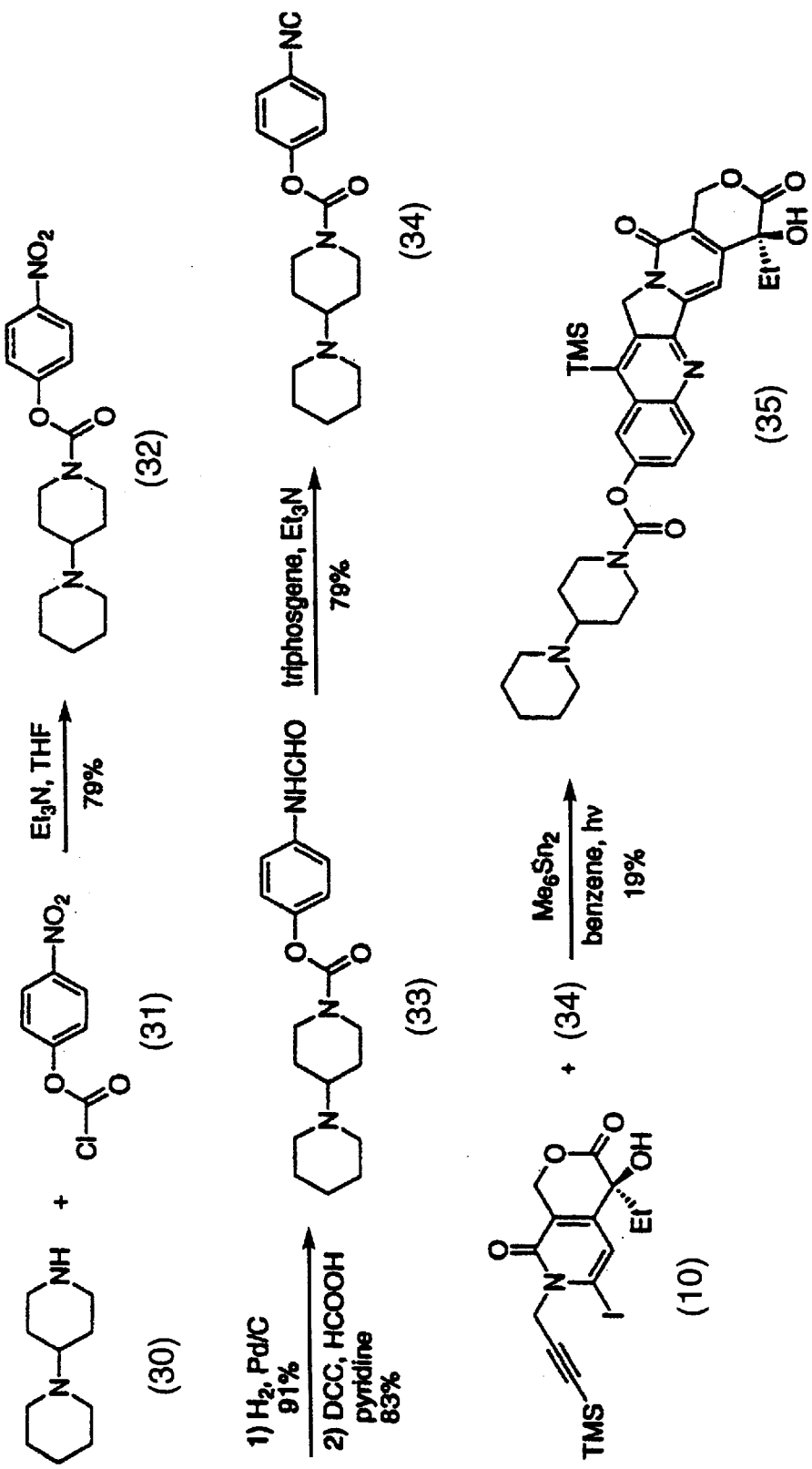
FIG. 6 is an illustration of a synthesis of a novel analog of irinotecan.

Preparation of (20S) 7-trimethylsilyl-irinotecan (see FIG. 6)

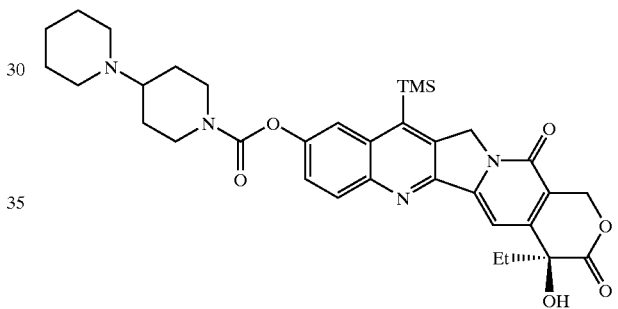

(1) [1,4'] Bipiperidinyl-1'-carboxylic acid 4-nitrophenylester (32)

To a solution of 4-nitrophenyl chloroformate (31) (5.15 g, 25.6 mmol) in 150 mL of dry THF at −78° C. was added triethylamine (10.7 mL, 76.2 mmol), followed by a solution of 4-piperidinopiperidine (30) (4.51 g, 25.6 mmol) in 40 mL of THF. This solution was stirred for two hours, after which the solvent was removed, and the residue was taken up in AcOEt, filtered and evaporated. The crude yellow solid was passed through a pad of neutral alumina using AcOEt as an eluent to yield, after evaporation, 6.73 g (79%) of a white solid: IR ($CHCl_3$, cm$^{-1}$) 3046, 2937, 2859, 1704, 1620, 1513, 1466, 1242, 1197; $^1$H NMR (300 MHz, $CDCl_3$) $\delta$1.20–1.80 (m, 8 H), 1.90 (d, J=12.7 Hz, 2 H), 2.20–2.70 (m, 5 H), 2.87 (t, J=12 Hz, 1 H), 3.01 (t, J=12 Hz, 1 H), 4.30 (br s, 2 H), 7.29 (d, J=9 Hz, 2 H), 8.26 (d, J=9 Hz, 2 H); $^{13}$C NMR (75 MHz, $CDCl_3$) $\delta$24.6, 26.3, 27.5, 28.2, 40.1, 44.4, 50.1, 62.0, 122.2, 124.9, 144.8, 151.9, 156.3; HRMS (EI) m/z calcd for $C_{17}H_{23}N_3O_4$ (M$^+$) 333.1676, found 333.1688; LRMS (EI) m/z 333 (M$^+$), 195, 167, 124, 110, 96, 55.

(2) [1,4'] Bipiperidinyl-1'-carboxylic acid 4-aminophenylester

To a solution of the compound prepared in (1) (1.012 g, 3.03 mmol) in AcOEt (125 ml) was added 10% Pd/C (0.15 g). The system was purged several times with argon, and a 1 L balloon of $H_2$ was added. After stirring the resulting mixture at room temperature for 12 hours, the catalyst was removed by filtration through celite and the solvent was evaporated to give 835 mg (91%) of a white solid: IR (CHCl$_3$, cm$^{-1}$) 3453, 3400, 3028, 2936, 2859, 1703, 1513, 1429, 1242, 1226, 1210, 1197; $^1$H NMR (300 MHz, CDCl$_3$) $\delta$1.30–1.70 (m, 8 H), 1.86 (d, J=12.6 Hz, 2 H), 2.33–2.62 (m, 5 H), 2.68–3.04 (m, 2 H), 3.58 (br s, 2 H), 4.30 (br s, 2 H), 6.64 (d, J=6.0 Hz, 2 H), 6.87 (d, J=6.0 Hz, 2 H); $^{13}$C NMR (75 MHz, CDCl$_3$) $\delta$24.6, 26.3, 27.5, 28.1, 43.8, 43.9, 50.1, 62.3, 115.4, 122.3, 143.4, 143.7, 154.1; HRMS (EI) m/z calcd for C$_{17}$H$_{25}$N$_3$O$_2$ (M$^+$) 303.1944 , found 303.1947; LRMS (EI) m/z 303 (M$^+$), 195, 167, 124, 108, 96, 80, 65, 55.

(3) [1,4'] Bipiperidinyl-1'-carboxylic acid 4-formylaminophenylester (33)

To a stirred solution of dicyclohexylcarbodiimide (272 mg, 1.32 mmol) in CH$_2$Cl$_2$ (5 mL) at 0° C. was added 98% formic acid (60.7 mg, 1.32 mmol) dropwise. After 10 minutes, the resulting mixture was added via syringe to a solution of the compound prepared in Example (2) (200 mg, 0.66 mmol) in pyridine (5 mL) at 0° C. The reaction mixture was then allowed to warm to room temperature and stirred 3 h. The pyridine solvent was evaporated and the residue was taken up in CH$_2$Cl$_2$, filtered, evaporated and subjected directly to a basic alumina column (CH$_2$Cl$_2$/MeOH 95:5) to give 118 mg (83%) of a white solid, which consists, at room temperature, of a mixture of the cis and trans rotamers originating from hindered rotation around the formamide carbon-nitrogen bond: IR (CHCl$_3$, cm$^{-1}$) 3025, 3013, 2937, 2888, 2861, 1703, 1517, 1466, 1275, 1226, 1210; $^1$H NMR (300 MHz, CDCl$_3$) $\delta$1.38–1.80 (m, 8 H), 1.90 (d, J=12 Hz, 2 H), 2.40–2.70 (m, 5 H), 2.83 (t, J=12 Hz, 1 H), 2.97 (t, J=12 Hz, 1 H), 4.32 (m, 2 H), 7.03–7.11 (m, 3 H), 7.37 (br s, 0.5 H) (cis), 7.46 (d, J=10 Hz, 1 H), 7.53 (d, J=11 Hz, 0.5 H) (trans), 8.32 (d, J=2 Hz, 0.5 H) (cis), 8.59 (d, J=11 Hz, 0.5 H) (trans); $^{13}$C NMR (75 MHz, CDCl$_3$) $\delta$24.6, 26.3, 27.6, 28.1, 44.2, 44.0, 50.1, 82.2, 120.0, 121.0, 122.1, 123.0, 133.9, 134.3, 147.5, 148.9, 153.9, 153.4, 159.1, 162.5; HRMS (EI) m/z calcd for C$_{18}$H$_{25}$N$_3$O$_3$ (M$^+$) 331.1884, found 331.1896; LRMS (EI) m/z 331 (M$^+$), 244, 202, 167, 124, 80, 55.

(4) [1,4'] Bipiperidinyl-1'-carboxylic acid 4-isonitrilophenylester (34)

To a solution of the compound prepared in Example (3) (90.1 mg, 0.272 mmol) in CH$_2$Cl$_2$ (10 mL) were successively added triethylamine (69.5 mg, 0.688 mmol) them dropwise, at 0° C., a solution of triphosgene (68 mg, 0.229 mmol) in dry CH$_2$Cl$_2$ (10 mL). The mixture was stirred 2 hours at room temperature, washed with 7% NaHCO$_3$ (5 mL) and dried (MgSO$_4$). The crude brown residue obtained after evaporation of the solvent was subjected to flash-chromatography (Et$_2$O/Et$_2$NH 95:5) to yield 67.2 mg (79%) of a white solid: IR (CHCl$_3$, cm$^{-1}$) 3034, 2937, 2131, 1718, 1504, 1429, 1233, 1224, 1213, 1198, 1184; $^1$H NMR (300 MHz, CDCl$_3$) $\delta$1.32–1.75 (m, 8 H), 1.90 (br d, J=12.4 Hz, 2 H), 2.32–2.65 (m, 5 H), 2.84 (t, J=12.3 Hz, 1 H), 2.98 (t, J=12.1 Hz, 1 H), 4.20–4.40 (m, 2 H), 7.14 (d, J=8.8 Hz, 2 H), 7.37 (d, J=8.8 Hz, 2 H); $^{13}$C NMR (75 MHz, CDCl$_3$) $\delta$25.0, 26.5, 27.8, 28.5, 44.4, 50.6, 62.7, 123.3, 127.8, 152.1, 153.1, 164.4; HRMS (EI) m/z calcd for C$_{18}$H$_{23}$N$_3$O$_2$ (M$^+$) 313.1779, found 313.1790; LRMS (EI) m/z 313 (M$^+$), 195, 167, 124 ,110, 84, 55.

(5) (20S)-7-Trimethylsilyl-Irinotecan (35)

Following the procedure described in Example 1-(2), the compound prepared in Example 1-(1) (44.5 mg, 0.10 mmol), the compound prepared in (4) (93.9 mg, 0.3 mmol), and hexamethylditin (50 mg, 0.15 mmol) in dry benzene (1.5 mL) were irradiated for 9 hours at 70° with a 275W GE sunlamp. The reaction was evaporated, dissolved in MeOH with a few drops of DMSO to aid solubility and injected into a Waters reverse phase HPLC. The conditions used to effect separation were as follows. A Waters 600E system controller with a Waters 490E Programmable multiwavelength detector, a Sargent Welch plotter and Waters C-18 25×10 cartridge columns were employed. A gradient elution, [5:95 MeCN/H$_2$O (0.1% TFA) to 30:70 MeCN/H$_2$O (0.1% TFA)], over 40 minutes time at 20 mL/min gave a semipurified grey solid after lyophilization. The grey solid was further purified (CH$_2$Cl$_2$/EtOH 70:30) on a chromatotron using a 1 mm plate to give 12 mg (19%) of a yellow solid: [α]$_D^{20}$+14.8 (c 0.2, CHCl$_3$); IR (CHCl$_3$, cm$^{-1}$) 3023, 2957, 2933, 1720, 1659, 1601, 1216, 1191, 1175, 1158; $^1$H NMR (300 MHz, CDCl$_3$) $\delta$0.64 (s, 9 H), 1.03 (t, J=7.3 Hz, 3 H), 1.50–1.51 (br m, 2 H), 1.51–1.52 (br m, 6 H), 1.84 (m, J=7.3 Hz, 2 H), 2.01–2.10 (br m, 2 H), 2.60–2.75 (br s, 5 H), 2.75–3.12 (br m, 2 H), 4.30–4.50 (br m, 2 H), 5.30 (d, J=16.3 Hz, 1 H), 5.31 (s, 2 H), 5.74 (d, J=16.3 Hz, 1 H), 7.55 (dd, J=9.0, 2.4 Hz, 1 H), 7.63 (s, 1 H), 8.01 (d, J=2.3 Hz, 1 H), 8.19 (d, J=9 Hz, 1 H); $^{13}$C NMR (75 MHz, CDCl$_3$) $\delta$1.5, 7.8, 25.4, 29.7, 31.5, 43.8, 50.1, 51.8, 62.5, 66.3, 72.8, 97.5, 118.1, 119.0, 125.1, 132.0, 132.3, 134.9, 143.4, 145.6, 146.4, 150.1, 150.5, 152.8, 157.4, 174.0; HRMS (EI) m/z calcd for C$_{34}$H$_{42}$N$_4$O$_6$Si (M$^+$) 630.2898, found 630.2874; LRMS (EI) m/z 630 (M$^+$), 586, 501, 457, 195, 167, 153, 124, 111, 96, 84.

Example 7

Preparation of (20S)-11-fluoro-7-trimethylsilylcamptothecin (see FIG. 2)

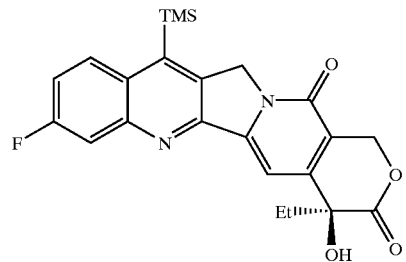

(1) 3-Fluoro-2-trimethylsilylbenzaldehyde (7)

The preparation of 3-fluoro-2-trimethylsilylbenzaldehyde proceeds through a selective ortho-metallation. See Comins, D. L. et al., J. Org. Chem., 49, 1078 (1984). See also Snieckus, V., Chem. Rev., 90, 879 (1990). To a solution of N,N,N'-trimethylethylenediamine (2.70 mL, 20 mmol) in THF (50 mL) was slowly added 1.6 N n-BuLi in hexanes (13 mL, 21 mmol) at −20° C., followed by 3-fluorobenzaldehyde (2.10 mL, 20 mmol) 15 min latter. After 15 minute at this temperature, 1.6 N n-BuLi in hexanes (38 mL, 60 mmol) was injected and the solution was stirred 1 h 30 at −35° C. Chlorotrimethylsilane (15 mL, 120 mmol) was added and the reaction mixture was stirred overnight at room temperature. The final solution was poured into ice-cooled 1 N HCl (150 mL), quickly extracted with Et$_2$O (3×100), washed with brine and dried (Na$_2$SO$_4$). After evaporation of the solvents, the residue was purified by flash-chromatography (hexanes/AcOEt 95:5) to provide 3.25 g (83%) of an oil: IR (neat, cm$^{-1}$) 1701, 1440, 1252, 1233, 1109, 848, 764; $^1$H NMR (300 MHz, CDCl$_3$) $\delta$0.40 (d, J=2.6 Hz, 9 H), 7.18 (br t, J=9.0 Hz, 1 H), 7.47 (ddd, J$_1$=J$_2$=8.1 Hz, J$_3$=5.4 Hz, 1 H), 7.70 (br d, J=7.5 Hz, 1 H); $^{13}$C NMR (75 MHz, CDCl$_3$) $\delta$1.8, 120.8 (d, J$_{CF}$=29 Hz), 126.8, 128.2, 131.2, 143.3, 167.6 (d, J$_{CF}$=244 Hz), 192.4; HRMS (EI) m/z calcd for C$_9$H$_{10}$FOSi (M-CH$_3^+$) 181.0485, found 181.0482; LRMS (EI) m/z 181 (M-CH$_3^+$), 151, 125, 103, 91.

(2) 3-Fluoro-2-trimethylsilylbenzoic acid

A classical oxidation to the free acid was then performed. See Hill, L. R. et al., *J. Org. Chem.*, 50, 470 (1985). To a solution of the compound prepared in (1) (3.41 g, 17.3 mmol) in tert-butanol (20 mL) were successively added a 2 N solution of 2-methyl-2-butene in THF (55 mL, 110 mmol) then slowly, over a period of 10 minutes, a solution of 80% $NaClO_2$ (2.55 g, 22.5 mmol) and $NaH_2PO_4 \cdot H_2O$ (3.10 g, 22.5 mmol) in water (18 mL). The resulting mixture was stirred 16 h at room temperature, the tert-butanol was evaporated, and the residue was taken up in 1 N NaOH (50 mL) and washed with hexanes (3×20 mL). The aqueous layer was acidified with 1 N HCl to pH 2, saturated with NaCl, and extracted with $Et_2O$ (3×50 mL). The combined organic layers were dried ($Na_2SO_4$) and evaporated to provide 3.13 g (85%) of a white solid: IR (NaCl, $cm^{-1}$) 2982, 1700, 1434, 1294, 1271, 1253, 1230, 849, 763; $^1H$ NMR (300 MHz, $CDCl_3$) δ0.39 (d, J=2.6 Hz, 9 H), 7.16 (br t, J=9.1 Hz, 1 H), 7.41 (ddd, $J_1=J_2=7.9$ Hz, $J_3=5.6$ Hz, 1 H), 7.73 (br d, J=7.7 Hz, 1 H); $^{13}C$ NMR (75 MHz, $CDCl_3$) δ1.3, 119.5 (d, $J_{CF}=27$ Hz), 126.0, 127.3, 130.9, 138.0, 167.5 (d, $J_{CF}=243$ Hz), 174.5; HRMS (EI) m/z calcd for $C_9H_{10}FO_2Si$ ($M-CH_3^+$) 197.0434, found 197.0433; LRMS (EI) m/z 197 ($M-CH_3^+$), 179, 133, 115, 105.

(3) 3-Fluoro-2-trimethylsilylphenyl isocyanate (8)

Preparation of the intermediate isocyanate was carried out via a Curtius rearrangement. See Capson, T. L. et al., *Tetrahedron Lett.*, 25, 3515 (1984) and references herein. To a solution of the compound prepared in (2) (3.03 g, 14.3 mmol) in $CH_2Cl_2$ (20 mL) was added oxalylchloride (1.30 mL, 15.0 mmol) and the resulting mixture was stirred 3 h at room temperature. The residue obtained after evaporation of the solvent was diluted with THF (10 mL) and injected with vigorous stirring to a ice-cooled solution of $NaN_3$ (3.70 g, 57 mmol) in $H_2O$ (20 mL) and acetone (50 mL). After 15 min at 0° C. and 1 min at room temperature, the solution was extracted with $Et_2O$ (4×50 mL) and dried ($Na_2SO_4$). The residue obtained after evaporation of solvents was refluxed in toluene for 1 h 30 to provide, upon solvent removal, 2.85 g (79%) of a slightly yellow oil: IR (neat, $cm^{-1}$) 2269, 1598, 1433, 1252, 1228, 846, 788; $^1H$ NMR (300 MHz, $CDCl_3$) δ0.38 (d, J=1.9 Hz, 9 H), 6.82 (br t, J=8.3 Hz, 1 H), 6.90 (br d, J=8.2 Hz, 1 H), 7.25 (ddd, $J_1=J_2=8.1$ Hz, $J_3=6.6$ Hz, 1 H); $^{13}C$ NMR (75 MHz, $CDCl_3$) δ0.4, 112.6 (d, $J_{CF}=26$ Hz), 120.5, 122.5, 131.5, 139.2, 167.4 (d, $J_{CF}=241$ Hz).

(4) 3-Fluoro-2-trimethylsilylphenyl isonitrile (9)

A deoxygenation then afforded the expected isonitrile. See Baldwin, J. E. et al., *Tetrahedron*, 39, 2989 (1983). Triethylamine (4.10 mL, 29.3 mmol) was added slowly at 0° C. to a 2 N solution of trichlorosilane in $CH_2Cl_2$ (8.40 mL, 16.8 mmol) followed, 5 min latter, by the compound prepared in Example (3) (2.35 g. 11.2 mmol). After 1 h 30 at 0° C. and 30 min at room temperature, the solution was saturated with $NH_3$, filtered over Celite, washed with 5% $NaH_2PO_4$ and dried ($Na_2SO_4$). The crude obtained after evaporation of the solvent was then subjected to flash-chromatography (hexanes/AcOEt 95:5) to afford 1.42 g (66%) of a slightly purple liquid: IR (neat, $cm^{-1}$) 2114, 1598, 1440, 1254, 1237, 1110, 943, 848, 793; $^1H$ NMR (300 MHz, $CDCl_3$) δ0.45 (d, J=1.8 Hz, 9 H), 7.01 (br t, J=8.3 Hz, 1 H), 7.17 (br d, J=7.7 Hz, 1 H), 7.32 (ddd, $J_1=J_2=8.0$ Hz, $J_3=6.1$ Hz, 1 H); $^{13}C$ NMR (75 MHz, $CDCl_3$) δ0.1, 116.5 (d, $J_{CF}=26$ Hz), 124.3, 131.6, 166.8 (d, $J_{CF}=243$ Hz), 166.9; HRMS (EI) m/z calcd for $C_{10}H_{12}FNSi$ ($M^+$) 193.0723, found 193.0715; LRMS (EI) m/z 193 ($M^+$), 178, 150, 116, 105.

(5) (20S)-11-Fluoro-7,12-bis(trimethylsilyl)camptothecin (11)

Following the procedure described in Example 1-(2), the compound prepared in Example 1-(1) (43.5 mg, 0.098 mmol) and the compound prepared in Example (4) (76 mg, 0.39 mmol) provided, after flash-chromatography ($CHCl_3$/acetone 20:1), 33.4 mg (67%) of a slightly yellow oil: $[\alpha]_D^{20}$+23.6 (c 0.2, $CHCl_3$); $^1H$ NMR (300 MHz, $CDCl_3$) δ0.53 (d, J=1.7 Hz, 9 H), 0.60 (s, 9 H), 1.02 (t, J=7.4 Hz, 3 H), 1.88 (m, 2 H), 3.82 (br s, 1 H), 5.28 (d, J=16.3 Hz, 1 H), 5.29 (br s, 2 H), 5.72 (d, J=16.3 Hz, 1 H), 7.31 (t, J=8.7 Hz, 1 H), 7.46 (s, 1 H), 8.18 (dd, J=9.2, 5.9 Hz, 1 H); $^{13}C$ NMR (75 MHz, $CDCl_3$) δ1.6, 1.7, 7.7, 31.4, 51.8, 66.3, 72.7, 97.2, 117.8 (d, $J_{CF}=33$ Hz), 124.3 (d, $J_{CF}=28$ Hz), 128.9, 131.1, 133.1, 144.4, 146.7, 150.1, 153.4, 157.4, 167.6 (d, $J_{CF}=245$ Hz), 173.9; HRMS (EI) m/z calcd for $C_{26}H_{31}FN_2O_4Si_2$ ($M^+$) 510.1806, found 510.1806; LRMS (EI) m/z 510 ($M^+$), 495, 466, 451, 395, 319.

(6) (20S)-11-Fluoro-7-trimethylsilylcamptothecin (12)

A solution of the compound prepared in Example (5) (19.5 mg, 0.038 mmol) in 48% HBr (1 mL) was heated at 50° C. for 20 h. The reaction mixture was slowly poured with vigorous stirring into saturated $NaHCO_3$ (10 mL), extracted with AcOEt (6×20 mL) and dried ($Na_2SO_4$). After evaporation of the solvent, the residue was purified by flash-chromatography ($CHCl_3$/acetone 8:1) to give 12.5 mg (83%) of a slightly yellow solid: $[\alpha]_D^{20}$+39.6 (c 0.2, $CHCl_3$); $^1H$ NMR (300 MHz, $CDCl_3$) δ0.62 (s, 9 H), 1.01 (t, J=7.4 Hz, 3 H), 1.87 (m, 2 H), 3.81 (br s, 1 H), 5.28 (d, J=16.4 Hz, 1 H), 5.28 (br s, 2 H), 5.72 (d, J=16.4 Hz, 1 H), 7.31 (ddd, J=9.6, 7.8, 2.8 Hz, 1 H), 7.61 (s, 1 H), 7.78 (dd, J=9.7, 2.7 Hz, 1 H), 8.19 (dd, J=9.4, 5.8 Hz, 1 H); $^{13}C$ NMR (75 MHz, $CDCl_3$) δ1.6, 7.8, 31.5, 51.7, 66.3, 72.7, 97.8, 114.3 (d, $J_{CF}=20$ Hz), 117.7 (d, $J_{CF}=26$ Hz), 118.5, 128.9, 130.0, 133.9, 144.4, 146.1, 149.3, 150.1, 151.7, 157.4, 162.6 (d, $J_{CF}=250$ Hz), 173.9; HRMS (EI) m/z calcd for $C_{23}H_{23}FN_2O_4Si$ ($M^+$) 438.1411, found 438.1412; LRMS (EI) m/z 438 ($M^+$), 409, 394, 379, 365, 338, 309.

Example 8

Preparation of (20S)-10-amino-7-trimethylsilylcamptothecin (see FIG. 4) (CHJ-792)

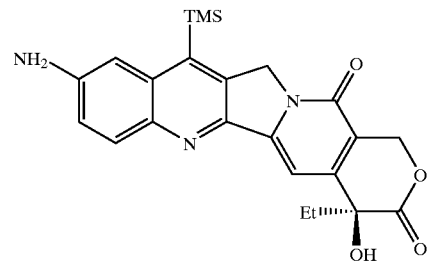

(1) 4-tert-Butyloxycarbonylaminophenyl isonitrile (18)

The isonitrile was prepared in 2 steps via classical Boc-protection followed by dehydration. See Einhorn, J. et al., *Synlett*, 37 (1991). A mixture of 4-aminoformanilide (1.71 g, 12.6 mmol), di-tert-butyl dicarbonate (2.87 g, 13.2 mmol) and $NaHCO_3$ (1.11 g, 13.2 mmol) in absolute EtOH (50 mL) was sonicated in a cleaning bath for 4 h. The final solution was filtered through a pad of Celite and concentrated to dryness. The residue was taken up in half brine (50 mL), extracted with AcOEt (6×30 mL) and dried ($Na_2SO_4$). After evaporation of the solvent, the residual oil was subjected to flash-chromatography ($CHCl_3$/MeOH 95:5) to give 2.85 g (96%) of 4-tert-butyloxycarbonylaminoformanilide, as a white solid. This intermediate (945 mg, 4.0 mmol) was subjected to the conditions described in Example 5-(1) to provide, after flash-chromatography (hexanes/AcOEt 9:1), 502 mg (58%) of a slightly brown solid: IR (NaCl, cm$^{-1}$) 3370, 2121, 1691, 1524, 1412, 1364, 1239, 1158, 832; $^1$H NMR (300 MHz, CDCl$_3$) $\delta$1.48 (s, 9 H), 6.75 (br s, 1 H), 7.26 (d, J=8.8 Hz, 2 H), 7.37 (d, J=8.8 Hz, 2 H); $^{13}$C NMR (75 MHz, CDCl$_3$) $\delta$28.2, 81.3, 118.5, 127.1, 139.4, 152.3, 162.7; HRMS (EI) m/z calcd for C$_{12}$H$_{14}$N$_2$O$_2$ (M$^+$) 218.1055, found 218.1044; LRMS (EI) m/z 218 (M$^+$), 162, 144.

(2) (20S)-10-tert-Butyloxycarbonylamino-7-trimethylsilyl camptothecin (19)

Following the procedure described in Example 1-(2), the compound prepared in Example 1-(1) (44.5 mg, 0.10=mol) and the compound prepared in Example (1) (65 mg, 0.30 mmol) provided, after flash-chromatography (CHCl$_3$/acetone 6:1), 32.5 mg (60%) of a slightly yellow solid: $[\alpha]_D^{20}$+28.0 (c 0.2, CHCl$_3$); $^1$H NMR (300 MHz, CDCl$_3$) $\delta$0.63 (s, 9 H), 0.99 (t, J=7.4 Hz, 3 H), 1.53 (s, 9 H), 1.86 (m, 2 H), 4.03 (br s, 1 H), 5.24 (d, J=16.2 Hz, 1 H), 5.26 (s, 2 H), 5.70 (d, J=16.2 Hz, 1 H), 7.00 (br s, 1 H), 7.47 (dd, J=9.2, 2.3 Hz, 1 H), 7.55 (s, 1 H), 8.02 (d, J=9.2 Hz, 1 H), 8.56 (br s, 1 H); $^{13}$C NMR (75 MHz, CDCl$_3$) $\delta$1.3, 7.8, 28.2, 31.5, 51.8, 66.3, 72.8, 97.1, 114.4, 117.8, 122.6, 131.3, 132.8, 135.0, 137.2, 142.9, 144.3, 146.6, 149.2, 150.1, 157.4, 173.9; HRMS (EI) m/z calcd for C$_{23}$H$_{25}$N$_3$O$_4$Si (M-Boc$^+$) 435.1614, found 435.1612; LRMS (EI) m/z 535 (M$^+$), 479, 435, 391, 362, 335.

(3) (20S)-10-Amino-7-trimethylsilylcamptothecin (20)

A solution of the compound prepared in Example (2) (75.5 mg, 0.141 mmol) and TFA (500 mL) in CH$_2$Cl$_2$ (2 mL) was stirred 3 h at room temperature. The reaction mixture was then poured into saturated NaHCO$_3$ (50 mL), extracted with AcOEt (10×15 mL) and dried (Na$_2$SO$_4$). The residue obtained after evaporation of the solvents was purified by flash-chromatography (CHCl$_3$/MeOH 95:5) to afford 55.4 mg (90%) of a yellow solid: $[\alpha]_D^{\circ}$+18.7 (c 0.15, CHCl$_3$/MeOH 4:1); $^1$H NMR (300 MHz, CDCl$_3$/CD$_3$OD 4:1) $\delta$ 0.40 (s, 9 H), 0.80 (t, J=7.4 Hz, 3 H), 1.70 (m, 2 H), 5.05 (s, 2 H), 5.08 (d, J=16.3 Hz, 1 H), 5.43 (d, J=16.3 Hz, 1 H), 7.05 (br s, 1 H), 7.07 (d, J=8.0 Hz, 1 H), 7.38 (s, 1 H), 7.74 (d, J=8.0 Hz, 1 H); $^{13}$C NMR (75 MHz, CDCl$_3$/CD$_3$OD 4:1) $\delta$0.6, 7.2, 30.8, 51.8, 65.5, 72.7, 97.0, 107.2, 116.8, 122.0, 130.7, 134.0, 134.7, 139.9, 141.7, 145.8, 146.9, 151.2, 157.5, 173.7; HRMS (EI) m/z calcd for C$_{23}$H$_{25}$N$_3$O$_4$Si (M$^+$) 435.1614, found 435.1613; LRMS (EI) m/z 435 (M$^+$), 391, 376, 335, 290.

Example 9

Preparation of (20S)-11-amino-7-trimethylsilylcamptothecin

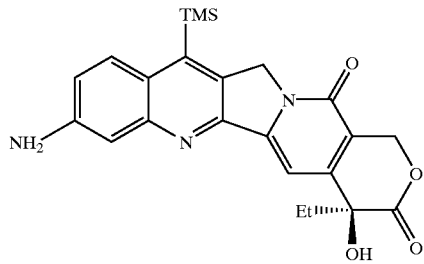

(1) 3-tert-Butyloxycarbonylaminophenyl isonitrile

The isonitrile was prepared in 2 steps following the same procedures as described in Example 9-(1). In the first step, the Boc-protection of 3-aminoformanilide (1.80 g, 13.2 mmol) provided, after flash-chromatography (CHCl$_3$/MeOH 95:5), 2.65 g (85%) of 3-tert-butyloxycarbonylaminoformanilide, as a white solid. This intermediate (412 mg, 1.74 mmol) was then subjected to the conditions described in Example 5-(1) to provide, after flash-chromatography (hexanes/AcOEt 9:1), 190 mg (50%) of a brown solid: IR (NaCl, cm$^{-1}$) 3318, 2126, 1715, 1603, 1547, 1433, 1236, 1162, 782; $^1$H NMR (300 MHz, CDCl$_3$) $\delta$1.49 (s, 9 H), 6.67 (br s, 1 H), 7.00 (m, 1 H), 7.20–7.30 (m, 2 H), 7.60 (br s, 1 H); $^{13}$C NMR (75 MHz, CDCl$_3$) $\delta$28.2, 81.3, 116.0, 118.9, 120.6, 129.8, 139.5, 152.3, 163.6; HRMS (EI) m/z calcd for C$_{12}$H$_{14}$N$_2$O$_2$ (M$^+$) 218.1055, found 218.1047; LRMS (EI) m/z 218 (M$^+$), 196, 162, 152, 118.

(2) (20S)-11-Amino-7-trimethylsilylcamptothecin

Following the procedure described in Example 1-(2), the compound prepared in Example 1-(1) (44.5 mg, 0.10 mmol) and the compound prepared in Example (1) (65.5 mg, 0.3 mmol) afforded, after flash-chromatographies (CHCl$_3$/MeOH 95:5; CHCl$_3$/acetone 5:1), 23.1 mg (43%) of a slightly yellow oil. This intermediate (14.7 mg, 0.027 mmol) was then deprotected following the conditions described in Example 9-(3) to provide, after flash-chromatography (CHCl$_3$/MeOH 9:1), 11.8 mg (99%) of (20S)-11-amino-7-trimethylsilylcamptothecin, as a yellow solid and with the exclusion of other isomers: $[\alpha]_D^{20}$+15.0 (c 0.1, CHCl$_3$/MeOH 4:1); $^1$H NMR (300 MHz, CDCl$_3$/CD$_3$OD 4:1) $\delta$0.44 (s, 9 H), 0.86 (t, J=7.4 Hz, 3 H), 1.76 (m, 2 H), 5.08 (s, 2 H), 5.14 (d, J=16.4 Hz, 1 H), 5.50 (d, J=16.3 Hz, 1 H), 6.97 (dd, J=9.2, 2.5 Hz, 1 H), 7.07 (d, J=2.5 Hz, 1 H), 7.50 (s, 1 H), 7.84 (d, J=9.2 Hz, 1 H); $^{13}$C NMR (75 MHz, CDCl$_3$/CD$_3$OD 4:1) $\delta$1.1, 7.4, 31.0, 51.7, 65.6, 97.9, 107.9, 117.8, 119.7, 125.9, 127.1, 129.0, 130.4, 135.4, 144.3, 149.5, 149.9, 151.1, 157.6, 175.3; HRMS (EI) m/z calcd for C$_{23}$H$_2$SN$_3$O$_4$Si (M$^+$) 435.1614, found 435.1626; LRMS (EI) m/z 435 (M$^+$), 406, 391, 376, 335.

Example 10

Figure 5:
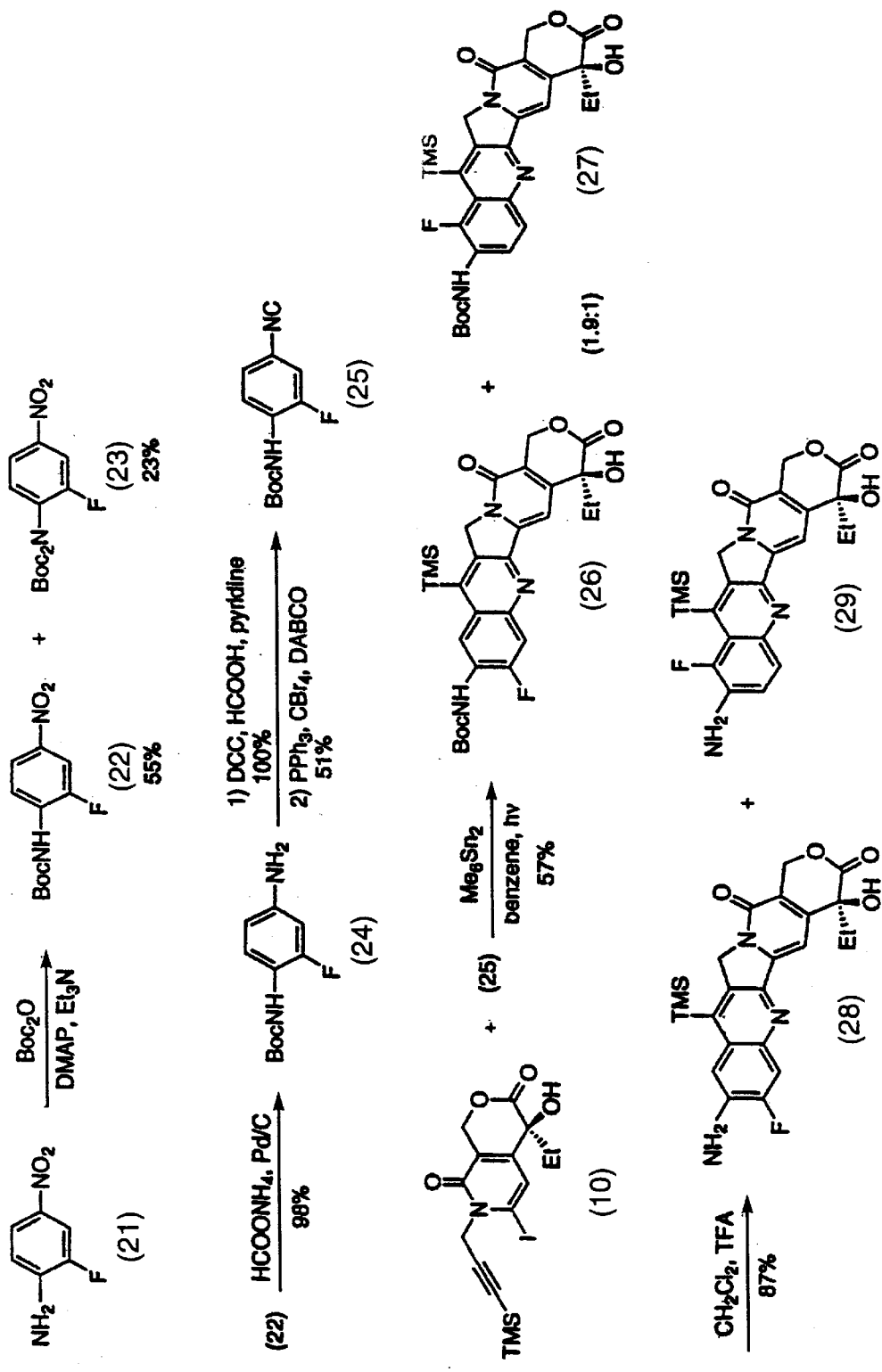
FIG. 5 is an illustration of a synthesis of (20S)-10-amino-11-fluoro-7-trimethylsilylcamptothecin.

Preparation of (20S)-11-fluoro-10-amino-7-trimethylsilylcamptothecin (see FIG. 5)

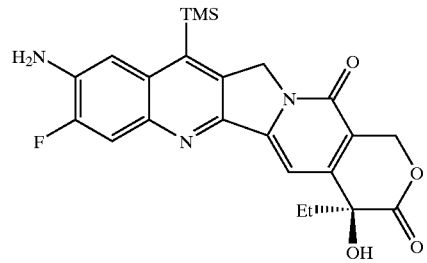

(1) 4-tert-Butyloxycarbonylamino-3-fluoro-1-nitrobenzene (22)

To a solution of 2-fluoro-4-nitroaniline (21) [prepared according to Katritsky, A. R. et al., *J. Org. Chem.*, 51, 5039 (1986)] (2.16 g, 13.9 mmol) in CH$_2$Cl$_2$ (25 mL) were successively added di-tert-butyl dicarbonate (3.19 g, 14.6 mmol), triethylamine (2.95 mL, 20.8 mmol) and 4-dimethylaminopyridine (210 mg, 1.67 mmol) and the reaction mixture was stirred 16 h at room temperature. The final solution was diluted with CH$_2$Cl$_2$ (75 mL), washed with ice-cooled 5% citric acid (4×50 mL) and dried (Na$_2$SO$_4$). After evaporation of the solvent, the residue was subjected to flash-chromatography (Hexanes/AcOEt 9:5) to provide, in order of elution, first 1.95 g (55%) of the mono-protected derivative, 4-tert-butyloxycarbonylamino-3-fluoro-1-nitrobenzene, secondly 1.13 g (23%) of the bis-protected derivative, 4-di-tert-butyloxycarbonylamino-3-fluoro-1-nitrobenzene. The characteristics of the mono-protected derivative are as follows: $^1$H NMR (300 MHz, CDCl$_3$) $\delta$1.52 (s, 9 H), 6.99 (br s, 1 H), 7.95 (m, 1 H), 8.03 (br d, J=9.2 Hz, 1 H), 8.34 (br t, J=8.5 Hz, 1 H); $^{13}$C NMR (75 MHz, CDCl$_3$) $\delta$28.1, 82.5, 110.9 (d, $J_{CF}$=23 Hz), 118.3, 120.8, 133.5, 141.7, 150.1 (d, $J_{CF}$=243 Hz), 151.4; HRMS (EI) m/z calcd for C$_{11}$H$_{13}$FN$_2$O$_4$ (M$^+$) 256.0859, found 258.0854; LRMS (EI) m/z 256 (M$^+$), 200, 182, 57.

(2) 4-tert-Butyloxycarbonylamino-3-fluoroaniline (24)

Reduction of the nitro group to the amine function was carried out following a classical procedure. See Ram, S. et al., *Tetrahedron Lett.*, 25, 3415 (1984). To a solution of the compound prepared in Example (1) (1.62 g, 6.32 mmol) and ammonium formate (1.70 g, 27 mmol) in anhydrous MeOH (12 mL) was added 10% Pd-C (400 mg) in one portion. After 2 h at room temperature, the final solution was filtered over Celite, concentrated and the residue was directly subjected to flash-chromatography (CHCl$_3$/MeOH 9:1) to provide 1.40 g (98%) of a slightly yellow oil: $^1$H NMR (300 MHz, CD$_3$SOCD$_3$) $\delta$1.40 (s, 9 H), 5.22 (s, 2 H), 6.25–6.35 (m, 2 H), 6.93 (br t, J=8.0 Hz, 1 H), 8.29 (br s, 1 H); $^{13}$C NMR (75 MHz, CDCl$_3$) $\delta$28.5, 80.4, 102.1 (d, $J_{CF}$=24 Hz), 110.7, 117.2, 122.8, 143.4, 153.1, 154.1 (d, $J_{CF}$=244 Hz); HRMS (EI) m/z calcd for C$_{11}$H$_{15}$FN$_2$O$_2$ (M$^+$) 226.1118, found 226.1116; LRMS (EI) m/z 226 (M$^+$), 170, 126, 83, 57.

(3) 4-tert-Butyloxycarbonylamino-3-fluorophenyl isonitrile (25)

To a stirred solution of dicyclohexylcarbodiimide (1.51 g, 7.31 mmol) in CH$_2$Cl$_2$ (15 mL) at 0° C. was added formic acid (275 mL, 7.31 mmol) dropwise. After 10 minutes, the resulting mixture was added over a period of 5 minutes to a solution of the compound prepared in Example (2) (1.28 g, 5.66 mmol) in CH$_2$Cl$_2$ (10 mL) and pyridine (0.61 mL, 7.50 mmol) at 0° C. The reaction mixture was then allowed to warm to room temperature and stirred 16 h. After filtration over Celite, the final solution was concentrated and subjected to flash-chromatography (CHCl$_3$/AcOEt 85:15) to give 1.44 g (100%) of 4-tert-butyloxycarbonylamino-3-fluoroformamide, as a white solid. This intermediate (1.38 g, 5.43 mmol) was dissolved in CH$_2$Cl$_2$ (20 mL) and, at 0° C., were successively added tetrabromomethane (1.93 g, 5.80 mmol), triphenylphosphine (1.52 g, 5.80 mmol), and 1.4-diazabicyclo[2.2.2]octane (DABCO, 650 mg, 5.80 mmol). The reaction mixture was allowed to warm to room temperature and stirred 2 h. After evaporation of the solvent, the crude was triturated in ice-cooled Et$_2$O (20 mL) and filtered over Celite. The residue obtained after evaporation of the solvent was purified by flash-chromatography (hexanes/AcOEt 95:5 to 9:1) to provide 660 mg (51%) of a slightly brown solid: $^1$H NMR (300 MHz, CDCl$_3$) $\delta$1.51 (s, 9 H), 6.76 (br s, 1 H), 7.05–7.20 (m, 2 H), 8.17 (br t, J=8.6 Hz, 1 H); $^{13}$C NMR (75 MHz, CDCl$_3$) $\delta$28.1, 81.8, 113.3 (d, $J_{CF}$=25 Hz), 119.7, 123.0, 128.6, 150.6 (d, $J_{CF}$=242 Hz), 151.8, 164.2; HRMS (EI) m/z calcd for C$_{12}$H13FN$_2$O$_2$ (M$^+$) 236.0961, found 236.0952; LRMS (EI) m/z 236 (M$^+$), 180, 163, 136, 08, 57.

(4) (20S)-10-tert-Butyloxycarbonylamino-11-fluoro-7-trimethylsilyl-camptothecin (26) and (20S)-10-tert-butyloxycarbonylamino-9-fluoro-7-trimethylsilylcamptothecin (27) (mixture respectively 1.9:1)

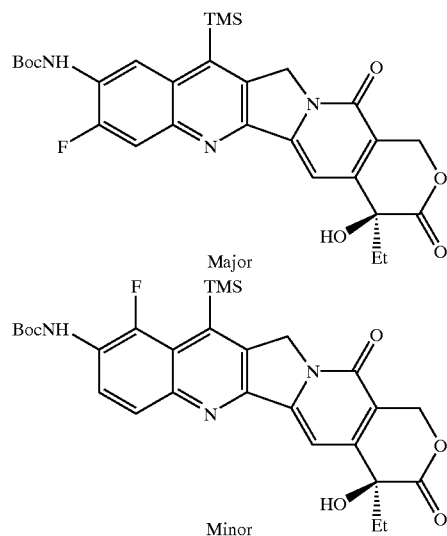

Following the procedure described in Example 1-(2), the compound prepared in Example 1-(1) (66.8 mg, 0.15 mmol) and the compound described in Example (3) (110 mg, 0.50 mmol) provided, after flash-chromatographies (CHCl$_3$/MeOH 96:4; CHCl$_3$/acetone 10:1), 47.6 mg (57%) of a slightly yellow oil containing the above regioisomers: $^1$H NMR (300 MHz, CDCl$_3$) $\delta$0.54 (d, J=4.9 Hz, 9 H$_{minor}$), 0.65 (s, 9 H$_{major}$), 0.99 (t, J=7.3 Hz, 3 H), 1.86 (m, 2 H), 3.93 (br s, 1 H), 5.24 (d, J=16.3 Hz, 1 H$_{minor}$), 5.25 (br s, 2 H$_{major}$), 5.25 (d, J=16.3 Hz, 1 H$_{major}$), 5.30 (br s, 2 H$_{minor}$), 5.68 (d, J=16.3 Hz, 1 H$_{minor}$), 5.69 (d, J=16.3 Hz, 1 H$_{major}$), 6.98 (d, J=3.6 Hz, 1 H$_{minor}$), 7.02 (d, J=3.6 Hz, 1 H$_{major}$), 7.52 (s, 1 H$_{minor}$), 7.53 (s, 1 H$_{major}$), 7.74 (d, J=12.1 Hz, 1 H$_{major}$), 7.92 (br d, J=9.3 Hz, 1 H$_{minor}$), 8.60 (br t, J=8.4 Hz, 1 H$_{minor}$), 9.08 (d, J=8.7 Hz, 1 H$_{major}$); HRMS (EI) m/z calcd for C$_{28}$H$_{32}$FN$_3$O$_6$Si 553.2044, found 553.2022; LRMS (EI) m/z 553 (M$^+$), 493, 479, 453, 435, 424, 409, 394, 380, 353.

(5) (20S)-10-Amino-11-fluoro-7-trimethylsilylcamptothecin (28)

The compound prepared in Example (4) (41.3 mg, 0.0746 mmol) was deprotected following the conditions described in Example 9-(3). After workup, the crude was subjected to a flash-chromatography (CHCl$_3$/acetone/MeOH 70:10:1.5) to provide, in order of elution, first 14.1 mg (42%) of the pure (20S)-10-amino-11-fluoro-7-trimethylsilyl-camptothecin, then a 15.2 mg of a c.a. 1:1 mixture of (20S)-10-amino-11-fluoro-7-trimethylsilylcamptothecin and (20S)-10-amino-9-fluoro-7-trimethylsilylcamptothecin. The characteristics of (20S)-10-amino-11-fluoro-7-trimethylsilylcamptothecin are as follows: [α]$_{20D}$+20.0 (c 0.2, CHCl$_3$/MeOH 4:1); $^1$H NMR (300 MHz, CDCl$_3$) $\delta$0.59 (s, 9 H), 1.00 (t, J=7.4 Hz, 3 H), 1.86 (m, 2 H), 3.86 (br s, 1 H), 4.31 (br s, 2 H), 5.21 (br s, 2 H), 5.26 (d, J=16.4 Hz, 1 H), 5.69 (d, J=16.4 Hz, 1 H), 7.30 (d, J=9.3 Hz, 1 H), 7.50 (s, 1 H), 7.69 (d, J=11.8 Hz, 1 H); $^{13}$C NMR (75 MHz, CDCl$_3$/CD$_3$OD 10:1) $\delta$1.4, 7.7, 31.4, 51.9, 66.1, 72.7, 97.1, 109.4, 113.6 (d, $J_{CF}$=20 Hz), 117.3, 130.8, 134.4, 136.4, 140.2, 142., 146.5, 147.6, 150.6, 153.9, 154.0 (d, $J_{CF}$=251 Hz), 157.6, 173.9; HRMS (EI) m/z calcd for C$_{23}$H$_{24}$FN$_3$O$_4$Si (M$^+$) 453.1520, found 453.1500; LRMS (EI) m/z 453 (M$^+$), 424, 409, 394, 352, 181, 131, 119.

Example 11

Preparation of (20S)-11,12-difluoro-7-trimethylsilylcamptothecin and (20S)-9,10-difluoro-7-trimethylsilylcamptothecin (mixture respectively 3:1)

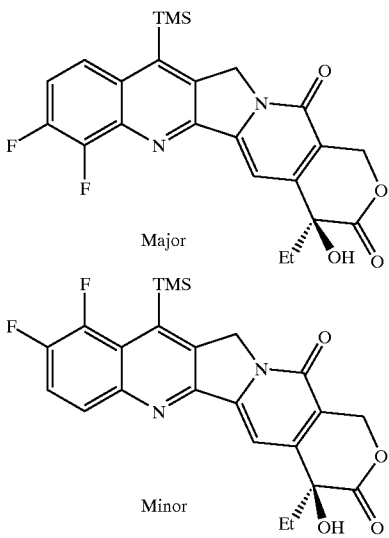

Following the procedure described in Example 1-(2), the compound prepared in Example 1-(1) (44.5 mg, 0.10 mmol) and 2,3-difluorophenyl isonitrile [prepared in 20% yield following the procedure of Weber, W. P. et al., *Tetrahedron Lett.*, 13, 1637 (1972) with stirring 2 days at room temperature before workup] (42 mg, 0.30 mmol) afforded, after flash-chromatographies (CHCl$_3$/MeOH 95:5; CHCl$_3$/acetone 10:1 to 4:1), 22.6 mg (50%) of a slightly yellow oil containing the above regioisomers: $^1$H NMR (300 MHz, CDCl$_3$) $\delta$0.56 (d, J=4.8 Hz, 1 H$_{minor}$), 0.65 (s, 9 H$_{major}$), 1.00 (t, J=7.4 Hz, 3 H), 1.86 (m, 2 H), 3.87 (br s, 1 H$_{minor}$), 3.97 (br s, 1 H$_{major}$), 5.0–5.47 (m, 3 H), 5.68 (d, J=16.5 Hz, 1 H), 5.70 (d, J=16.4 Hz, 1 H$_{minor}$), 7.31 (m, 1 H$_{minor}$), 7.44 (dt, J=9.4, 7.4 Hz, 1 H$_{major}$), 7.59 (s, 1 H$_{minor}$), 7.60 (s, 1 H$_{major}$), 7.68 (m, 1 H$_{minor}$), 7.93 (m, 1 H$_{major}$); HRMS (EI) m/z calcd for C$_{23}$H$_{22}$F$_2$N$_2$O$_4$Si (M$^+$) 456.1317, found 456.1321; LRMS (EI) m/z 456 (M$^+$), 438, 428, 412, 383, 356, 327.

Example 12

Preparation of 20S-7-triisopropylsilylcamptothecin

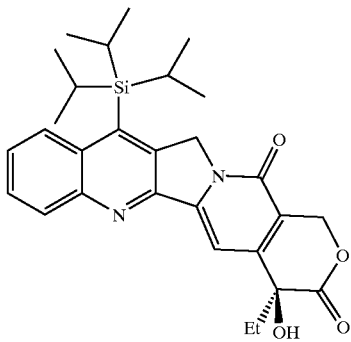

(1) (S)-4-Ethyl-4-hydroxy-6-iodo-3-oxo-7-(triisopropylsilyl-2-propynyl)-1H-pyrano[3,4-c]-8-pyridone Following the procedure outlined in example 1-(1), iodopyridone 2, (200 mg, 0.598 mmol) was combined with triisopropylsilyl-2-propynyl bromide (329 mg, 1.196 mmol). Chromatography (CH$_2$Cl$_2$/AcOEt 9:1) gave 41.1 mg (13%) of a white foam: $^1$H NMR (300 MHz, CDCl$_3$) $\delta$0.91 (t, J=7 Hz, 6 H), 0.99 (s, 18 H), 1.71 (m, J=7 Hz, 2 H), 3.65 (s, 1 H), 5.0–5.2 (m, 3 H), 5.45 (d, J=16 Hz, 1 H), 7.13 (s, 1 H); $^{13}$C NMR (75 MHz, CDCl$_3$) $\delta$7.7, 11.2, 18.7, 31.7, 44.6, 66.5, 71.9, 87.7, 100.1, 116.6, 118.2, 148.6, 158.0, 173.4; HRMS (EI) m/z calcd for C$_{22}$H$_{32}$INO$_4$Si (M$^+$) 529.1162, found 529.1145; LRMS (EI) m/z 529 (M$^+$), 486, 442, 82, 59.

(2) (20S)-7-Triisopropylsilylcamptothecin

Following the procedure outlined in example 1-(2), the pyridone described above (41 mg, 0.077 mmol) yielded 23.3 mg (60%) of a light yellow solid: $[\alpha]_D^{20}$+31.7 (c 0.2, CH$_2$Cl$_2$); IR (CHCl$_3$, cm$^{-1}$) 3026, 3008, 2996, 2962, 2950, 2932, 2892, 2869, 1742, 1658, 1598, 1555, 1466, 1230, 1220, 1158; $^1$H NMR (300 MHz, CDCl$_3$) $\delta$1.02 (t, J=7 Hz, 3 H), 1.18 (d, J=7 Hz, 18 H), 1.60–2.0 (m, 5 H), 2.17 (s, 1 H), 5.31 (d, J=16 Hz, 1 H), 5.41 (s, 2 H), 5.76 (d, J=16, 1 H), 7.61 (t, J=7 Hz, 1 H), 7.69 (s, 1 H), 7.78 (t, J=7 Hz 1 H), 8.20 (t, J=7 Hz, 2 H); $^{13}$C NMR (125 MHz, CDCl$_3$) $\delta$7.9, 13.5, 19.2, 31.7, 52.6, 66.5, 72.9, 98.4, 118.6, 127.1, 129.7, 130.2, 130.4, 133.6, 136.3, 145.0, 146.0, 150.3, 150.6, 157.4, 174.1; HRMS (EI) m/z calcd for C$_{29}$H$_{36}$N$_2$O$_4$Si (M$^+$) 504.2444, found 504.2436; LRMS (EI) m/z 504 (M$^+$), 461, 433, 419, 405, 391, 375, 361, 347, 311, 275, 174, 93, 69, 59.

Example 13

Preparation of 20S-7-triisopropylsilylcamptothecin

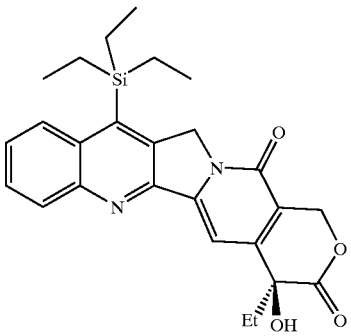

(1) (S)-4-Ethyl-4-hydroxy-6-iodo-3-oxo-7-(triethylsilyl-2-propynyl)-1H-pyrano[3,4-c]-8-pyridone Following the procedure outlined in example 1-(1), iodopyridone 2, (150 mg, 0.450 mmol) was combined with triethylsilyl-2-propynyl bromide (210 mg, 0.90 mmol). Chromatography (CH$_2$Cl$_2$/AcOEt 9:1) gave 97.0 mg (45%) of a white foam: $^1$H NMR (300 MHz, CDCl$_3$) $\delta$0.54 (q, J=8 Hz, 6 H), 0.92 (t, J=8 Hz, 12 H), 1.74 (m, J=7 Hz, 2 H), 3.57 (s, 1 H), 4.9–5.1 (m, 3 H), 5.46 (d, J=16 Hz, 1 H), 7.13 (s, 1 H); $^{13}$C NMR (75 MHz, CDCl$_3$) $\delta$4.1, 7.4, 7.6, 31.5, 44.5, 66.3, 71.8, 88.7, 99.2, 100.0, 116.5, 118.1, 148.5, 158.0, 173.2; HRMS (EI) m/z calcd for C$_{19}$H$_{26}$INO$_4$Si (M$^+$) 487.0676, found 487.0688; LRMS (EI) m/z 487 (M$^+$), 458, 430, 420, 402, 360, 332, 153, 141, 125, 96, 83, 68, 57.

(2) (20S)-7-Triethylsilylcamptothecin

Following the procedure outlined in example 1-(2), the pyridone described above (48.7 mg, 0.1 mmol) yielded 29.8 mg (65%) of a light yellow solid: $[\alpha]_D^{20}$+35.9 (c 0.2, CH$_2$C$_{12}$); IR (CHCl$_3$, cm$^{-1}$) 3015, 3002, 2960, 2935, 1741, 1658, 1599, 1219, 1199, 1158; $^1$H NMR (300 MHz, CDCl$_3$) $\delta$0.80–1.00 (m, 12 H), 1.0–1.18 (m, 6 H), 1.70–1.90 (m, 2

H), 5.22–5.27 (m, 3 H), 5.69 (d, J=16 Hz, 1 H), 7.58 (t, J=7 Hz, 1 H), 7.63 (s, 1 H), 7.72 (t, J=7 Hz 1 H), 8.18 (m, 2 H); $^{13}$C NMR (125 MHz, CDCl$_3$) δ5.0, 7.6, 7.9, 31.7, 52.1, 66.5, 72.9, 97.7, 118.3, 127.4, 127.9, 129.7, 131.2, 132.6, 136.1, 142.6, 146.6, 147.9, 150.2, 150.9, 157.6, 174.1; HRMS (EI) m/z calcd for C$_{26}$H$_{30}$N$_2$O$_4$Si (M$^+$) 462.1975, found 462.1982; LRMS (EI) m/z 462 (M$^+$), 433, 418, 405, 389, 361, 256, 220, 205, 189, 178, 149, 137, 123, 109, 95, 81, 69, 57.

Example 14

Preparation of (20S)-7-(dimethyl-(1'S,2'S,5'S) 7,7 dimethylnorpinylsilyl)camptothecin

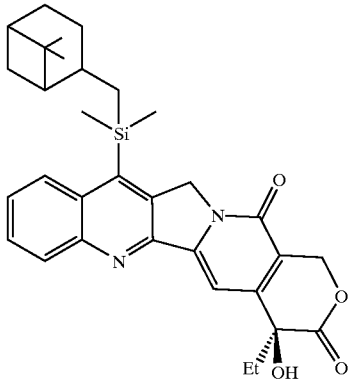

(1) (S)-4-Ethyl-4-hydroxy-6-iodo-3-oxo-7-(dimethyl-(1S, 2S,5S) 7,7 dimethylnorpinylsilyl-2-propynyl)-1H-pyrano[3, 4-c]-8-pyridone Following the procedure outlined in example 1-(1), iodopyridone 2 (150 mg, 0.450 mmol) was combined with dimethyl-(1S, 2S, 5S) 7,7 dimethylnorpinylsilyl-2-propynyl bromide (281 mg, 0.90 mmol). Chromatography (CH$_2$Cl$_2$/AcOEt 9:1) gave 100.8 mg (39%) of a white foam: $^1$H NMR (300 MHz, CDCl$_3$) δ0.10 (d, J=2 Hz, 6 H), 0.48–0.70 (m, 2 H), 0.72 (s, 3 H), 0.93 (t, J=7 Hz, 3 H), 1.10 (s, 3 H), 1.15–1.40 (m, 3 H), 1.60–1.85 (m, 6 H), 1.88–2.00 (m, 1 H), 2.05–2.20 (m, 1 H), 3.58 (s, 1 H), 4.95 (m, 3 H), 5.46 (d, J=16 Hz, 1 H), 7.13 (s, 1 H); $^{13}$C NMR (75 MHz, CDCl$_3$) δ0.78, 7.8, 20.2, 23.1, 24.0, 24.8, 25.3, 27.0, 31.3, 31.7, 39.7, 40.7, 44.7, 49.1, 66.5, 71.9, 91.0, 98.5, 100.3, 116.6, 118.3, 148.7, 158.0, 173.4.

(2) (20S)-7-(dimethyl-(1'S,2'S,5'S) 7,7 dimethylnorpinylsilyl)camptothecin

Following the procedure outlined in example 1-(2), the pyridone described above (57.0 mg, 0.1 mmol) yielded 29.4 mg (54%) of a light yellow solid: [α]$_D^{20}$+29.2 (c 0.2, CH$_2$Cl$_2$); IR (CHCl$_3$, cm$^{-1}$) 3020, 3000, 2980, 2972, 2939, 2914, 2824, 2867, 1741, 1658, 1599, 1556, 1264, 1231, 1201, 1157, 843; $^1$H NMR (300 MHz, CDCl$_3$) δ0.50–0.70 (m, 8 H), 0.90–1.10 (m, 9 H), 1.10–1.35 (m, 4 H), 1.40–1.60 (m, 3 H), 1.72 (m, 1 H), 1.80–1.95 (m, 2 H), 2.05–2.11 (m, 2 H), 5.25 (d, J=16 Hz 1 H), 5.27 (s, 2 H), 5.69 (d, J=16 Hz, 1 H), 7.58 (t, J=8 Hz, 1 H), 7.62 (s, 1 H), 7.72 (t, J=8 Hz, 1 H), 8.10–8.2 (m, 2 H); $^{13}$C NMR (125 MHz, CDCl$_3$) δ1.4, 7.9, 19.9, 23.0, 24.6, 25.3, 26.8, 31.6, 31.7, 39.6, 40.5, 49.3, 52.0, 66.5, 72.9, 97.7, 118.3, 127.4, 128.3, 129.7, 131.2, 132.1, 134.6, 144.6, 146.6, 148.0, 150.2, 150.9, 157.6, 174.0; HRMS (EI) m/z calcd for C$_{32}$H$_{38}$N$_2$O$_4$Si (M$^+$) 542.2601, found 542.2588; LRMS (EI) m/z 542 (M$^+$), 498, 487, 460, 443, 431, 406, 387, 377, 362, 333, 318, 304, 289, 275, 219, 178, 166, 141, 115, 95, 67.

Example 15

(20S)-7-(3-cyanopropyldimethylsilyl)camptothecin

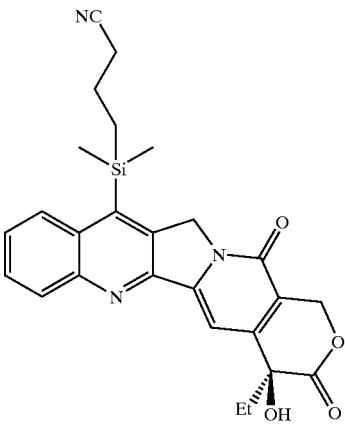

(1) (S)-4-Ethyl-4-hydroxy-6-iodo-3-oxo-7-(3-cyanopropyldimethylsilyl-2-propynyl)-1H-pyrano[3,4-c]-8-pyridone Following the procedure cited by Rico and co-workers (J. Org. Chem. 1994, 59, 415), iodopyridone 2, (150 mg, 0.450 mol) was combined with 3-cyanopropyldimethylsilyl-2-propynyl bromide (165 mg, 0.678 mmol), k$_2$CO$_3$ (124 mg, 0.90 mmol), Bu$_4$N$^+$Br$^-$ (14.5 mg, 0.045 mmol), H$_2$O (0.02 mL) and toluene (3.6 mL). This mixture was refluxed for 1 h. After filtration and chromatography (CH$_2$Cl$_2$/AcOEt 9:1) 34.0 mg (15%) of a white oil was obtained: $^1$H NMR (300 MHz, CDCl$_3$) δ0.17 (s, 6 H), 0.70–0.80 (m, 2 H), 0.98 (t, J=7 Hz, 3 H), 1.70–1.90 (m, 4 H), 2.39 (t, J=7, 2 H), 3.66 (s, 1 H), 4.9–5.22 (m, 3 H), 5.51 (d, J=16 Hz, 1 H), 7.19 (s, 1 H); $^{13}$C NMR (125 MHz, CDCl$_3$) δ–2.1, 7.8, 15.4, 20.5, 20.6, 31.6, 44.6, 66.4, 71.9, 89.1, 99.6, 100.0, 116.7, 118.3, 119.7, 148.8, 158.0, 173.3; HRMS (EI) m/z calcd for C$_{19}$H$_{23}$IN$_2$O$_4$Si (M$^+$) 498.0472, found 498.0480; LRMS (EI) m/z 498 (M$^+$), 483, 470, 445, 430, 416, 402, 392, 371, 348, 335, 306, 290, 266, 223, 202, 185, 163, 136, 126, 109, 98, 81, 69, 57.

(2) (20S)-7-(3-cyanopropyldimethylsilyl)camptothecin

Following the procedure outlined in example 1-(2), the pyridone described above (25.0 mg, 0.05 mmol) yielded 9.8 mg (41%) of a light yellow solid: [α]$_D^{20}$+34.3 (c 0.2, CH$_2$Cl$_2$); IR (CHCl$_3$, cm$^{-1}$) 3025, 3016, 1741, 1659, 1600, 1264, 1222; $^1$H NMR (300 MHz, CDCl$_3$) δ0.71 (s, 6 H), 1.05 (t, J=7 Hz,3 H), 1.26 (m, 2 H),1.66 (m, 2H), 1.90 (m, 2 H), 2.35 (t, J=7 Hz, 2 H), 3.76 (s, 1 H), 5.31 (d, J=16 Hz, 1 H), 5.31 (s, 2 H), 5.75 (d, J=16 Hz, 1 H), 7.67 (m, 2 H), 7.82 (t, J=8 Hz, 1 H), 8.17 (d, J=8 Hz 1 H), 8.24 (d, J=8 Hz, 1 H) $^{13}$C NMR (125 MHz, CDCl$_3$) δ0.2, 7.9, 16.8, 20.7, 20.73, 31.7, 50.9, 66.5, 72.8, 97.9, 118.5, 119.2, 127.7, 127.8, 130.0, 131.4, 131.9, 135.2, 141.9, 146.3, 148.1, 150.3, 151.1, 157.5, 174.0; HRMS (EI) m/z calcd for C$_{26}$H$_{27}$N$_3$O$_4$Si (M$^+$) 473.1771, found 473.1755; LRMS (EI) m/z 473 (M$^+$), 444, 429, 414, 400, 389, 373 362, 344, 331, 303, 289, 2.75, 245, 219, 166, 152, 130, 98, 71.

Example 16

Preparation of (20S)-7-(3-halopropyldimethylsilyl) camptothecin (the chloropropyl derivative is DB-148)

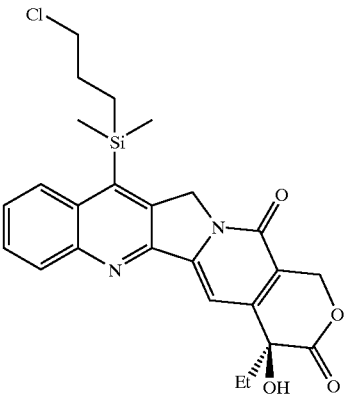

(1) (S)-4-Ethyl-4-hydroxy-6-iodo(and 6-bromo)-3-oxo-7-(3-chloropropyldimethylsilyl-2-propynyl)-1H-pyrano[3,4-c]-8-pyridone Following the procedure outlined in example 1-(1), [iodopyridone 2 (150 mg, 0.450 mmol) was combined with 3-chloropropyldimethylsilyl-2-propynyl bromide (228 mg, 0.90 mmol). Chromatography ($CH_2Cl_2$/AcOEt 9:1) gave 75.4 mg (33%) of a clear oil. Analysis of the NMR showed the presence of the alkyl bromide in addition to the desired chloro derivative in a 1.6:1 ratio in favor of the former.: $^1$H NMR (300 MHz, $CDCl_3$) $\delta$ 0.09 (s, 6 H), 0.60–0.70 (m, 2 H), 0.85–0.89 (t, J=7 Hz, 3 H), 1.60–1.95 (m, 4 H), 3.33 (t, J=7 Hz, 2 H, assigned to iodo), 3.44 (t, J=7 Hz, 2 H, assigned to bromo), 3.75 (s, 1 H), 4.91–5.18 (m, 3 H), 5.42 (d, J=16 Hz, 1 H), 7.12 (s, 1 H).

(2) (20S)-7-(3-halopropyldimethylsilyl)camptothecin

Following the procedure outlined in example 1-(2), the pyridone described above (51 mg, 0.1 mmol) yielded 23 mg (49%) of a light yellow solid. Analysis of the spectral data identified this solid as a 3 component mixture corresponding to the chloro, bromo and the iodo derivatives in a 1.6:1:1.3 ratio: $[\alpha]_D^{20}$+30.8 (c 0.2, $CH_2Cl_2$); IR ($CHCl_3$, cm$^{-1}$) 3029, 3012, 2980, 2963, 2933, 1742, 1658, 1600, 1556, 1258, 1233, 1218, 1200, 1158, 1045, 843, 822, 794; $^1$H NMR (300 MHz, $CDCl_3$) $\delta$ 0.69 (s, 6 H), 1.04 (t, J=7 Hz, 3 H), 1.18–1.30 (m, 2 H), 1.60–2.0 (m, 4 H), 3.15 (t, J=7 Hz, 2 H. assigned to iodo), 3.36 (t, J=7 Hz, 2 H, assigned to bromo), 3.48 (t, J=7 Hz, 2 H, assigned to chloro), 3.88 (s, 1 H), 5.30 (d, J=16 Hz, 1 H), 5.31 (s, 2 H), 5.74 (d, J=16 Hz, 1 H), 7.62–7.66 (m, 2 H), 7.87 (t, J=8 Hz, 1 H), 8.18 (d, J=8 Hz, 1 H), 8.22 (d, J=8 Hz, 1 H); $^{13}$C NMR (125 MHz, $CDCl_3$) $\delta$ 0.2, 7.9, 14.7, 27.5, 31.7, 47.4, 51.9, 66.4, 72.8, 98.2, 118.6, 127.7, 127.9, 130.0, 131.0, 132.0, 135.2, 146.1, 147.6, 150.2, 157.5, 174.0; HRMS (EI) m/z calcd for $C_{25}H_{27}ClN_2O_4Si$ (M$^+$) 482.1429, found 482.1413; LRMS (EI) m/z 482 (M$^+$), 453, 438, 361, 305, 275.

Example 17

Preparation of (20S)10-acetoxy-7-tert-butyldimethylsilylcamptothecin

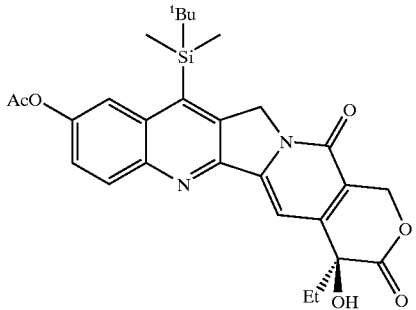

Following the procedure outlined in example 1-(2), the pyridone described above (34.5 mg, 0.071 mmol) and p-acetoxyisonitrile yielded 21.3 mg (58%) of a light yellow solid: $[\alpha]_D^{20}$+36.2 (c 0.2, $CH_2Cl_2$); IR ($CHCl_3$, cm$^{-1}$) 3029, 3000, 2958, 2931, 2902, 2885, 2859, 1742, 1659, 1600, 1557, 1504, 1464, 1371, 1256, 1232, 1195, 1166, 1045; $^1$H NMR (300 MHz, $CDCl_3$) $\delta$ 0.69 (s, 6 H), 0.90 (s, 9 H), 1.04 (t, J=7 Hz, 3 H), 1.80–2.00 (m, J=7 Hz, 2 H), 2.40 (s, 3 H), 3.81 (s, 1 H), 5.30 (d, J=16 Hz 1 H), 5.31. (s, 2 H), 5.75 (d, J=16 Hz, 1 H), 7.53 (dd, $J_1$=9 Hz, $J_2$=2 Hz, 1 H), 7.65 (s, 1 H), 8.08 (d, J=2 Hz, 1 H), 8.21 (d, J=9 Hz, 1 H); $^{13}$C NMR (125 MHz, $CDCl_3$) $\delta$ 0.6, 7.9, 19.3, 21.5, 27.2, 31.7, 52.5, 66.5, 72.9, 97.7, 118.4, 120.4, 124.8, 132.1, 133.2, 136.7, 142.8, 146.2, 146.4, 149.0, 150.2, 150.8, 157.5, 169.1, 174.1; LRMS (EI) m/z 520 (M$^+$), 478, 463, 421, 377, 347, 320, 291, 57.

Example 18

(2) (20S)10-Acetoxy-7-tert-butyldimethylsilylcamptothecin

Following the procedure outlined in example 2-(2), the pyridone described above (34.5 mg, 0.071 mmol) yielded, using the same chromatographic conditions, 21.3 mg (58%) of a light yellow solid: $[\alpha]_D^{20}$+36.2 (c 0.2, $CH_2Cl_2$) ; IR ($CHCl_3$, cm$^{-1}$) 3029, 3000, 2958, 2931, 2902, 2885, 2859, 1742, 1659, 1600, 1557, 1504, 1464, 1371, 1256, 1232, 1195, 1166, 1045; $^1$H NMR (300 MHz, $CDCl_3$)$^{67}$ 0.69 (s, 6 H), 0.90 (s, 9 H), 1.04 (t, J=7 Hz, 3 H), 1.80–2.00 (m, J=7 Hz, 2 H), 2.40 (s, 3 H), 3.81 (s, 1 H), 5.30 (d, J=16 Hz 1 H), 5.31. (s, 2 H), 5.75 (d, J=16 Hz, 1 H), 7.53 (dd, $J_1$=9 Hz, $J_2$=2 Hz, 1 H), 7.65 (s, 1 H), 8.08 (d, J=2 Hz, 1 H), 8.21 (d, J=9 Hz, 1 H); $^{13}$C NMR (125 MHz, $CDCl_3$) $\delta$ 0.6, 7.9, 19.3, 21.5, 27.2, 31.7, 52.5, 66.5, 72.9, 97.7, 118.4, 120.4, 124.8, 132.1, 133.2, 136.7, 142.8, 146.2, 146.4, 149.0, 150.2, 150.8, 157.5, 169.1, 174.1; HRMS (EI) m/z calcd for $C_{28}H_{32}N_2O6Si$ (M$^+$) 520.2030, found 520.2014 LRMS (EI) m/z 520 (M$^+$), 478, 463, 421, 377, 347, 320, 291, 57.

Example 19

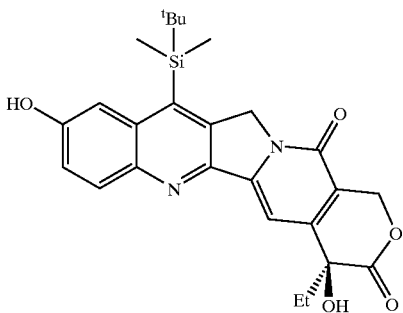

(20S)10-Hydroxy-7-tert-butyldimethylsilylcamptothecin (DB-67)

Following the procedure outlined in example 5, (13.4 mg, 0.026 mmol) of the compound described in example 18 was converted to the hydroxy derivative. Purification (2:1 CH$_2$Cl$_2$.Acetone) on a preparative TLC plate gave 10.6 mg (85%) of a yellow solid: [α]$_D^{20}$+17.4 (c 0.2, 3:1 CH$_2$Cl$_2$/MeOH); $^1$H NMR (300 MHz, 3:1 CDCl$_3$/CD$_3$OD) δ0.66 (s, 6 H), 0.88–1.05 (m, 12 H), 1.80–2.00 (m, 2 H), 5.25–5.30 (m, 3 H), 5.70 (d, J=16 Hz, 1 H), 7.37 (dd, J$_1$=9 Hz, J$_2$=2 Hz, 1 H), 7.54 (d, J=2 Hz, 1 H), 7.60 (s, 1 H), 8.05 (d, J=9 Hz, 1 H); $^{13}$C NMR (125 MHz, (3:1) CDCl$_3$:CD$_3$OD) δ8.1, 20.6, 27.6, 30.4, 31.9, 53.6, 66.5, 73.9, 98.6, 112.1, 118.8, 123.3, 132.1, 135.6, 137.4, 141.6, 143.8, 147.3, 148.4, 152.6, 157.5, 158.7, 174.7; HRMS (EI) m/z calcd for C$_{26}$H$_{30}$N$_2$O$_5$Si (M$^+$) 478.1924, found 478.1947 LRMS (EI) m/z 478 (M$^+$), 434, 421, 377, 304, 284, 227, 178, 149, 137, 109, 97, 83, 69, 57.

Example 20

Preparation of (20S)-7-(trimethylsilylmethyl)camptothecin

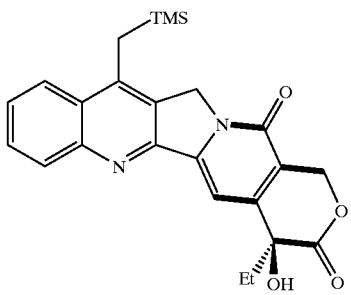

(1) (S)-4-Ethyl-4-hydroxy-6-iodo-3-oxo-7-(4-trimethylsilyl-2-butynyl)-1H-pyrano[3,4-c]-8-pyridone Following the procedure described in Example 1-(1), iodopyridone (2) (200 mg, 0.60 mmol) and 4-trimethylsilyl-2-butynyl bromide (245 mg, 1.20 mmol) gave, after flash-chromatography (CH$_2$Cl$_2$/AcOEt 9:1), 77.7 mg (28%) of a white foam: [α]$_D^{20}$+62.7 (c 0.2, CHCl$_3$); IR (CHCl$_3$, cm$^{-1}$) 3540, 3026, 2955, 1742, 1649, 1607, 1529, 1250, 1219, 1208, 1158, 1140; $^1$H NMR (300 MHz, CDCl$_3$) δ0.06 (s, 9 H), 0.92 (t, J=7.4 Hz, 3 H), 1.44 (t, J=2.4 Hz, 2 H), 1.76 (m, J=7.4 Hz, 2 H), 3.74 (s, 1 H), 4.98 (br s, 2 H), 5.07 (d, J=15 Hz, 1 H), 5.48 (d, J=16.4 Hz, 1 H), 7.15 (s, 1 H); $^{13}$C NMR (75 MHz, CDCl$_3$) δ-1.96, 7.5, 7.6, 31.5, 44.8, 66.3, 71.7, 84.3, 100.3, 116.3, 118.1, 148.3, 157.9, 173.3; HRMS (EI) m/z calcd for C$_{17}$H$_{22}$INO$_4$Si (M$^+$) 459.0352, found 459.0363; LRMS (EI) m/z 459 (M$^+$), 444, 386, 348, 73, 57.

(2) (20S)-7-(Trimethylsilylmethyl)camptothecin

Following the procedure described in Example 1-(2), the compound prepared in (1) (46 mg, 0.10 mmol) yielded, after flash chromatographies (CH$_2$Cl$_2$/MeOH 96:4; CH$_2$Cl$_2$/acetone 9:1), 16.2 mg (38%) of a light yellow solid: [α]$_D^{20}$+37.6 (c 0.2, CHCl$_3$); IR (CHCl$_3$, cm$^{-1}$) 3002, 2984, 2962, 1741, 1659, 1601, 1572, 1559, 1253, 1219, 1197, 1157, 849; $^1$H NMR (500 MHz, CDCl$_3$) δ-0.34 (s, 9 H), 0.62 (t, J=7.3 Hz, 3 H), 1.48 (m, 2 H), 2.31 (d, J=3.0 Hz, 2 H), 3.53 (s, 1 H), 4.74 (s, 2 H), 4.89 (d, J=16.2 Hz, 1 H), 5.34 (d, J=16.2 Hz, 1 H), 6.85 (s, 1 H), 7.20 (t, J=7.8 Hz, 1 H), 7.36 (t, J=7.4 Hz, 1 H), 7.57 (d, J=8.4 Hz, 1 H), 7.78 (d, J=8.4 Hz, 1 H); $^{13}$C NMR (75 MHz, CDCl$_3$) δ-0.32, 1.1, 7.9, 31.6, 50.3, 66.4, 72.9, 98.1, 112.3, 124.4, 125.84, 126.91, 127.2, 130.1, 130.5, 144.6, 147.4, 149.2, 150.3, 151.5, 157.7, 174.1; HRMS (EI) m/z calcd for C$_{24}$H$_{26}$N$_2$O$_4$Si (M$^+$) 434.1676, found 434.1662; LRMS (EI) m/z 434 (M$^+$), 390, 362, 316, 290, 242, 223, 185, 147, 93, 73.

Example 21

(20S)-10-Hydroxy-7-[(2-trimethylsilyl)ethyl]camptothecin (36a) (DB-174)

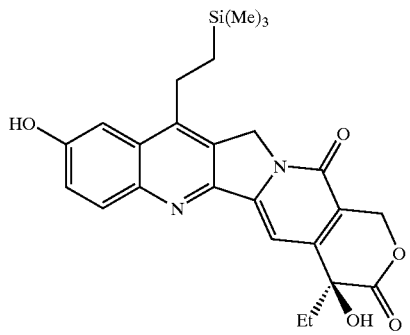

(1) (4,4-Dibromo-but-3-enyl)trimethylsilane

This known compound was prepared by a modification of the procedure in Piers, E.; Gavai, A. V. *J. Org. Chem.* 1990, 55, 2374. To a flame dried flask was added dry CH$_2$Cl$_2$ (150 mL) and triphenylphosphine (16 g, 61.2 mmol) The temperature was lowered to 0° C. and CBr$_4$ (10.15 g, 30.6 mmol) was added portionwise. After 30 min, a solution of 3-trimethylsilylpropanal (2.0 g, 15.3 mmol) in dry CH$_2$Cl$_2$ (20 ml) was added. After 1 h at 0° C., the reaction was diluted with ether and filtered through celite. The celite was rinsed with ether (4×50 mL) and the combined ether solution was extracted with H$_2$O (100 mL), saturated NaHCO$_3$ (100 mL), saturated NH$_4$Cl (100 mL) and brine (100 mL). The organic layer was dried (MgSO$_4$), filtered and evaporated to give a crude white solid. The solid residue was washed with pentane. The pentane solution was concentrated and the oily residue was chromatographed on silica gel (pentane 100%) to give (4,4-dibromo-but-3-enyl)trimethylsilane as a clear oil weighing 3.7 g. $^1$H NMR showed 27% contamination by remaining pentane which gives a corrected yield of 62%: IR (neat, cm$^{-1}$) 2953, 2922, 2898, 1620, 1443, 1413, 1249, 1176, 1034, 986, 859, 837; $^1$H NMR (300 MHz, CDCl$_3$) δ0.03 (s, 9 H), 0.62–0.67 (m, 2 H), 2.06–2.14 (m, 2 H), 6.41 (t, J=7 Hz 1 H); $^{13}$C NMR (75 MHz, CDCl$_3$) δ-1.9, 15.1, 27.7, 87.5, 141.2.

(2) 5-Trimethylsilanylpent-2-yn-1-ol (40)

To a flame dried flask was added (4,4-dibromo-but-3-enyl)trimethylsilane (3.43 g, 12 mmol). Dry THF (150 mL) was added and the mixture was cooled to −78° C. BuLi 1.6N in hexanes (24 mmol, 15 mL) was added and the mixture was stirred 1 h at −78° C., warmed to 22° C., and stirred for an additional 1 h. Finally, paraformaldehyde (1.4 g) was added and the mixture was refluxed. After 3.5 h the reaction was cooled to 22° C. and sat. NH$_4$Cl (50 mL) was added. The contents of the flask were transferred to a separatory funnel and extracted with ether (3×200 mL). The organic layer was dried (Na$_2$SO$_4$), filtered and evaporated to give a crude yellow oil. Flash chromatography on silica gel (pentane/ether 5:1) afforded 1.57 g (84%) of 5-trimethylsilanylpent-2-yn-1-ol: IR (neat, cm$^{-1}$) 3350, 2953, 2219, 1436, 1412, 1318, 1249, 1178, 1124, 1015, 905, 853; $^1$H NMR (300 MHz, CDCl$_3$) δ−0.003 (s, 9 H), 0.76 (t, J=8 Hz 2 H), 1.75 (s, 1 H), 2.20–2.24 (m, 2 H), 4.21 (br s, 2 H); $^{13}$C NMR (75 MHz, CDCl$_3$) δ−1.3, 13.8, 16.4, 51.7, 78.2, 88.9; HRMS (EI) ml/z calcd for C$_7$H$_{13}$OSi (M-CH$_3$) 141.0736, found 141.0733 LRMS (EI) m/z 141 (M-CH$_3$), 123, 113, 103, 97, 91, 85, 75, 66, 59.

(3) (5-Bromopent-3-ynyl)trimethylsilane (41)

To a flame dried flask was added PPh$_3$ (1.76 g, 6.73 mmol) followed by dry CH$_2$Cl$_2$ (60 mL). The mixture was placed in an ice bath and bromine (0.34 mL, 6.41 mmol) was added dropwise. A small amount of PPh$_3$ was added until the reaction went from yellow to clear in color. After 0.5 h at 0° C., 5-trimethylsilanylpent-2-yn-1-ol (1.0 g, 6.41 mmol) was dissolved in CH$_2$Cl$_2$ (5 mL) and added dropwise. After 4 h at 0$_i$ C, the reaction mixture was poured into a separatory funnel, diluted with pentane (250 mL) and extracted with H$_2$O (100 mL) and sat. NaHCO$_3$ (100 mL). The organic layer was dried (MgSO$_4$), filtered and reduced in volume to 50 mL. The crude solution was chromatographed on a pad of silica gel with pentane (500 mL). After evaporation of the pentane, (5-bromopent-3-ynyl)trimethylsilane (1.2 g 87%) was obtained as a clear oil: IR (neat, cm$^{-1}$) 2953, 2922, 2899, 2230, 1431, 1317, 1248, 1208, 852; $^1$H NMR (300 MHz, CDCl$_3$) δ0.03 (s, 9 H), 0.79 (t, J=8 Hz, 2 H), 2.28 (tt, J$_1$=8 Hz, J$_2$=2 Hz, 2 H), 3.92 (t, J=2 Hz, 2 H); $^{13}$C NMR (75 MHz, CDCl$_3$) δ1.7, 13.6, 15.7, 15.8, 74.6, 90.2; HRMS (EI) m/z calcd for C$_7$H$_{12}$BrSi (M-CH$_3$) 202.9892, found 202.9889 LRMS (EI) m/z 203 (M-CH$_3$), 137, 73, 66.

(4) (20S)-4-Ethyl-4-hydroxy-6-iodo-3-oxo-7-(5-trimethylsilanylpent-2-ynyl)-1H-pyrano[3,4-c]-8-pyridone (43)

Following the procedure described in Example 1-(1), iodopyridone (2), (0.2 g, 0.6 mmol)] and (5-bromopent-3-ynyl)trimethylsilane (260 mg, 1.19 mmol) provided after flash chromatography (CH$_2$Cl$_2$/EtOAc 95:5) 0.21 g (74%) of (20S)-4-ethyl-4-hydroxy-6-iodo-3-oxo-7-(5-trimethylsilanyl-pent-2-ynyl)-1H-pyrano[3,4-c]-8-pyridone as a white foam: $[\alpha]_D^{20}$+54.4 (c 0.2, CH$_2$Cl$_2$); IR (CHCl$_3$, cm$^{-1}$) 2952, 1746, 1648, 1528, 1427, 1138, 856, 755; $^1$H NMR (300 MHz, CDCl$_3$) δ−0.03 (s, 9 H), 0.76 (t, J=8 Hz, 2 H), 0.96 (t, J=7 Hz, 3 H), 1.70–2.00 (m, J=7 Hz, 2 H), 2.16 (t, J=8 Hz, 2 H), 3.77 (s, 1 H), 5.04 (s, 2 H), 5.10.(d, J=16 Hz, 1 H), 5.49 (d, J=16 Hz, 1 H), 7.16 (s, 1 H); $^{13}$C NMR (75 MHz, CDCl$_3$) δ−1.6, 7.8, 13.6, 15.7, 31.7, 44.8, 66.5, 71.9, 72.4, 88.1, 100.5, 116.6, 118.3, 148.6, 158.2, 173.5; HRMS (EI) m/z calcd for C$_{18}$H$_{24}$INO$_4$Si (M$^+$) 473.0519, found 473.0507 LRMS (EI) m/z 473 (M$^+$), 458, 386, 360, 346, 139, 73, 57.

(5) (20S)-10-Acetoxy-7-((2-trimethylsilyl)ethyl] camptothecin (45)

Following the procedure described in Example 1-(2), a mixture of the iodopyridone prepared in (4) above (56.8 mg, 0.12 mmol) and p-acetoxyphenyl isonitrile (48 mg, 0.3 mmol) provided after flash chromatography (CH$_2$Cl$_2$/Acetone 10:1) 33.2 mg (55%) of (20S)-10-acetoxy-7-[(2-trimethylsilyl)ethyl]camptothecin as a tan solid: $[\alpha]_D^{20}$+ 21.0 (c 0.2, CH$_2$Cl$_2$); IR (CHCl$_3$, cm$^{-1}$) 3039, 2996, 2954, 1744, 1660, 1602, 1509, 1371, 1229, 1177; $^1$H NMR (300 MHz, CDCl$_3$) δ0.17 (s, 9 H), 0.88–0.95 (m, 2 H), 1.03 (t, J=7 Hz, 3 H), 1.80–2.00 (m, J=7 Hz, 2 H), 2.42 (s, 3 H), 3.00 (m, 2 H), 4.01 (br s, 1 H), 5.22. (s, 2 H), 5.30 (d, J=16 Hz, 1 H), 5.74 (d, J=16 Hz, 1 H), 7.54 (dd, J$_1$=9 Hz, J$_2$=2 Hz 1 H), 7.66 (s, 1 H), 7.72 (d, J=2 Hz, 1 H), 8.22 (d, J=2 Hz, 1 H); $^{13}$C NMR (125 MHz, CDCl$_3$) δ−1.8, 7.9, 17.7, 21.4, 24.3, 31.7, 49.3, 66.4, 72.9, 98.1, 114.5, 118.6, 125.4, 126.6, 127.2, 132.2, 146.8, 147.0, 147.5, 149.6, 150.3, 151.9, 157.7, 169.4, 174.0; HRMS (EI) m/z calcd for C$_{27}$H$_{30}$N$_2$O$_6$Si (M$^+$) 506.1873, found 506.1869 LRMS (EI) m/z 506 (M$^+$), 464, 436, 420, 347, 336, 277, 193, 151, 109, 73.

(6) (20S)-10-Hydroxy-7-[(2-trimethylsilyl)ethyl] camptothecin (36a)

A mixture of the compound prepared in (5) above (17.7 mg, 0.035 mmol) and k$_2$CO$_3$ (9.7 mg, 0.07 mmol) in MeOH (0.2 mL) and H$_2$O (0.2 mL) was stirred for 1.5 h at room temperature. The mixture was acidified with AcOH (8 drops), diluted with brine (10 mL) and extracted with EtOAc (10×20 mL). The combined organic layers were dried (Na$_2$SO$_4$) and evaporated. The crude residue was subjected to two chromatographies (CH$_2$Cl$_2$/MeOH/AcOH 96:3:1 followed by CH$_2$Cl$_2$/Acetone 5:1), which gave 7.6 mg (47%) of (20S)-10-hydroxy-7-[(2-trimethylsilyl)ethyl] camptothecin as a yellow solid: $[\alpha]_D^{20}$+31.3 (c 0.2, CH$_2$Cl$_2$/MeOH 3:1); $^1$H NMR (300 MHz, CDCl$_3$) δ0.15 (s, 9 H), 0.84–0.95 (m, 2 H), 0.99 (t, J=7 Hz, 3 H), 1.80–2.00 (m, J=7 Hz, 2 H), 2.99–3.05 (m, 2 H), 5.20 (s, 2 H), 5.29 (d, J=16 Hz 1 H), 5.62. (d, J=16 Hz 1 H), 7.33 (d, J=2 Hz, 1 H), 7.40 (dd, J$_1$=9 Hz, J$_2$=2 Hz, 1 H), 7.63 (s, 1 H), 8.01 (d, J=9 Hz, 1 H); $^{13}$C NMR (125 MHz, CDCl$_3$) δ−1.8, 8.3, 17.9, 25.1, 32.2, 66.9, 74.4, 99.1, 106.0, 116.1, 119.7, 124.0, 128.4, 129.8, 132.3, 145.5, 146.8, 148.3, 150.1, 153.0, 158.6, 159.4, 175.1; HRMS (EI) m/z calcd for C$_{25}$H$_{28}$N$_2$O$_5$Si (M$^+$) 464.1767, found 464.1788 LRMS (EI) m/z 464 (M$^+$), 420, 405, 391, 364, 347, 167, 149, 104, 91, 73.

This compound showed activity inhibiting cell proliferation in several lines of glioma cells (U87, A172, SG388, T98G, LN-Z308) with median effective concentrations of 10–100 ng/ml.

Example 22

(20S)-10-Amino-7-[2-trimethylsilyl)ethyl] camptothecin (36b) (DB-173)

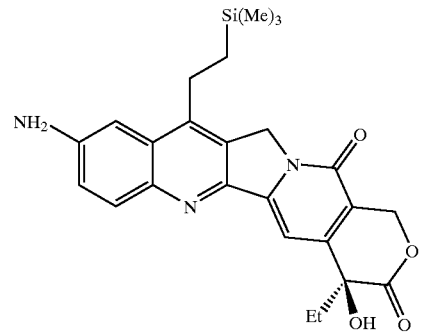

(1) (20S)-10-tert-Butyloxycarbonylamino-7-[(2-trimethylsilyl)ethyl]camptothecin (45b)

Following the procedure described in Example 1-(2), a solution of the iodopyridone prepared in Example 21-(4) above (56.8 mg, 0.12 mmol) was reacted with 4-tert-butyloxycarbonylaminophenyl isonitrile (65.4 mg, 0.3 mmol). Column chromatography (CH$_2$Cl$_2$/Acetone 10:1)

gave 38 mg (56%) (20S)-10-tert-butyloxycarbonylamino-7-[(2-trimethylsilyl)ethyl] camptothecin as a tan solid: $[\alpha]_D^{20}$ +18.5 (c 0.2, $CH_2Cl_2$); IR ($CHCl_3$, $cm^{-1}$) 3019, 1738, 1658, 1600, 1531, 1215, 1155, 761; $^1H$ NMR (300 MHz, $CDCl_3$) δ0.19 (s, 3 H), 0.90–0.96 (m, 2 H), 1.03 (t, J=7 Hz, 3 H), 1.58 (s, 9 H), 1.8–2.0 (m, 2 H), 3.02–3.08 (m, 2 H), 3.89 (s, 1 H), 5.21. (s, 2 H), 5.30 (d, J=16 Hz, 1 H), 5.75 (d, J=16 Hz, 1 H), 6.85 (br s, 1 H), 7.57 (dd, $J_1$=9 Hz, $J_2$=2 Hz, 1 H), 7.61 (s, 1 H), 8.11 (d, J=9 Hz, 1 H), 8.31 (br s, 1 H); $^{13}C$ NMR (75 MHz, $CDCl^3$) δ–1.7, 8.0, 17.5, 24.4, 28.5, 31.8, 49.5, 66.5, 73.0, 77.4, 81.4, 97.7, 110.1, 118.2, 123.3, 126.7, 127.6, 131.4, 137.8, 146.2, 147.4, 150.37, 150.4, 152.6, 157.8, 174.1; HRMS (EI) m/z calcd for $C_{30}H_{37}N_3O_6Si$ ($M^+$) 563.2452, found 563.2426 LRMS (EI) m/z 463 ($M-C_5H_8O_2$), 419, 404, 363, 363, 346, 332, 289, 246, 149, 131, 73, 57.

(2) (20S)-10-Amino-7-[2-trimethylsilyl)ethyl]camptothecin (36b)

The camptothecin derivative prepared in (2) above (17.5 mg, 0.031 mmol) was dissolved in $CH_2Cl_2$ (1 mL) and trifluoroacetic acid (0.25 mL) was added. After 3 h at 22° C., the mixture was poured into saturated $NaHCO_3$ (20 mL) and extracted with EtOAc (10×15 mL). The organic phase was dried ($Na_2SO_4$), concentrated and chromatographed ($CH_2Cl_2$/Acetone 85:15), to give 9.4 mg (65%) of a yellow solid: $[\alpha]_D^{20}$ +17.0 (c 0.2, $CH_2Cl_2$/MeOH 3:1); $^1H$ NMR (300 MHz, $CDCl_3$) δ0.15 (s, 9 H), 0.85–0.91 (m, 2 H), 0.99 (t, J=7 Hz, 3 H), 1.87–2.05 (m, 2 H), 2.85–2.98 (m, 2 H), 5.04 (d, J=19 Hz, 1 H), 5.09 (d, J=19 Hz 1 H), 5.29. (d, J=16 Hz, 1 H), 5.58 (d, J=16 Hz, 1 H), 7.01 (d, J=2 Hz, 1 H), 7.25 (dd, $J_1$=9 Hz, J $S_2$=2 Hz, 1 H), 7.54 (s, 1 H), 7.84 (d, J=9 Hz, 1 H); $^{13}C$ NMR (75 MHz, $CDCl_3$) δ1.8, 8.1, 17.4, 24.5, 31.8, 50.0, 66.4, 73.8, 98.4, 102.3, 118.2, 123.4, 127.2, 129.6, 131.3, 144.1, 145.2, 147.6, 147.9, 148.5, 152.4, 158.7, 174.6; HRMS (EI) m/z calcd for $C_{25}H_{29}N_3O_4Si$ ($M^+$) 463.1927, found 463.1941 LRMS (EI) m/z 463 ($M^+$), 434, 419, 404, 390, 362, 346, 332, 167, 131, 104, 91, 73, 57.

Example 23

(20S)-7-[(2-Trimethylsilyl)ethyl]camptothecin (36c) (DB-172)

Following the procedure described in example 1-(2), a mixture of the iodopyridone (43) prepared in Example 21-(4) above (56.8 mg, 0.12 mmol) and phenylisonitrile (30.9 mg, 0.3 mmol) provided after flash chromatography ($CH_2Cl_2$/acetone 10:1) 28 mg (52%) of (20S)-7-[(2-trimethylsilyl)ethyl]camptothecin as a tan solid: $[\alpha]_D^{20}$+ 29.8 (c 0.2, $CH_2Cl_2$); IR ($CHCl_3$, $cm^{-1}$) 2996, 2954, 1742, 1659, 1601, 1557, 1250, 1158, 856; $^1H$ NMR (300 MHz, $CDCl_3$) δ0.18 (s, 9 H), 0.90–0.96 (m, 2 H), 1.04 (t, J=7.3 Hz, 3 H), 1.86–1.95 (m, 2 H), 3.07–3.13 (m, 2 H), 3.87 (s, 1 H), 5.23. (s, 2 H), 5.31 (d, J=16.3 Hz, 1 H), 5.76 (d, J=16.3 Hz, 1 H), 7.64–7.69 (m, 2 H), 7.80 (td, $J_1$=8 Hz, $J_2$=0.87 Hz, 1 H), 8.03 (d, J=8.3 Hz, 1 H), 8.23 (d, J=8.3 Hz, 1 H); $^{13}C$ NMR (75 MHz, $CDCl_3$) δ–1.75, 7.95, 17.9, 24.2, 31.7, 49.4, 66.5, 72.9, 98.1, 118.5, 123.4, 126.1, 126.7, 127.7, 130.3, 130.8, 147.1, 147.2, 149.6, 150.2, 152.0, 157.8, 174.1; HRMS (EI) m/z calcd for $C_{25}H_{28}N_2O_4Si$ ($M^+$) 448.1818, found 448.1819 LRMS (EI) m/z 448 ($M^+$), 431, 374, 358, 311, 301, 208, 195, 165, 149, 131, 118, 105, 93, 73.

Although the present invention has been described in detail in connection with the above examples, it is to be understood that such detail is solely for that purpose and that variations can be made by those skilled in the art without departing from the spirit of the invention except as it may be limited by the following claims.

What is claimed is:
1. A compound having the formula:

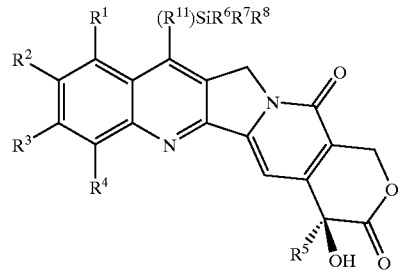

wherein $R^1$ and $R^2$ are independently the same or different and are hydrogen, an alkyl group, a hydroxyalkyl group, a haloalkyl group, an aminoalkyl group, an alkylaminoalkyl group, a dialkylaminoalkyl group, an alkenyl group, an alkynyl group, an alkoxy group, an aryloxy group, an acyloxy group, $—OC(O)OR^d$, wherein $R^d$ is an alkyl group, a carbamoyloxy group, a halogen, a hydroxy group, a nitro group, a cyano group, an azido group, a formyl group, a hydrazino group, $—C(O)R^f$ wherein $R^f$ is an alkyl group, an alkoxy group, an amino group or a hydroxy group, an amino group, an alkylamino group, a dialkylamino group, $—SR^e$, wherein $R^e$ is hydrogen, $—C(O)R^f$, an alkyl group, or an aryl group; or $R^1$ and $R^2$ together form a group of the formula $—O(CH_2)_nO—$ wherein n represents the integer 1 or 2

$R^3$ is H, a halogen atom, a nitro group, an amino group, a hydroxy group, or a cyano group; or $R^2$ and $R^3$ together form a group of the formula $—O(CH_2)_nO—$ wherein n represents the integer 1 or 2;

$R^4$ is H, F, a $C_{1-3}$ alkyl group, a $C_{2-3}$ alkenyl group, a C2-3 alkynyl group, a trialkylsilyl group, or a $C_{1-3}$ alkoxy group;

wherein at least one of $R^1$, $R^2$, $R^3$, and $R^4$ is not H, a halogen, an alkyl group, an amino group or a nitro group;

$R^5$ is a $C_{1-10}$ alkyl group, an allyl group, a benzyl group or a propargyl group;

$R^6$, $R^7$ and $R^8$ are independently a $C_{1-10}$ alkyl group, a $C_{2-10}$ alkenyl group, a C2-10 alkynyl group, an aryl group or a $—(CH_2)_NR^9$ group, wherein N is an integer within the range of 1 through 10 and $R^9$ is a hydroxy group, alkoxy group, an amino group, an alkylamino group, a dialkylamino group, a halogen atom, a cyano group or a nitro group; and $R^{11}$ is an alkylene group or an alkenylene group; and pharmaceutically acceptable salts thereof.

2. The compound of claim 1, wherein $R^4$ is H.
3. The compound of claim 1, wherein $R^1$ and $R^2$ are independently the same or different and are H, a hydroxy group, a halogen, an amino group, a nitro group, a cyano group, a $C_{1-3}$ alkyl group, a $C_{2-3}$ alkenyl group, a $C_{2-3}$ alkynyl group or a $C_{1-3}$ alkoxy group.
4. The compound of claim 1, wherein $R^1$ and $R^2$ are independently the same or different and are H, a $C_{1-3}$ perhaloalkyl group, a $C_{1-3}$ aminoalkyl group, a $C_{1-3}$ alkylamino group or a $C_{1-3}$ dialkylamino group.
5. The compound of claim 1, wherein $R^1$ and $R^2$ are independently the same or different and are H, a methyl group, an amino group, a nitro group, a cyano group, or a hydroxy group.
6. The compound of claim 1, wherein $R^1$ and $R^2$ are independently the same or different and are H, a methylamino group, a dimethylamino group, an ethylamino group, a diethylamino group, a hydroxymethyl group, an aminomethyl group, a methylaminomethyl group, or a dimethylaminomethyl group.

7. The compound of claim 1, wherein $R^3$ is F, an amino group, or a hydroxy group.

8. The compound of claim 1, wherein $R^5$ is an ethyl group.

9. The compound of claim 1, wherein $R^6$, $R^7$ and $R^8$ are independently the same or different and are a $C_{1-6}$ alkyl group, a phenyl group or a —$(CH_2)_N R^9$ group, wherein N is an integer within the range of 1 through 6 and $R^9$ is a hydroxy group, alkoxy group an amino group, an alkylamino group a dialkylamino group, a halogen atom, a cyano group or a nitro group.

10. The compound of claim 1, wherein $R^6$, $R^7$ and $R^8$ are methyl groups.

11. The compound of claim 1, wherein $R^2$ and $R^3$ form a methylenedioxy group, or a 1,2-ethylenedioxy group.

12. The compound of claim 1, wherein $R^2$ is OH.

13. The compound of claim 1, wherein $R^2$ is $NH_2$.

14. The compound of claim 1, wherein $R^{11}$ is a $C_2$–$C_{10}$ alkylene group, a $C_2$–$C_{10}$ alkenylene group or a $C_1$–$C_{10}$ alkynylene group.

15. The compound of claim 14, wherein $R^{11}$ is a $C_2$–$C_6$ alkylene group, a $C_2$–$C_6$ alkenylene group or a $C_1$–$C_6$ alkynylene group.

16. The compound of claim 14, wherein $R^{11}$ is $(CH_2)_m$ wherein m is an integer of 1 to 6.

17. The compound of claim 1 wherein $R^5$ is a methyl group, a $C_{3-10}$ alkyl group, an allyl group, a benzyl group or a propargyl group.

18. A compound having the formula:

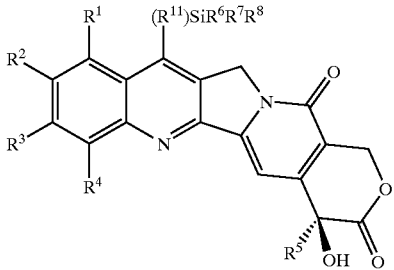

wherein $R^1$ and $R^2$ are independently the same or different and are hydrogen, an alkyl group, a hydroxyalkyl group, a haloalkyl group, an aminoalkyl group, an alkylaminoalkyl group, a dialkylaminoalkyl group, an alkenyl group, an alkynyl group, an alkoxy group, an aryloxy group, an acyloxy group, —$OC(O)OR^d$, wherein $R^d$ is an alkyl group, a carbamoyloxy group, a halogen, a hydroxy group, a nitro group, a cyano group, an azido group, a formyl group, a hydrazino group, —$C(O)R^f$ wherein $R^f$ is an alkyl group, an alkoxy group, an amino group or a hydroxy group, an amino group, an alkylamino group, a dialkylamino group, —$SR^c$, wherein $R^c$ is hydrogen, —$C(O)R^f$, an alkyl group, or an aryl group; or $R^1$ and $R^2$ together form a group of the formula —$O(CH_2)_nO$— wherein n represents the integer 1 or 2; wherein at least one of $R^1$ and $R^2$ is not H, a halogen, an alkyl group, an amino group or a nitro group;

$R^3$ is H, a halogen atom, a nitro group, an amino group, a hydroxy group, or a cyano group; or $R^2$ and $R^3$ together form a group of the formula —$O(CH_2)_nO$— wherein n represents the integer 1 or 2;

$R^4$ is H, F, a $C_{1-3}$ alkyl group, a $C_{2-3}$ alkenyl group, a $C_{2-3}$ alkynyl group, a trialkylsilyl group, or a $C_{1-3}$ alkoxy group;

$R^5$ is a $C_{1-10}$ alkyl group, an allyl group, a benzyl group or a propargyl group;

$R^6$, $R^7$ and $R^8$ are independently a $C_{1-10}$ alkyl group, a $C_{2-10}$ alkenyl group, a $C_{2-10}$ alkynyl group, an aryl group or a —$(CH_2)_N R^9$ group, wherein N is an integer within the range of 1 through 10 and $R^9$ is a hydroxy group, alkoxy group, an amino group, an alkylamino group, a dialkylamino group, a halogen atom, a cyano group or a nitro group; and $R^{11}$ is an alkylene group or an alkenylene group; and pharmaceutically acceptable salts thereof.

19. A compound having the formula:

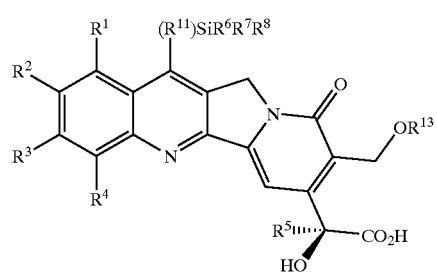

wherein $R^1$ and $R^2$ are independently the same or different and are hydrogen, an alkyl group, a hydroxyalkyl group, a haloalkyl group, an aminoalkyl group, an alkylaminoalkyl group, a dialkylaminoalkyl group, an alkenyl group, an alkynyl group, an alkoxy group, an aryloxy group, an acyloxy group, —$OC(O)OR^d$, wherein $R^d$ is an alkyl group, a carbamoyloxy group, a halogen, a hydroxy group, a nitro group, a cyano group, an azido group, a formyl group, a hydrazino group, —$C(O)R^f$ wherein $R^f$ is an alkyl group, an alkoxy group, an amino group or a hydroxy group, an amino group, an alkylamino group, a dialkylamino group, —$SR^c$, wherein $R^c$ is hydrogen, —$C(O)R^f$, an alkyl group, or an aryl group; or $R^1$ and $R^2$ together form a group of the formula —$O(CH_2)_nO$— wherein n represents the integer 1 or 2; provided that at least one of $R^1$ and $R^2$ is not H, a halogen, an alkyl group or a nitro group;

$R^3$ is H, a halogen atom, a nitro group, an amino group, a hydroxy group, or a cyano group; or $R^2$ and $R^3$ together form a group of the formula —$O(CH_2)_nO$— wherein n represents the integer 1 or 2;

$R^4$ is H, F, a $C_{1-3}$ alkyl group, a $C_{2-3}$ alkenyl group, a $C_{2-3}$ alkynyl group, a trialkylsilyl group, or a $C_{1-3}$ alkoxy group;

$R^5$ is a $C_{1-10}$ alkyl group, an allyl group, a benzyl group or a propargyl group;

$R^6$, $R^7$ and $R^8$ are independently a $C_{1-10}$ alkyl group, a $C_{2-10}$ alkenyl group, a $C_{2-10}$ alkynyl group, an aryl group or a —$(CH_2)_N R^9$ group, wherein N is an integer within the range of 1 through 10 and $R^9$ is a hydroxy group, alkoxy group, an amino group, an alkylamino group, a dialkylamino group, a halogen atom, a cyano group or a nitro group; and $R^{11}$ is an alkylene group or an alkenylene group; and pharmaceutically acceptable salts thereof.

* * * * *